United States Patent
Horiuchi et al.

(10) Patent No.: US 12,201,460 B2
(45) Date of Patent: Jan. 21, 2025

(54) RADIOGRAPHY APPARATUS, METHOD FOR OPERATING RADIOGRAPHY APPARATUS, AND PROGRAM FOR OPERATING RADIOGRAPHY APPARATUS

(71) Applicant: FUJIFILM CORPORATION, Tokyo (JP)

(72) Inventors: Hisatsugu Horiuchi, Kanagawa (JP); Sho Shimizukawa, Kanagawa (JP); Masakazu Fukuyo, Kanagawa (JP); Naoyuki Nishino, Kanagawa (JP); Takashi Tajima, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 297 days.

(21) Appl. No.: 17/806,734

(22) Filed: Jun. 14, 2022

(65) Prior Publication Data
US 2023/0018119 A1 Jan. 19, 2023

(30) Foreign Application Priority Data
Jul. 19, 2021 (JP) .................................. 2021-118901

(51) Int. Cl.
*A61B 6/02* (2006.01)
*A61B 6/00* (2024.01)
(Continued)

(52) U.S. Cl.
CPC .............. *A61B 6/02* (2013.01); *A61B 6/4208* (2013.01); *A61B 6/5205* (2013.01); *A61B 6/0407* (2013.01)

(58) Field of Classification Search
CPC ........... A61B 6/02; A61B 6/03; A61B 6/4208; A61B 6/5205; A61B 6/0407; A61B 6/04;
(Continued)

(56) References Cited

U.S. PATENT DOCUMENTS

| 11,054,532 B2 * | 7/2021 | Hjärn ...................... G01T 1/243 |
| 2003/0200655 A1 | 10/2003 | Vafi et al. |

(Continued)

FOREIGN PATENT DOCUMENTS

| JP | 2003-339688 A | 12/2003 |
| JP | 2014-226321 A | 12/2014 |

(Continued)

OTHER PUBLICATIONS

English language translation of the following: Office action dated Nov. 26, 2024 from the JPO in a Japanese patent application No. 2021-118901 corresponding to the instant patent application. This office action translation is submitted now in order to supplement the understanding of the cited references which are being disclosed in the instant Information Disclosure Statement.

*Primary Examiner* — David P Porta
*Assistant Examiner* — Richard O Toohey
(74) *Attorney, Agent, or Firm* — SOLARIS Intellectual Property Group, PLLC

(57) ABSTRACT

A radiation detector has a sensor panel unit which includes two sensor panels and in which end portions of the two sensor panels are arranged to overlap each other in a thickness direction. An image processing unit acquires two projection images from the two sensor panels. A combination unit of the image processing unit performs a process related to image quality on the projection image in a case in which a tomographic image which is a diagnosis image to be used for a doctor's diagnosis is generated and does not perform the process related to image quality on the projection image in a case in which a scout image which is a confirmation image for confirming a reflected state of the subject is generated.

21 Claims, 38 Drawing Sheets

| | DETECTION OF POSITIONAL DEVIATION | CORRECTION OF POSITIONAL DEVIATION | SPECIFICATION OF REFLECTED REGION | REMOVAL OF SIGNAL OF REFLECTED REGION |
|---|---|---|---|---|
| SCOUT IMAGE | NOT PERFORM | NOT PERFORM | NOT PERFORM | NOT PERFORM |
| TOMOGRAPHIC IMAGE | PERFORM | PERFORM | PERFORM | PERFORM |

(51) Int. Cl.
*A61B 6/04* (2006.01)
*A61B 6/42* (2024.01)

(58) Field of Classification Search
CPC ... A61B 6/0478; A61B 6/4266; A61B 6/4435; A61B 6/032; A61B 6/4405; G01T 1/161
See application file for complete search history.

(56) References Cited

U.S. PATENT DOCUMENTS

| | | | |
|---|---|---|---|
| 2006/0185165 A1* | 8/2006 | Vafi | H01L 27/14658 29/854 |
| 2009/0084962 A1* | 4/2009 | Kito | G01T 7/00 250/369 |
| 2012/0051512 A1* | 3/2012 | Ohta | A61B 6/022 378/62 |
| 2017/0065239 A1* | 3/2017 | Higuma | A61B 6/468 |
| 2018/0172849 A1* | 6/2018 | Nelson | G01T 1/20182 |
| 2021/0072410 A1 | 3/2021 | Yu et al. | |
| 2022/0022825 A1* | 1/2022 | Nakagawa | A61B 6/0407 |

FOREIGN PATENT DOCUMENTS

| | | |
|---|---|---|
| JP | 2016-059611 A | 4/2016 |
| JP | 2021-043201 A | 3/2021 |
| JP | 2021-069699 A | 5/2021 |
| JP | 2021-074378 A | 5/2021 |

\* cited by examiner

FIG. 15

IRRADIATION CONDITION TABLE 141

| IMAGING PROCEDURE | | | IRRADIATION CONDITIONS (TUBE VOLTAGE TUBE CURRENT IRRADIATION TIME) 156 | | | |
|---|---|---|---|---|---|---|
| STANDING POSTURE | HEAD | ADULT MALE | 100KV | 10mA | 0.5ms | ⋮ |
| STANDING POSTURE | HEAD | ADULT FEMALE | 100KV | 10mA | 0.5ms | ⋮ |
| STANDING POSTURE | NECK | ADULT MALE | 80KV | 8mA | 0.5ms | ⋮ |
| ⋮ | | | ⋮ | | | |
| SITTING POSTURE | SPINE | ADULT MALE | 120KV | 12mA | 0.5ms | ⋮ |
| SITTING POSTURE | SPINE | ADULT FEMALE | 120KV | 12mA | 0.5ms | ⋮ |
| ⋮ | | | ⋮ | | | |

FIG. 24

| | DETECTION OF POSITIONAL DEVIATION | CORRECTION OF POSITIONAL DEVIATION | SPECIFICATION OF REFLECTED REGION | REMOVAL OF SIGNAL OF REFLECTED REGION |
|---|---|---|---|---|
| SCOUT IMAGE | NOT PERFORM | NOT PERFORM | NOT PERFORM | NOT PERFORM |
| TOMOGRAPHIC IMAGE | PERFORM | PERFORM | PERFORM | PERFORM |

| | OFFSET CORRECTION | DEFECTIVE PIXEL CORRECTION | SHADING CORRECTION | RESIDUAL IMAGE CORRECTION | SCATTERED RAY CORRECTION | REFERENCE CORRECTION |
|---|---|---|---|---|---|---|
| SCOUT IMAGE | PERFORM | PERFORM | NOT PERFORM | NOT PERFORM | NOT PERFORM | NOT PERFORM |
| TOMOGRAPHIC IMAGE | PERFORM | PERFORM | PERFORM | PERFORM | PERFORM | PERFORM |

235

RADIOGRAPHY APPARATUS, METHOD FOR OPERATING RADIOGRAPHY APPARATUS, AND PROGRAM FOR OPERATING RADIOGRAPHY APPARATUS

CROSS-REFERENCE TO RELATED APPLICATIONS

The present application claims priority under 35 U.S.C. § 119 to Japanese Patent Application No. 2021-118901, filed on Jul. 19, 2021. The above application is hereby expressly incorporated by reference, in its entirety, into the present application.

BACKGROUND

1. Technical Field

The technology of the present disclosure relates to a radiography apparatus, a method for operating the radiography apparatus, and a program for operating the radiography apparatus.

2. Description of the Related Art

A radiography apparatus is known which irradiates a subject with radiation from a radiation source and detects the radiation transmitted through the subject with a radiation detector to obtain a radiographic image of the subject. An imaging sensor is provided in the radiation detector. The imaging sensor has pixels. The pixels sense the radiation or visible light converted from the radiation and generate charge. A radiographic image is obtained by reading out the charge from the pixels and performing various types of signal processing.

JP2003-339688A discloses a radiation detector that is used in a computed tomography (hereinafter, abbreviated to CT) apparatus and has an imaging sensor unit in which a plurality of imaging sensors having a rectangular plate shape are arranged. FIG. 12 of JP2003-339688A illustrates the imaging sensor unit in which end portions of two adjacent imaging sensors overlap each other in a thickness direction. Further, FIG. 5 and paragraph [0035] of JP2003-339688A disclose a configuration that removes a signal of a reflected region in which the end portion of one imaging sensor disposed on the incident side of radiation is reflected in the other imaging sensor in the imaging sensor unit in which the end portions of the two adjacent imaging sensors overlap each other in the thickness direction and then reconstructs the tomographic image.

SUMMARY

In some cases, the radiography apparatus generates a confirmation image for an operator, such as a radiology technician, to confirm the reflected state of the subject at an imaging site, in addition to the diagnosis image used for the doctor's diagnosis such as the tomographic image described in JP2003-339688A. The quality of the confirmation image does not need to be as high as that of the diagnosis image since the confirmation image is just used to confirm the reflected state of the subject. As the time required to generate the confirmation image increases, the entire imaging time increases. Therefore, it is preferable to generate the confirmation image as quickly as possible.

In JP2003-339688A, as described above, in a case in which the tomographic image which is the diagnosis image is reconstructed, the signal of the reflected region is removed. However, in a case in which the process related to image quality is also performed on the confirmation image, the time required to generate the confirmation image increases.

One embodiment according to the technology of the present disclosure is to provide a radiography apparatus, a method for operating the radiography apparatus, and a program for operating the radiography apparatus that can generate a confirmation image for confirming a reflected state of a subject in a short time while ensuring the quality of a diagnosis image to be used for a doctor's diagnosis.

According to an aspect of the present disclosure, there is provided a radiography apparatus comprising: a radiation source that irradiates a subject with radiation; a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction; a processor; and a memory that is connected to or provided in the processor. The processor acquires a radiographic image of the subject from the imaging sensor, performs a process related to image quality on the radiographic image in a case in which a diagnosis image to be used for a doctor's diagnosis is generated from the radiographic image, and does not perform the process related to image quality on the radiographic image in a case in which a confirmation image for confirming a reflected state of the subject is generated from the radiographic image.

Preferably, the first imaging sensor has a first imaging region in which the pixels are arranged, and the second imaging sensor has a second imaging region in which the pixels are arranged. Preferably, the first imaging sensor is disposed closer to an incident side of the radiation than the second imaging sensor in the thickness direction. Preferably, in the second imaging region, a reflected region in which the first end portion is reflected is present in at least an overlap region in which the first end portion and the second end portion overlap each other. Preferably, the processor removes a signal of the reflected region from the radiographic image in a case in which the diagnosis image is generated and does not remove the signal of the reflected region from the radiographic image in a case in which the confirmation image is generated.

Preferably, the first imaging region and the second imaging region overlap each other in the overlap region in a plan view of the imaging sensor unit in the thickness direction.

Preferably, a marker that is reflected in both the first imaging sensor and the second imaging sensor is attached to the radiation detector at a preset position, and the processor detects a positional deviation of the first imaging sensor and the second imaging sensor on the basis of the set position and a position where the marker is actually reflected and specifies the reflected region on the basis of the detected positional deviation.

Preferably, an irradiation angle of the radiation with respect to the radiation detector is changeable, and the processor specifies the reflected region that changes depending on the irradiation angle.

Preferably, the radiation is capable of being obliquely incident on the overlap region, and a size of a focus of the radiation is changeable. Preferably, the processor specifies the reflected region that changes depending on the size of the focus.

Preferably, a distance between the first imaging sensor and the second imaging sensor in the thickness direction is equal to or less than 2 mm.

Preferably, a width of the reflected region is equal to or less than 10 mm.

Preferably, a length of one side of the imaging sensor is equal to or greater than 300 mm.

Preferably, the radiation detector includes a support table having an attachment surface which is convex toward an opposite side of the radiation source and to which the imaging sensor unit is attached following the convex shape.

Preferably, the convex shape is a U-shape or a V-shape.

Preferably, in a case in which the convex shape is the U-shape, a tangent line between the first imaging sensor and the second imaging sensor in the overlap region is parallel to a tangent line between the second imaging sensor and the support table in the overlap region.

Preferably, in a case in which the convex shape is the U-shape, centers of curvature of at least two imaging sensors are located at the same position.

Preferably, the imaging sensor unit includes two imaging sensors of the first imaging sensor and the second imaging sensor.

Preferably, the imaging sensor is a sensor panel in which the pixels including thin film transistors are two-dimensionally arranged.

Preferably, a substrate of the sensor panel is made of a resin.

Preferably, the radiography apparatus further comprises: an annular frame to which the radiation source and the radiation detector are attached and in which the subject is positioned in a cavity; and a rotation mechanism that rotates the frame around the subject to capture the radiographic images at different angles. Preferably, the radiation detector includes a support table having an attachment surface which has an arc surface shape toward an opposite side of the radiation source and to which the imaging sensor unit is attached following the arc surface shape.

Preferably, the radiography apparatus is a computed tomography apparatus that generates a tomographic image of the subject as the diagnosis image on the basis of a plurality of the radiographic images captured at different angles.

Preferably, the confirmation image is a scout image that is obtained by scout imaging performed before the tomographic image is captured.

Preferably, the confirmation image is a preview image that is generated on the basis of one of the plurality of radiographic images captured at different angles and is displayed before the tomographic image is displayed.

Preferably, the radiation source emits the radiation having a conical shape.

Preferably, the subject is positioned in the cavity in either a standing posture or a sitting posture.

According to another aspect of the present disclosure, there is provided a method for operating a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction. The method comprises: acquiring a radiographic image of the subject from the imaging sensor; performing a process related to image quality on the radiographic image in a case in which a diagnosis image to be used for a doctor's diagnosis is generated from the radiographic image; and not performing the process related to image quality on the radiographic image in a case in which a confirmation image for confirming a reflected state of the subject is generated from the radiographic image.

According to still another aspect of the present disclosure, there is provided a program for operating a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction. The program causes a computer to execute a process comprising: acquiring a radiographic image of the subject from the imaging sensor; performing a process related to image quality on the radiographic image in a case in which a diagnosis image to be used for a doctor's diagnosis is generated from the radiographic image; and not performing the process related to image quality on the radiographic image in a case in which a confirmation image for confirming a reflected state of the subject is generated from the radiographic image.

According to the technology of the present disclosure, it is possible to provide a radiography apparatus, a method for operating the radiography apparatus, and a program for operating the radiography apparatus that can generate a confirmation image for confirming a reflected state of a subject in a short time while ensuring the quality of a diagnosis image to be used for a doctor's diagnosis.

BRIEF DESCRIPTION OF THE DRAWINGS

Exemplary embodiments according to the technique of the present disclosure will be described in detail based on the following figures, wherein:

FIG. 15 is a diagram illustrating an irradiation condition table;

FIG. 24 is a table summarizing whether or not the process is performed in a case in which the scout image is generated and in a case in which the tomographic image is generated;

FIG. 39 is a table summarizing another example of whether or not the process is performed in a case in which the scout image is generated and in a case in which the tomographic image is generated.

DETAILED DESCRIPTION

First Embodiment

Figure 1:
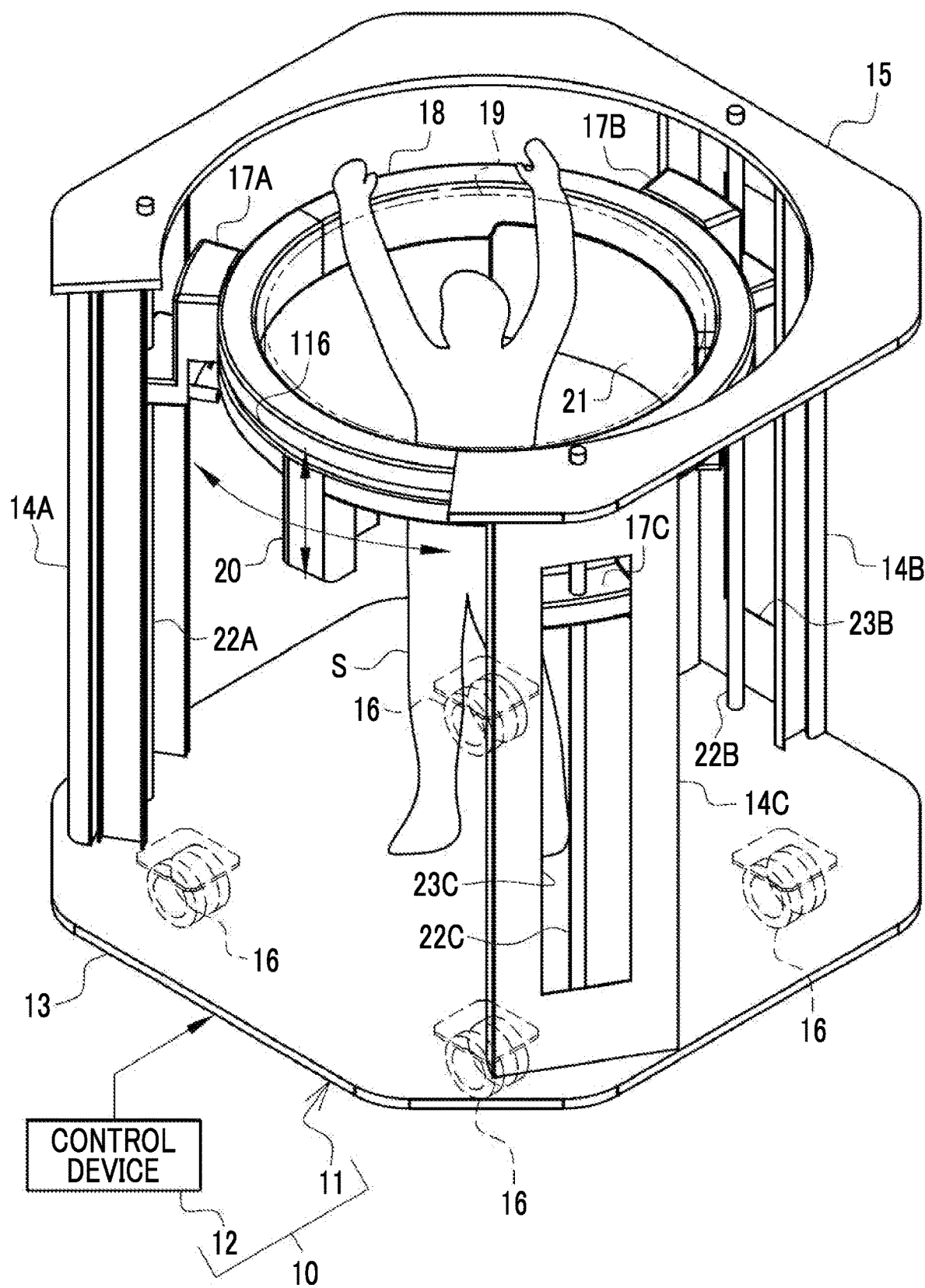
FIG. 1 is a perspective view illustrating a CT apparatus.
Figure 2:
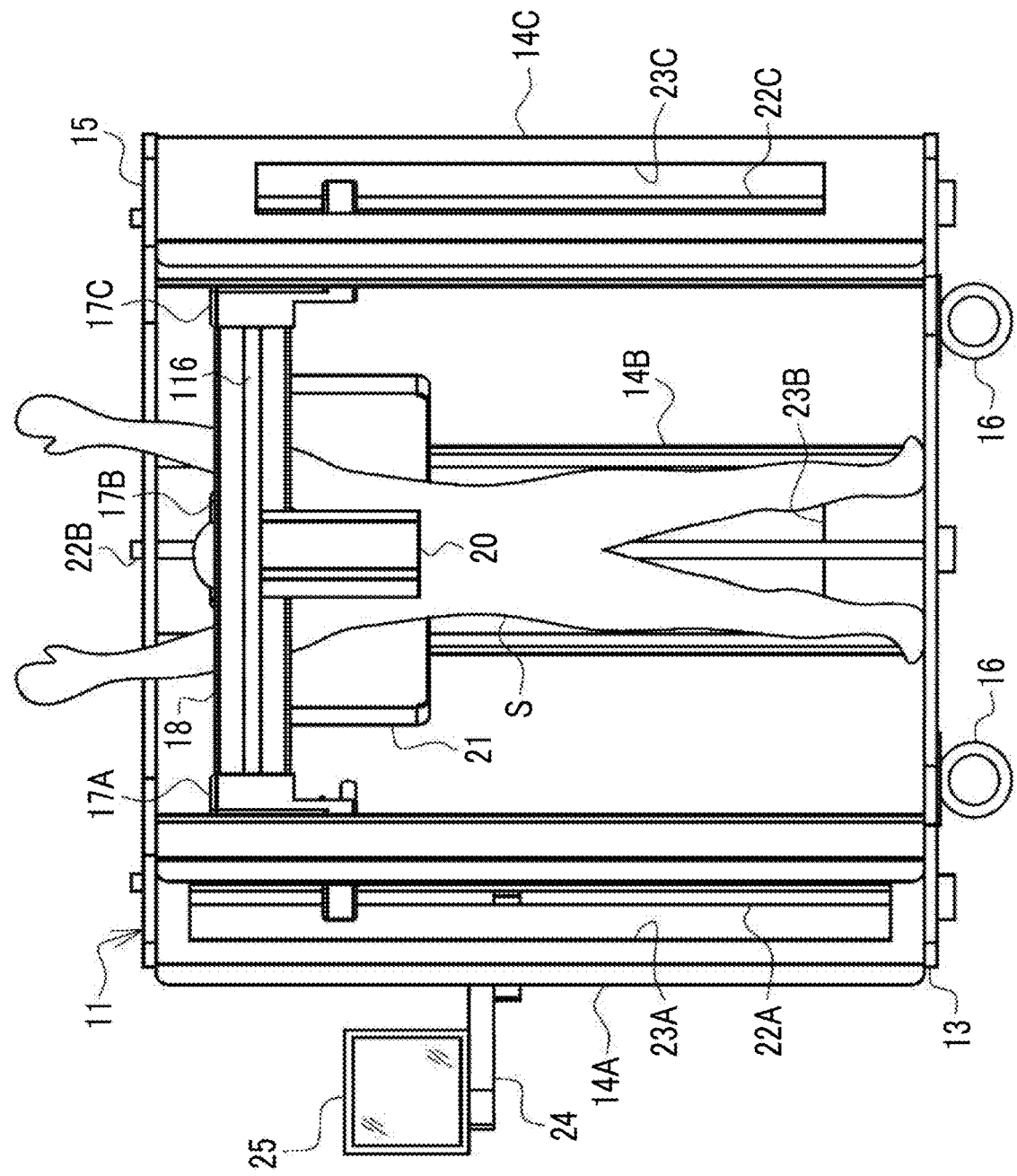
FIG. 2 is a front view illustrating an apparatus main body of the CT apparatus.
Figure 3:
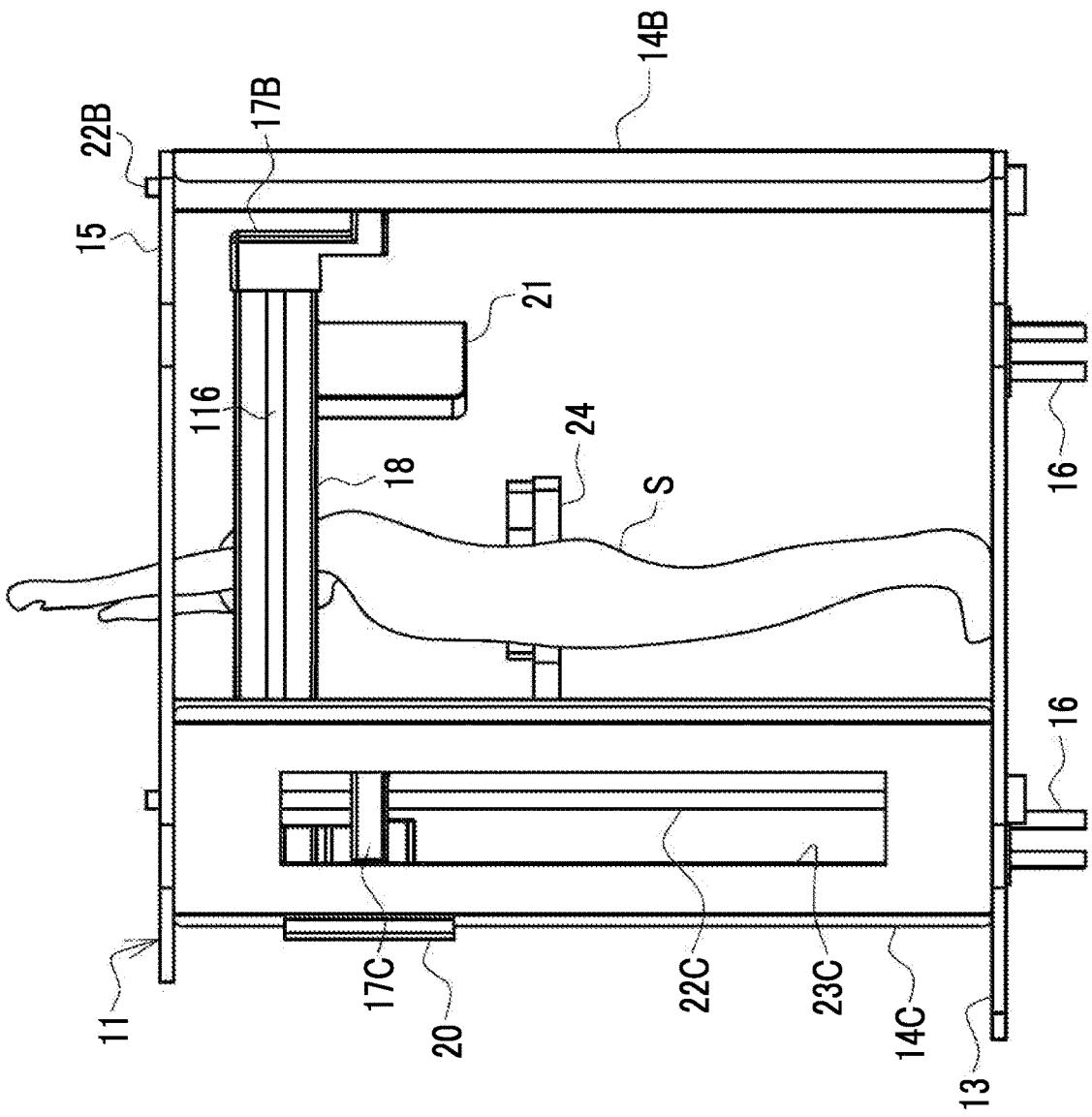
FIG. 3 is a side view illustrating the apparatus main body of the CT apparatus.

For example, as illustrated in FIG. 1, a CT apparatus 10 is an apparatus for obtaining a tomographic image TI (see FIG. 17) of a subject S and includes an apparatus main body 11 and a control device 12. The apparatus main body 11 is installed, for example, in a radiography room of a medical facility. The control device 12 is installed, for example, in a control room next to the radiography room. The control device 12 is a desktop personal computer, a notebook personal computer, or a tablet terminal. The CT apparatus 10 is an example of a "radiography apparatus" according to the technology of the present disclosure. In addition, the tomographic image TI is an example of a "diagnosis image" according to the technology of the present disclosure.

For example, as illustrated in FIGS. 1 to 4, the apparatus main body 11 comprises a stage 13, three columns 14A, 14B, and 14C, and a top plate 15. The stage 13 is an octagonal flat surface. Casters 16 for transportation are attached to four corners of a rear surface of the stage 13.

The caster 16 comprises a rotation lock mechanism (not illustrated). After the apparatus main body 11 is installed at an installation position, the rotation lock mechanism can be operated to lock the rotation of the caster 16. Alternatively, the caster 16 can be removed from the stage 13. The caster 16 can be removed after the apparatus main body 11 is installed at the installation position.

The outer shape of the columns 14A to 14C is a rectangular plate shape, and the columns 14A to 14C are vertically provided at four corners of the surface of the stage 13. The columns 14A and 14C are disposed on the front left and right sides of the apparatus main body 11 (the front left and right sides of the subject S). The column 14B is disposed at the center of the rear side of the apparatus main body 11 (behind the subject S). The top plate 15 is attached to the upper end portions of the columns 14A to 14C. The top plate 15 is an octagonal flat surface having an outer shape following the stage 13. The top plate 15 has a C-shape in which a central portion is hollowed out in a circular shape and a portion corresponding to the front side of the apparatus main body 11 between the columns 14A and 14C is cut out. Further, in the following description, the columns 14A to 14C are collectively referred to as columns 14 in a case in which they do not need to be distinguished from each other.

A connection member 17A is connected to the column 14A, a connection member 17B is connected to the column 14B, and a connection member 17C is connected to the column 14C. A frame 18 is connected to the connection members 17A to 17C. That is, the columns 14A to 14C and the frame 18 are connected to each other through the connection members 17A to 17C. Furthermore, in the following description, the connection members 17A to 17C are collectively referred to as connection members 17 in a case in which they do not need to be distinguished from each other.

The frame 18 has an annular shape. The subject S is positioned at a center C (see FIG. 4) of a cavity 19 of the annular frame 18. FIGS. 1 to 4 illustrate an aspect in which the subject S in a standing posture with both hands raised above the head is positioned.

The column 14 is provided with a guide rail (not illustrated) to which the connection member 17 is fitted. The connection member 17 and thus the frame 18 can be moved up and down in the vertical direction along the guide rail. That is, the columns 14 hold the frame 18 so as to be movable up and down in the vertical direction. In addition, the frame 18 can be rotated around the subject S using the center C as a central axis. That is, the columns 14A to 14C hold the frame 18 so as to be rotatable around the subject S. Further, the height position of the frame 18 may be changed by expanding and contracting the columns 14.

A radiation source 20 that emits radiation R (see FIG. 6), such as X-rays or γ-rays, and a radiation detector 21 that detects the radiation R are attached to the frame 18. Both the radiation source 20 and the radiation detector 21 protrude from a lower edge of the frame 18. The radiation source 20 and the radiation detector 21 are disposed at opposite positions (positions that are 180° away from each other) of the frame 18. The radiation source 20 has a box shape, and the radiation detector 21 has a pad shape. In a plan view of the frame 18 or the like from above, the radiation detector 21 has an arc surface shape that is convex toward the opposite side of the radiation source 20 and follows the shape of the frame 18. The arc surface shape is an example of a "U-shape" according to the technology of the present disclosure.

The column 14A is provided with a screw shaft 22A, the column 14B is provided with a screw shaft 22B, and the column 14C is provided with a screw shaft 22C. The screw shafts 22A to 22C have a height from the stage 13 to the top plate 15. The screw shafts 22A to 22C are rotated such that the connection members 17A to 17C and thus the frame 18 are moved up and down in the vertical direction. In addition, in the following description, the screw shafts 22A to 22C are collectively referred to as screw shafts 22 in a case in which they do not need to be distinguished from each other.

The column 14A has an opening 23A, the column 14B has an opening 23B, and the column 14C has an opening 23C. The openings 23A to 23C are formed by hollowing out most of the columns 14A to 14C in a rectangular shape, respectively. The subject S can be visually recognized from the outside of the apparatus main body 11 through the openings 23A to 23C. Each of the columns 14A to 14C partially looks like two columns because of each of the openings 23A to 23C. However, since the column is connected at the top and bottom of each of the openings 23A to 23C, the number is columns is one.

A touch panel display 25 is attached to the column 14A through a movable arm 24. The touch panel display 25 is operated by an operator. Further, the touch panel display 25 displays various kinds of information to the operator.

Figure 4:
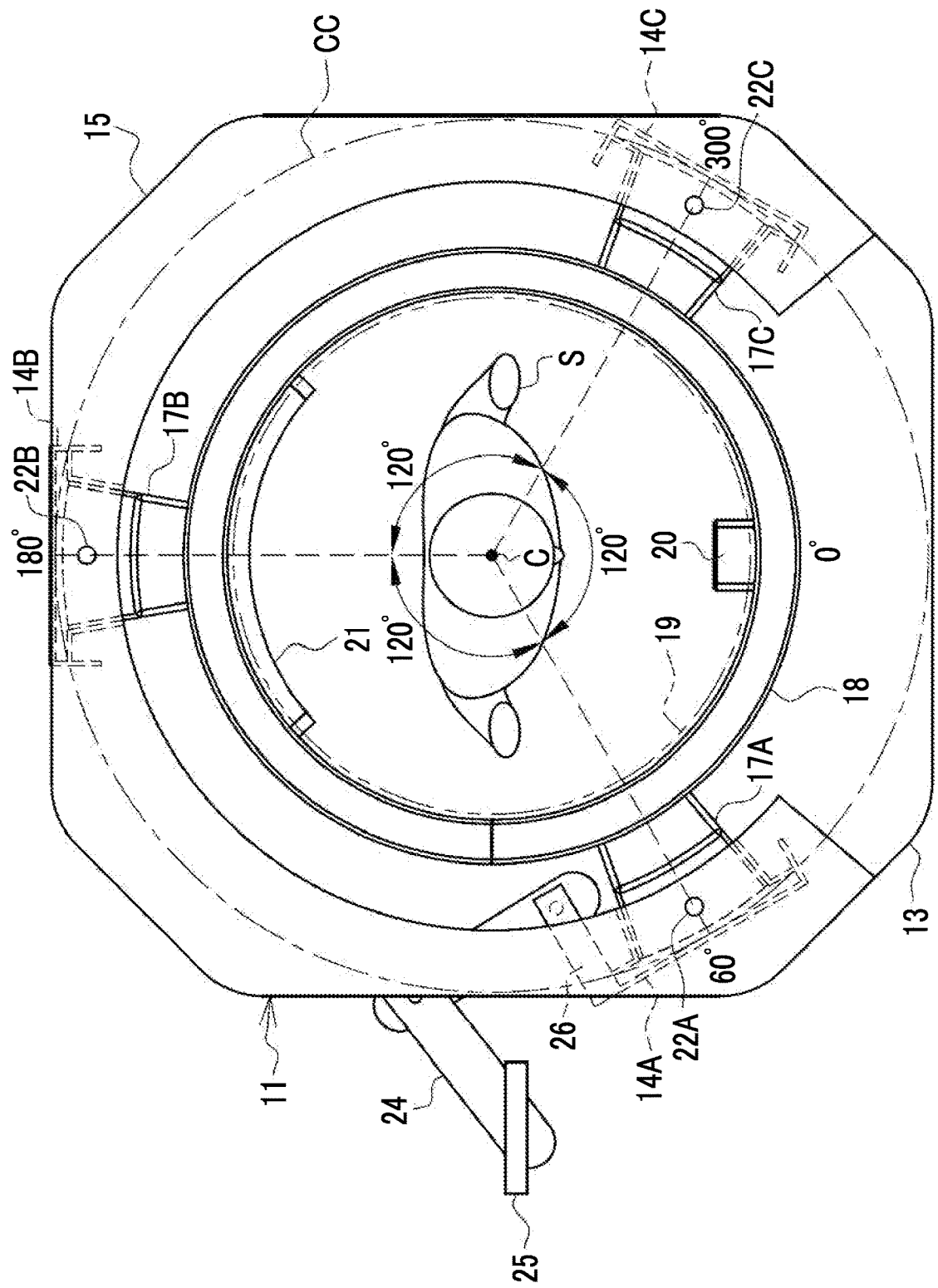
FIG. 4 is a top view illustrating the apparatus main body of the CT apparatus.

In FIG. 4 which is a plan view of the frame 18 and the like from above, in a case in which the position where the radiation source 20 is located in front of the apparatus main body 11 is set as a position of 0°, the column 14A is disposed at a position of 60° on a circle CC having the center C of the frame 18 as its center, the column 14B is disposed at a position of 180° on the circle CC, and the column 14C is disposed at a position of 300° on the circle CC. That is, the columns 14A to 14C are disposed at intervals of 120° on the circle CC. In addition, angles, such as "0°" and "60°", indicate, for example, "0°" and "60°" including an error (for example, an error of about 1% to 10%) that is generally allowed in the technical field to which the technology of the present disclosure belongs and does not depart from the gist of the technology of the present disclosure, in addition to perfect "0°" and "60°". Further, the term "equal interval" indicates an "equal interval" including an error (for example, an error of about 1% to 10%) that is generally allowed in the technical field to which the technology of the present disclosure belongs and does not depart from the gist of the technology of the present disclosure, in addition to a perfect "equal interval".

Figure 5:
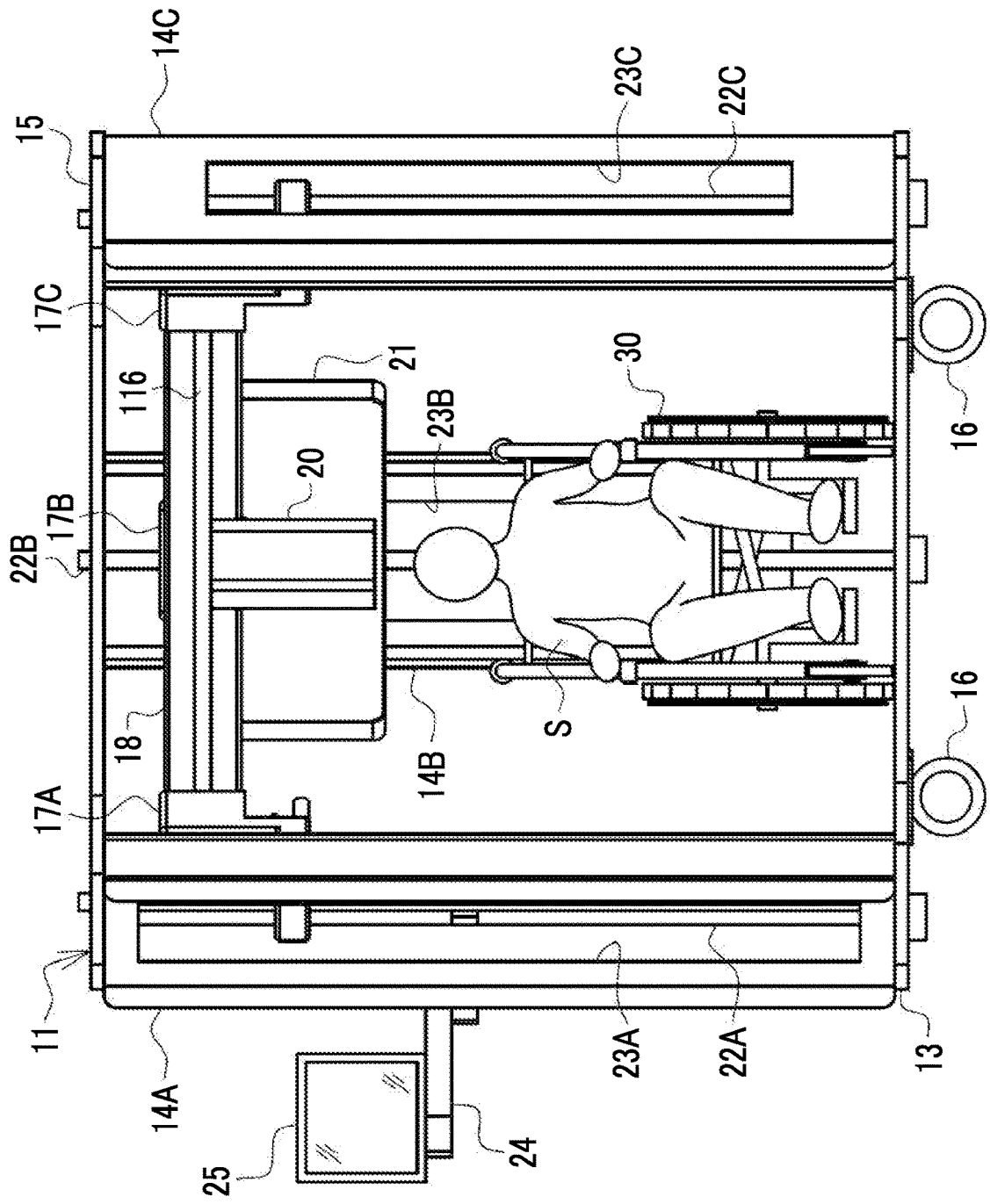
FIG. 5 is a front view illustrating the apparatus main body of the CT apparatus in a state in which a subject in a sitting posture on a wheelchair is positioned.

FIGS. 1 to 4 illustrate an example in which the subject S in a standing posture with both hands raised above the head is positioned in the cavity 19. However, the present disclosure is not limited to thereto. For example, as illustrated in FIG. 5, the CT apparatus 10 can image the subject S who is positioned in the cavity 19 in a sitting posture on a wheelchair 30. In addition, both the subject S in the standing posture and the subject S in the sitting posture on the wheelchair 30 are positioned so as to face the front at the position of 0°.

Figure 6:
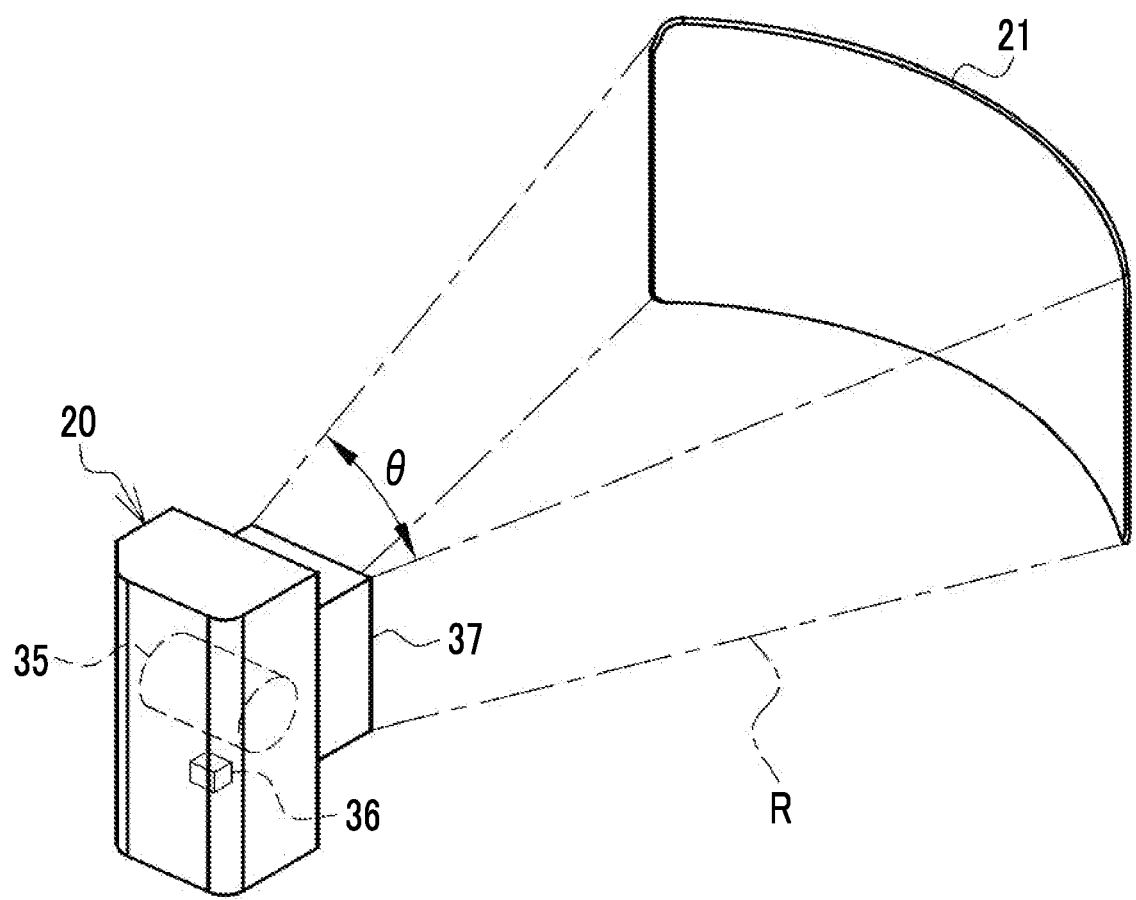
FIG. 6 is a perspective view illustrating a radiation source, a radiation detector, and radiation.

For example, as illustrated in FIG. 6, the radiation source 20 includes a radiation tube 35 and an irradiation field lamp 36. The radiation tube 35 emits the radiation R. The irradiation field lamp 36 emits, for example, orange visible light indicating the irradiation field of the radiation R.

Further, the radiation source 20 includes an irradiation field limiter 37. The irradiation field limiter 37 is also called a collimator and defines the irradiation field of the radiation R to the radiation detector 21. An incident opening through which the radiation R from the radiation tube 35 is incident and an exit opening through which the radiation R exits are formed in the irradiation field limiter 37. For example, four shielding plates are provided in the vicinity of the exit opening. The shielding plate is made of a material that shields the radiation R, for example, lead. The shielding plates are disposed on each side of a quadrangle, in other words, are assembled in a checkered pattern and form a quadrangular irradiation opening through which the radiation R is transmitted. The irradiation field limiter 37 changes the position of each shielding plate to change the size of the irradiation opening, thereby changing the irradiation field of the radiation R to the radiation detector 21. The radiation R having a quadrangular pyramid shape is emitted from the radiation source 20 by the operation of the irradiation field limiter 37. An irradiation angle θ of the radiation R is, for example, 45°.

Figure 7:
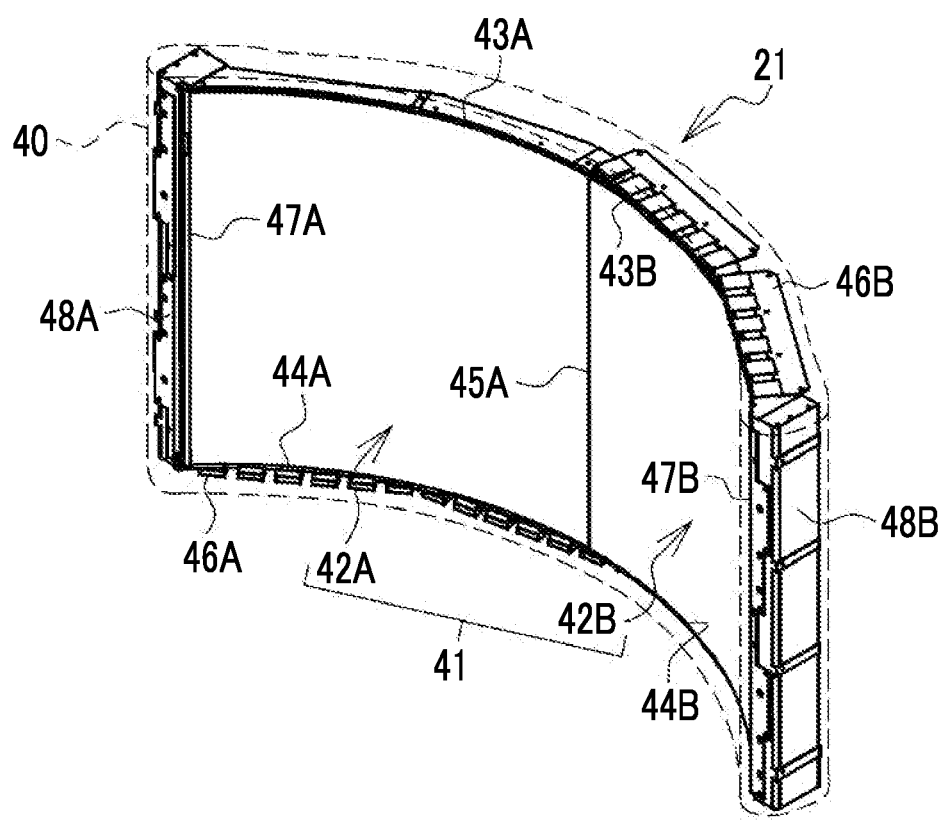
FIG. 7 is a perspective view illustrating the inside of the radiation detector.

For example, as illustrated in FIG. 7, the radiation detector 21 includes a housing 40 having an arc surface shape that follows the shape of the frame 18. The housing 40 is made of, for example, carbon. A sensor panel unit 41 is accommodated in the housing 40. The sensor panel unit 41 includes two sensor panels 42A and 42B using thin film transistors (hereinafter, abbreviated to TFTs). The sensor panels 42A and 42B have a square shape in which a length LP of one side is equal to or greater than 300 mm (LP≥300 mm) (see FIG. 8). Specifically, the sensor panels 42A and 42B have a square shape having a size of 17 inches (about 432 mm×about 432 mm). In the sensor panel 42A, opposite sides 43A and 44A are curved in an arc shape that follows the shape of the frame 18. Similarly, in the sensor panel 42B, opposite sides 43B and 44B are curved in an arc shape that follows the shape of the frame 18. The sensor panels 42A and 42B overlap each other on sides 45A and 45B that are not curved in an arc shape (see FIG. 8 and the like for the side 45B). In addition, the sensor panel unit 41 is an example of an "imaging sensor unit" according to the technology of the present disclosure. Further, the sensor panel 42A is an example of a "first imaging sensor" according to the technology of the present disclosure, and the sensor panel 42B is an example of a "second imaging sensor" according to the technology of the present disclosure.

A reading circuit board 46A is attached to the side 44A, and a reading circuit board 46B is attached to the side 43B. Nothing is attached to the side 43A facing the side 44A and the side 44B facing the side 43B. The sides 44A and 43B and thus the reading circuit boards 46A and 46B have a so-called two-fold symmetric relationship in which they are located at positions that are aligned with each other in a case in which they are rotated 180° about the center of the radiation detector 21.

A switching circuit board 48A is attached to a side 47A facing the side 45A, and a switching circuit board 48B is attached to a side 47B facing the side 45B. In addition, similarly to the columns 14A to 14C, hereinafter, the sensor panels 42A and 42B and each component attached thereto may be represented by only numbers without letters "A" and "B".

Figure 8:
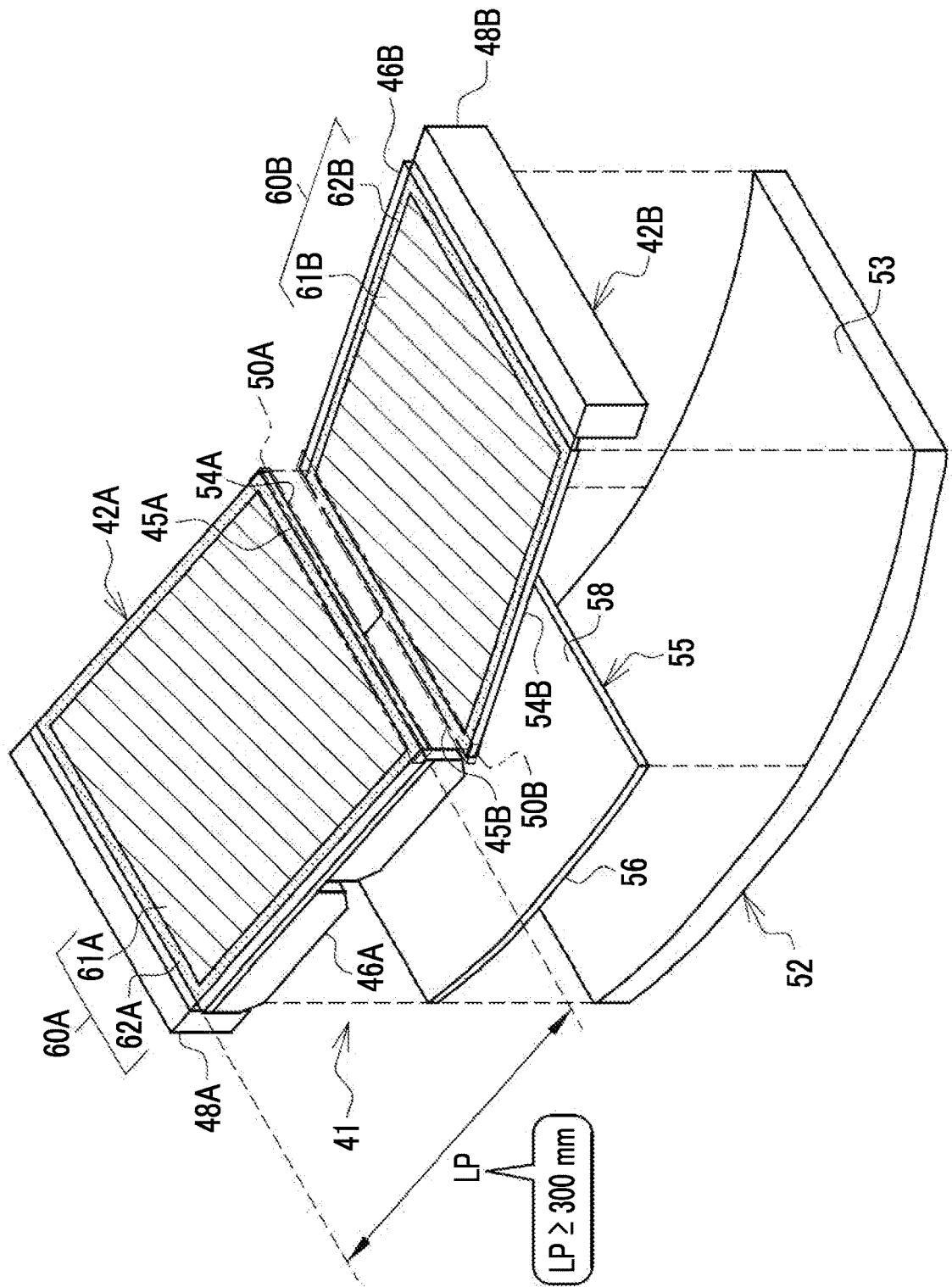
FIG. 8 is an exploded perspective view illustrating two sensor panels, a spacer, and a support table.
Figure 9:
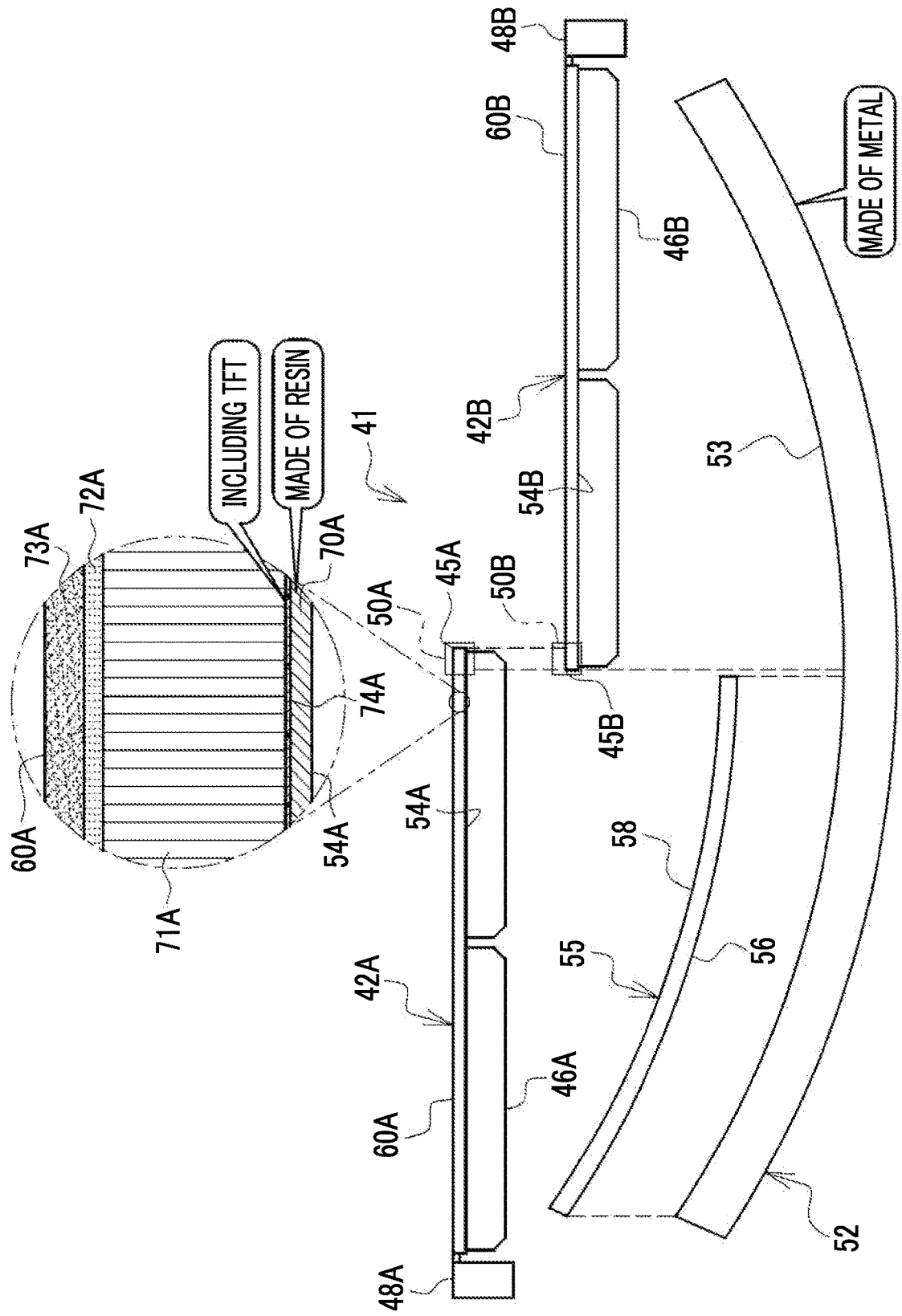
FIG. 9 is an exploded plan view illustrating the two sensor panels, the spacer, and the support table.

For example, as illustrated in FIGS. 8 and 9, in the sensor panels 42A and 42B, an end portion 50A on the side 45A and an end portion 50B on the side 45B are disposed so as to overlap each other in a thickness direction in a state in which the sides 45A and 45B are parallel to each other. The sensor panel 42A and the sensor panel 42B are fixed in the end portions 50A and 50B. The sensor panel 42A and the sensor panel 42B are fixed with, for example, a double-sided tape that is partially attached to the end portion 50B or an adhesive that is partially applied or mask-printed onto the end portion 50B. The sensor panels 42A and 42B are disposed in the order of the sensor panel 42A and the sensor panel 42B as viewed from the radiation source 20. That is, the sensor panel 42A is disposed closer to the incident side of the radiation R than the sensor panel 42B in the thickness direction. Further, the end portion 50A is an example of a "first end portion" according to the technology of the present disclosure, and the end portion 50B is an example of a "second end portion" according to the technology of the present disclosure.

The sensor panel unit 41 is attached to a support table 52. The support table 52 is made of metal (see FIG. 9), such as aluminum or copper, and has an attachment surface 53 that is accurately processed in an arc surface shape (U-shape) which is convex toward the opposite side of the radiation source 20 so as to follow the shape of the frame 18. The sensor panel unit 41 is attached to the attachment surface 53 in a state in which it is curved following the arc surface shape. The radius of the attachment surface 53 is, for example, 500 mm. A member (not illustrated) that is made of, for example, lead and shields the radiation R is attached to a surface of the support table 52 which is opposite to the attachment surface 53. Here, the "U-shape" is a shape in which the entire surface of the sensor panels 42A and 42B including imaging regions 61A and 61B, which will be described below, and the end portions 50A and 50B which overlap each other is curved. Specifically, the "U-shape" means a shape in which both end portions protrude toward one side and both end portions and a central portion are connected by a curved surface.

A spacer 55 is disposed between a first surface 54A of the sensor panel 42A and the attachment surface 53 of the support table 52. The spacer 55 is a thin plate that has substantially the same size as the sensor panel 42A and has an arc surface shape following the shape of the attachment surface 53. The spacer 55 has a thickness corresponding to the distance between the sensor panel 42A and the support table 52. In other words, the spacer 55 has a thickness that fills the step between the sensor panels 42A and 42B in the thickness direction caused by the overlap of the sensor panels 42A and 42B. The radius of the sensor panel 42A is, for example, 500 mm, and the radius of the sensor panel 42B is, for example, 501 mm. In this case, the step between the sensor panels 42A and 42B in the thickness direction is 1 mm, and the thickness of the spacer 55 is also 1 mm.

A first surface 56 of the spacer 55 is entirely attached to the attachment surface 53, and a second surface 58 opposite to the first surface 56 faces the first surface 54A of the sensor panel 42A. The spacer 55 and the attachment surface 53 are fixed, for example, with a double-sided tape that is attached to the attachment surface 53 or an adhesive that is applied or mask-printed onto the attachment surface 53. The first surface 54A of the sensor panel 42A and the second surface 58 of the spacer 55 are in contact with each other, but are not fixed.

A first surface 54B of the sensor panel 42B is fixed to the attachment surface 53. The sensor panel 42B and the attachment surface 53 are fixed, for example, with a double-sided tape that is partially attached to the attachment surface 53 or an adhesive that is partially applied or mask-printed onto the attachment surface 53.

A second surface 60A of the sensor panel 42A which is opposite to the first surface 54A has an imaging region 61A which has a square shape and in which pixels 74A (see FIG. 9) are arranged and a non-imaging region 62A which has a rectangular ring shape and surrounds the imaging region 61A and in which the pixels 74A are not arranged. Similarly, a second surface 60B of the sensor panel 42B which is opposite to the first surface 54B has an imaging region 61B and a non-imaging region 62B. The imaging region 61A is an example of a "first imaging region" according to the technology of the present disclosure, and the imaging region 61B is an example of a "second imaging region" according to the technology of the present disclosure.

In FIG. 9, the sensor panel 42A has a substrate 70A and a scintillator 71A. The scintillator 71A includes, for example, terbium-activated gadolinium oxysulfide (GOS; $Gd_2O_2S$:Tb) and converts the radiation R into visible light. The scintillator 71A is attached to a support 73A through a pressure-sensitive adhesive layer 72A. The support 73A is made of, for example, white polyethylene terephthalate (PET). A rear surface of the substrate 70A is the first surface 54A, and a front surface of the support 73A is the second surface 60A.

The substrate 70A is a flexible thin film sheet that is made of a resin such as polyimide. The substrate 70A includes fine particles of an inorganic oxide that absorbs backscattered rays. Examples of the inorganic oxide include silicon dioxide ($SiO_2$), magnesium oxide (MgO), aluminum oxide (so-called alumina, $Al_2O_3$), and titanium oxide ($TiO_2$). An example of the substrate 70A having the above-mentioned features is XENOMAX (registered trademark) manufactured by Xenomax Japan Co., Ltd.

The substrate 70A is provided with the pixels 74A that detect the visible light converted from the radiation R by the scintillator 71A. As is well known, the pixel 74A includes a light receiving unit that senses the visible light and generates charge and a TFT as a switching element that reads out the charge accumulated in the light receiving unit. A plurality of signal lines for inputting the charge of the light receiving units to the reading circuit board 46A and a plurality of scanning lines for giving on/off signals (scanning signals) from the switching circuit board 48A to the TFTs are provided on the substrate 70A so as to intersect each other in the vertical and horizontal directions. The pixels 74A are disposed at the intersections of the plurality of signal lines and scanning lines. That is, the pixels 74A are two-dimensionally arranged. The pitch of the pixels 74A is, for example, 150 μm. In addition, the pixel 74A may not sense the visible light converted from the radiation R, but may directly sense the radiation R to generate charge.

Figure 10:
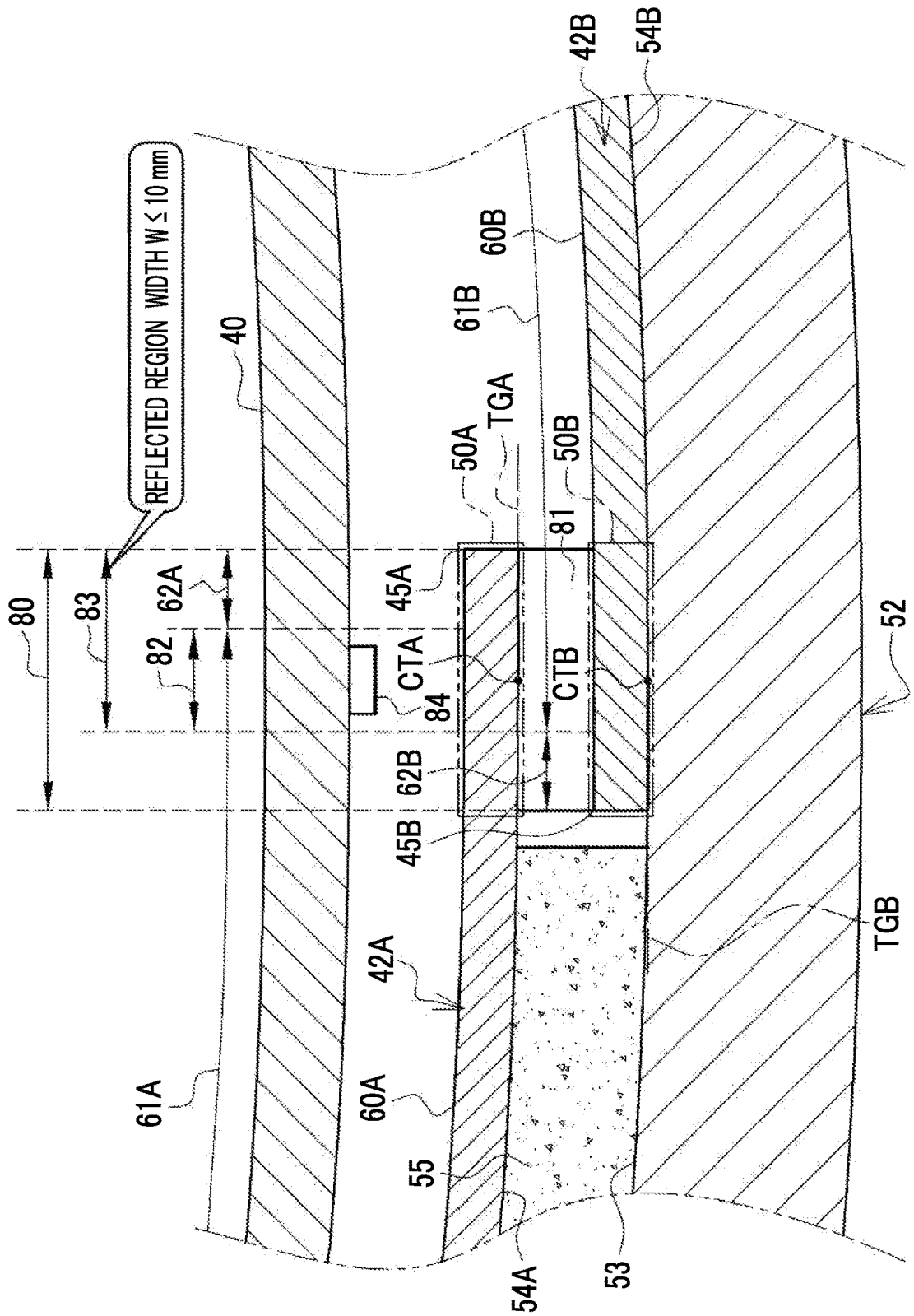
FIG. 10 is a cross-sectional view illustrating the vicinity of an overlap region of end portions of the two sensor panels.

For example, as illustrated in FIG. 10, an overlap region 80 in which the end portion 50A of the sensor panel 42A and the end portion 50B of the sensor panel 42B overlap each other is a region defined by an end of the sensor panel 42A on the side 45A and an end of the sensor panel 42B on the side 45B. The end portion 50A and the end portion 50B are fixed to each other by a fixing member 81 in the overlap region 80. The fixing member 81 is, for example, a double-sided tape or an adhesive as described above. Further, the sensor panel 42B and the support table 52 are also fixed to each other by the fixing member in the overlap region 80, which is not illustrated.

The overlap region 80 is located at the center of the sensor panel unit 41. Therefore, the radiation R is incident (vertically incident) on the overlap region 80 at an irradiation angle of 90°.

The imaging region 61A of the sensor panel 42A and the imaging region 61B of the sensor panel 42B overlap each other in the overlap region 80 in a plan view of the sensor panel unit 41 in the thickness direction. Hereinafter, the region in which the imaging regions 61A and 61B overlap each other is referred to as an overlap imaging region 82.

In the imaging region 61B, a reflected region 83 in which the end portion 50A of the sensor panel 42A is reflected is present in the overlap region 80. In this example, the reflected region 83 is a region including the non-imaging region 62A and the overlap imaging region 82. A width W of the reflected region 83 is equal to or less than 10 mm (W≤10 mm).

The end portion 50A of the sensor panel 42A and the end portion 50B of the sensor panel 42B are parallel to each other. Specifically, a tangent line TGA between the sensor panel 42A and the sensor panel 42B and a tangent line TGB between the sensor panel 42B and the support table 52 in the overlap region 80 are parallel to each other. The tangent line TGA is a point in a fixing region of the fixing member 81 to the sensor panel 42A, and a point intersecting a center line of the overlap region 80 is referred to as a contact point CTA. The tangent line TGB is a point in a fixing region of a fixing member (not illustrated), which fixes the sensor panel 42B and the support table 52, to the sensor panel 42B, and a point intersecting the center line of the overlap region 80 is referred to as a contact point CTB.

Two square markers 84 are attached to the rear surface of the housing 40. The attachment positions of the two markers 84 are both end portions of the overlap imaging region 82 on the sides 43A and 43B and the sides 44A and 44B and are preset positions in the overlap imaging region 82. Therefore, the markers 84 are reflected in both the sensor panel 42A and the sensor panel 42B. The two markers 84 make it possible to detect not only the deviation of the sensor panels 42A and 42B from the set position in the plane direction but also the inclination of the sensor panels 42A and 42B with respect to the set position. In addition, the markers 84 may be attachably and detachably attached to the housing 40.

Figure 11:
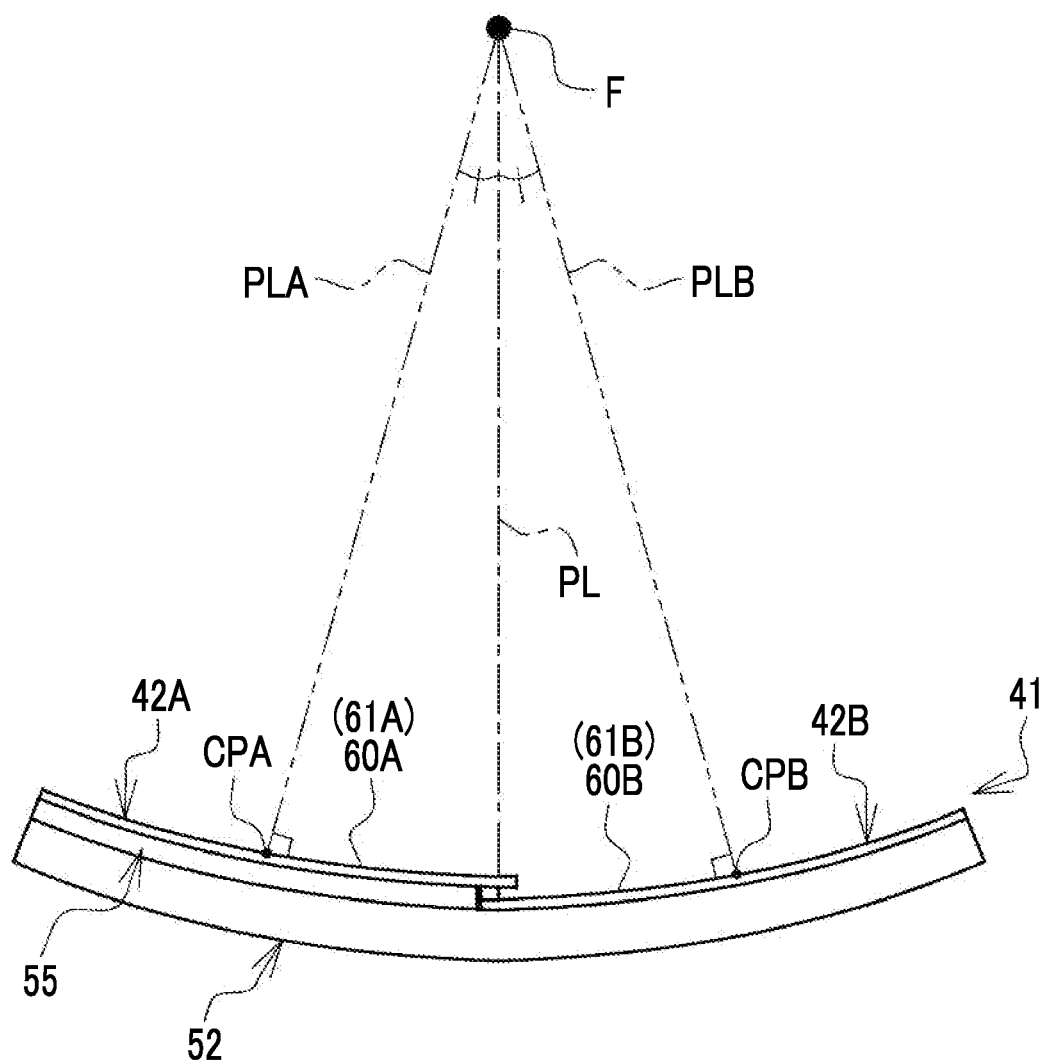
FIG. 11 is a diagram illustrating a positional relationship between a focus of the radiation and the sensor panels.

For example, as illustrated in FIG. 11, a perpendicular line PLA drawn from the focus F of the radiation R to the second surface 60A of the sensor panel 42A intersects a center point CPA of the imaging region 61A. Similarly, a perpendicular line PLB drawn from the focus F to the second surface 60B of the sensor panel 42B intersects a center point CPB of the imaging region 61B. The perpendicular lines PLA and PLB have the same length and have the same angle with respect to a perpendicular line PL drawn from the focus F to a center point of the sensor panel unit 41. Therefore, the centers of the arc surfaces (centers of curvature) of the sensor panels 42A and 42B are aligned with each other at the focus F. That is, the centers of curvature of the sensor panels 42A and 42B are located at the same position. Further, the sensor panels 42A and 42B are substantially mirror-symmetric with respect to the perpendicular line PL. Furthermore, the term "same" in the "same position" indicates "same" including an error (for example, an error of about 1% to 10%) that is generally allowed in the technical field to which the technology of the present disclosure belongs and does not depart from the gist of the technology of the present disclosure, in addition to exact "same".

Figure 12:
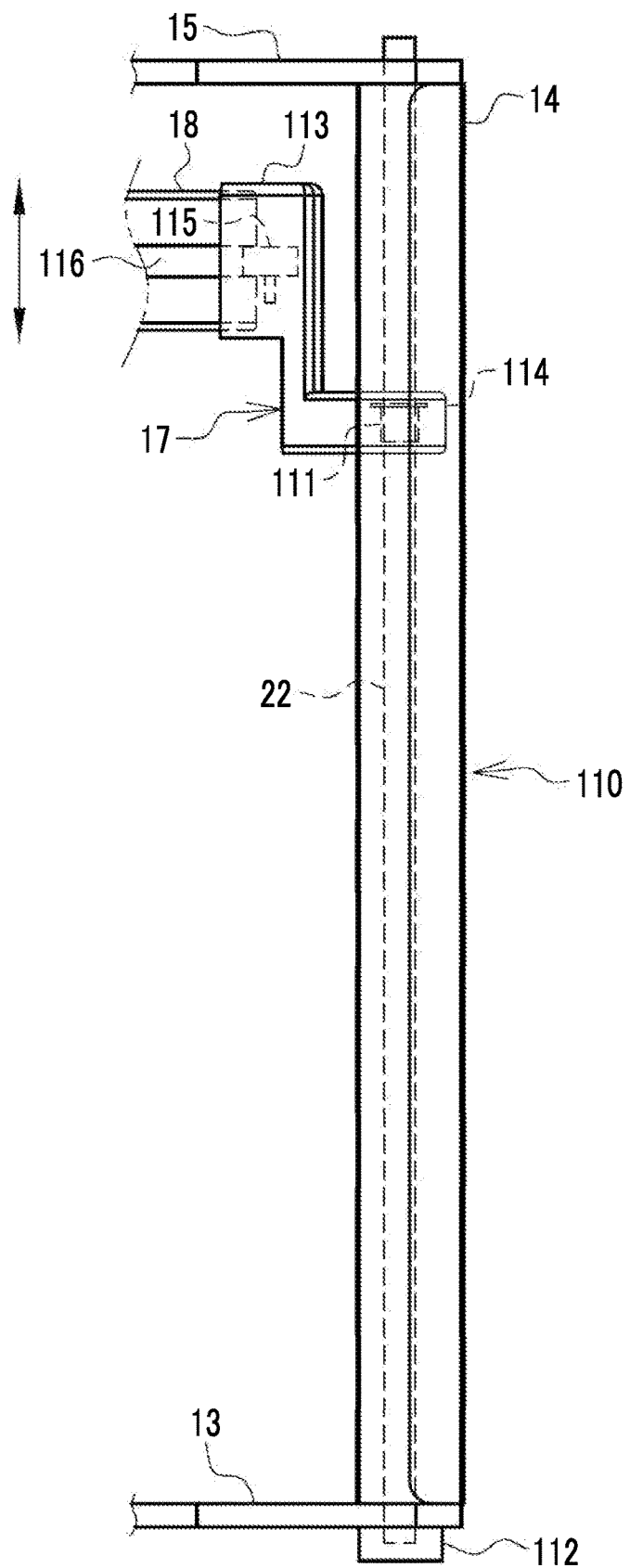
FIG. 12 is a diagram illustrating an elevating mechanism.

For example, as illustrated in FIG. 12, an elevating mechanism 110 that raises and lowers the connection member 17 and thus the frame 18 in the vertical direction is a ball screw mechanism including, for example, the screw shaft 22, a nut 111 that has a ball provided therein and is engaged with the screw shaft 22, an elevating motor 112 that rotates the screw shaft 22. The elevating motor 112 is attached to the rear surface of the stage 13. The height position of the frame 18 is determined from the rotation direction and rotation speed of the elevating motor 112.

The connection member 17 has a first connection portion 113 that is connected to the frame 18 and a second connection portion 114 that is connected to the column 14. The first connection portion 113 protrudes toward the frame 18, and the second connection portion 114 protrudes toward the column 14. The connection member 17 has a Z-shape as a whole. A bearing 115 is provided in the first connection portion 113. The bearing 115 is fitted to a guide groove 116 (see also FIG. 1 and the like) that is formed over the entire circumference of the frame 18. The bearing 115 rolls as the frame 18 is rotated. The nut 111 is provided in the second connection portion 114.

Figure 13:
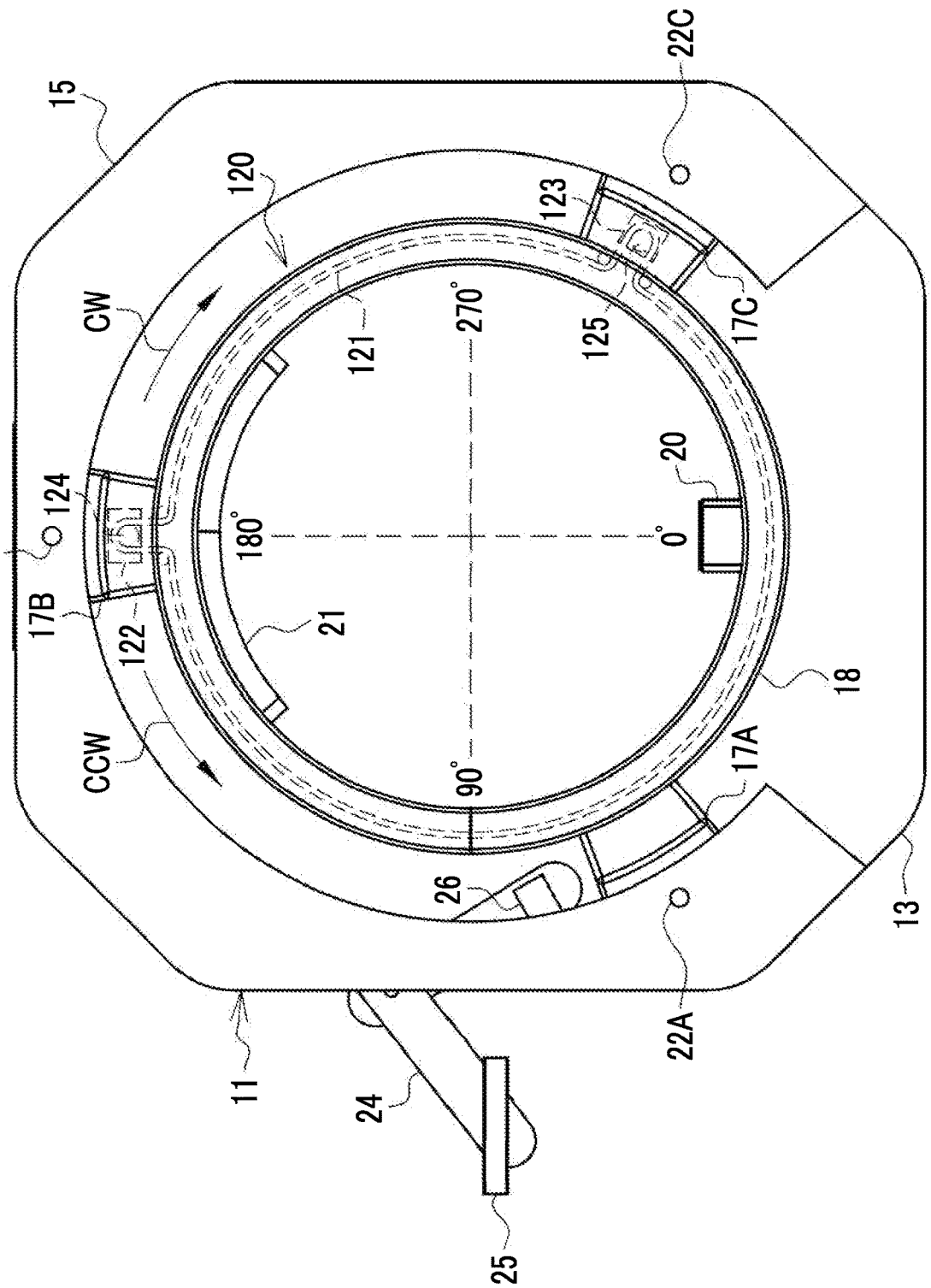
FIG. 13 is a diagram illustrating a rotation mechanism.

For example, as illustrated in FIG. 13, a rotation mechanism 120 that rotates the frame 18 around the subject S includes a rotation belt 121 that is wound around the entire circumference of the frame 18, a rotary motor 122, a potentiometer 123, and the like. The rotary motor 122 is provided in the connection member 17B and is connected to a portion of the rotation belt 121 drawn out from the frame 18 through a pulley 124. The rotary motor 122 is driven to rotate the frame 18 in a clockwise (right-hand rotation) direction CW and a counterclockwise (left-hand rotation) direction CCW. The potentiometer 123 is provided in the connection member 17C and is connected to a portion of the rotation belt 121 drawn out from the frame 18 through the pulley 125. The potentiometer 123 has a variable resistor whose resistance value is changed depending on the rotation position of the frame 18 and outputs a voltage signal corresponding to the rotation position of the frame 18. The rotation position of the frame 18 is determined by the voltage signal from the potentiometer 123.

Figure 14:
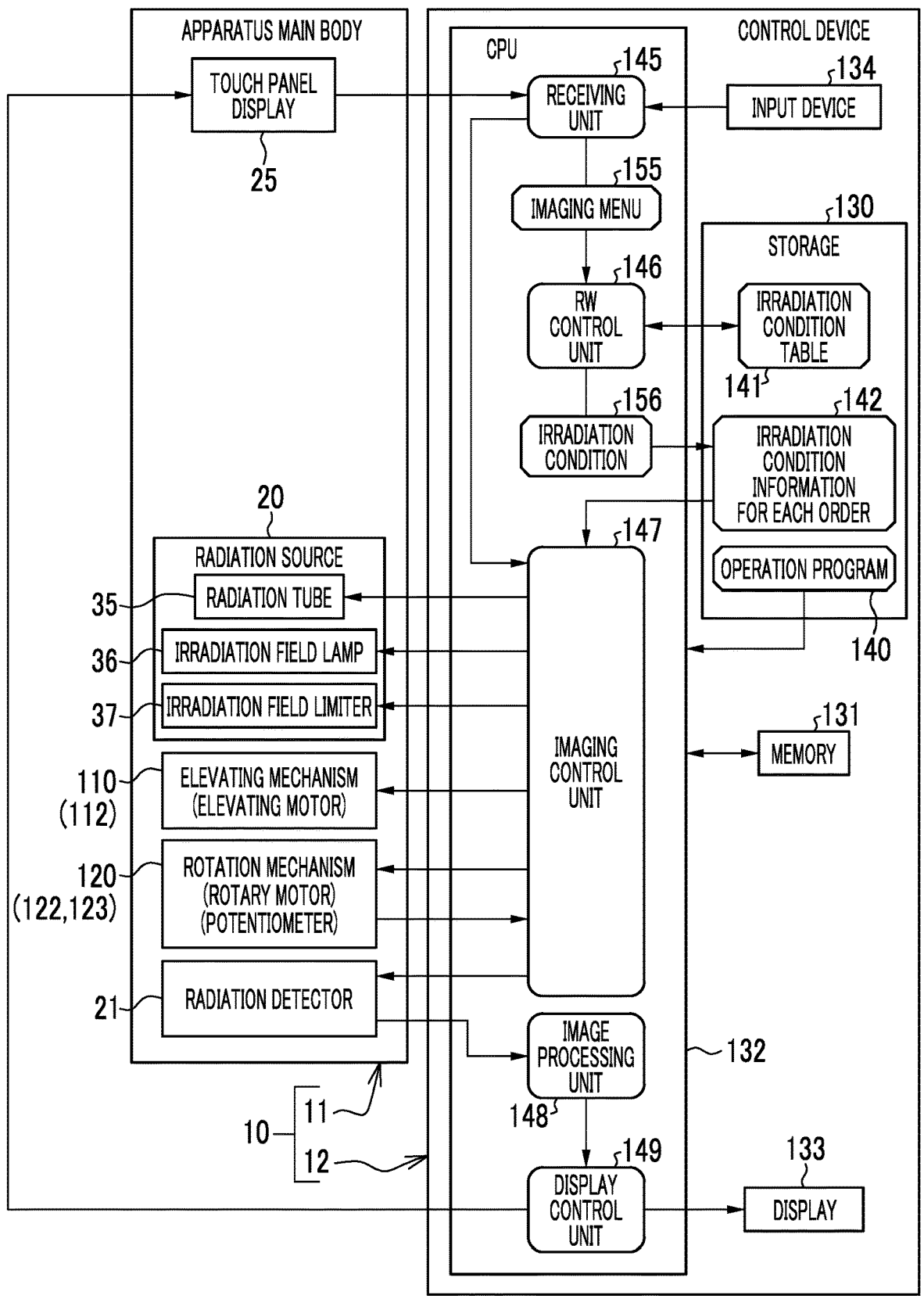
FIG. 14 is a block diagram illustrating a processing unit of a CPU of a control device.

For example, as illustrated in FIG. 14, a computer constituting the control device 12 comprises a storage 130, a memory 131, a central processing unit (CPU) 132, a display 133, an input device 134, and the like.

The storage 130 is a hard disk drive that is provided in the computer constituting the control device 12 or is connected to the computer through a cable or a network. Alternatively, the storage 130 is a disk array in which a plurality of hard disk drives are connected. The storage 130 stores, for example, a control program, such as an operating system, various application programs, and various kinds of data associated with these programs. In addition, a solid state drive may be used instead of the hard disk drive.

The memory 131 is a work memory that is used by the CPU 132 to perform processes. The CPU 132 loads the program stored in the storage 130 to the memory 131 and performs the process corresponding to the program. Therefore, the CPU 132 controls the overall operation of each unit of the computer. The CPU 132 is an example of a "processor" according to the technology of the present disclosure. In addition, the memory 131 may be provided in the CPU 132.

The display 133 displays various screens. The various screens have operation functions by a graphical user interface (GUI). The computer constituting the control device 12 receives operation instructions input from the input device 134 through various screens. The input device 134 is, for example, a keyboard, a mouse, a touch panel, and a microphone for voice input.

An operation program 140 is stored in the storage 130. The operation program 140 is an application program for causing the computer to function as the control device 12. The storage 130 stores, for example, an irradiation condition table 141 and irradiation condition information 142 for each order, in addition to the operation program 140.

In a case in which the operation program 140 is started, the CPU 132 of the control device 12 functions as a receiving unit 145, a read and write (hereinafter, abbreviated to RW) control unit 146, an imaging control unit 147, an image processing unit 148, and a display control unit 149 in cooperation with, for example, the memory 131.

The receiving unit 145 receives various operation instructions input by the operator through the touch panel display 25 of the apparatus main body 11 and the input device 134. For example, the receiving unit 145 receives an imaging menu 155. The receiving unit 145 outputs the imaging menu 155 to the RW control unit 146.

The RW control unit 146 receives the imaging menu 155 from the receiving unit 145. The RW control unit 146 reads out irradiation conditions 156 of the radiation R which correspond to the received imaging menu 155 from the irradiation condition table 141. The RW control unit 146 writes the irradiation conditions 156 read from the irradiation condition table 141 to the irradiation condition information 142 for each order.

The imaging control unit 147 controls the operation of the radiation source 20 (the radiation tube 35, the irradiation field lamp 36, and the irradiation field limiter 37), the elevating mechanism 110 (elevating motor 112), the rotation mechanism 120 (the rotary motor 122 and the potentiometer 123), and the radiation detector 21. The imaging control unit 147 reads out the irradiation conditions 156 from the irradiation condition information 142 for each order. The imaging control unit 147 drives the irradiation field limiter 37 according to the irradiation conditions 156 to adjust the irradiation field. Further, the imaging control unit 147 drives the radiation tube 35 according to the irradiation conditions 156 such that the radiation R is emitted from the radiation tube 35. The imaging control unit 147 outputs a radiographic image, which has been formed by the emission of the radiation R and detected by the radiation detector 21, from the radiation detector 21 to the image processing unit 148. Hereinafter, the radiographic image detected by the radiation detector 21 is referred to as a projection image PI (see FIG. 18).

The image processing unit 148 acquires the projection image PI from the radiation detector 21. The image processing unit 148 performs various types of image processing on the projection image PI. Further, the image processing unit 148 performs a reconstruction process on a plurality of projection images PI subjected to the image processing to generate a tomographic image TI. The image processing unit 148 outputs the projection image PI or the tomographic image TI subjected to the image processing to the display control unit 149. In addition, the image processing unit 148 may perform a process of correcting the positional deviation of the pixels 74 caused by the thermal expansion and contraction of the sensor panel 42.

The display control unit 149 controls the display of various kinds of information on the touch panel display 25 and the display 133. The display control unit 149 receives the projection image PI or the tomographic image TI from the image processing unit 148. The display control unit 149 displays the projection image PI or the tomographic image TI on the touch panel display 25 and the display 133.

The imaging menu 155 includes, for example, imaging order identification data (ID) and an imaging procedure (see FIG. 15). The imaging order ID is identification information of the imaging order issued by a doctor who performs a medical examination using the tomographic image TI. The imaging procedure includes the posture of the subject S in a standing or sitting position, an imaging part, such as the head, the neck, or the spine, and the attributes of the subject S such as an adult male and an adult female.

The imaging order is transmitted from a radiology information system (RIS) (not illustrated) to the control device 12. The control device 12 displays a list of imaging orders on the display 133 under the control of the display control unit 149. The operator browses the list of imaging orders and checks the content of the list. Then, the control device 12 displays the imaging menu 155 corresponding to the imaging order on the display 133 such that it can be set. The operator operates the input device 134 to select the imaging menu 155 corresponding to the imaging order and to input the imaging menu 155.

For example, as illustrated in FIG. 15, the irradiation conditions 156 are registered in the irradiation condition table 141 for each imaging procedure. The irradiation conditions 156 include a tube voltage and a tube current applied to the radiation tube 35 and the irradiation time of the radiation R. In addition, the irradiation conditions 156 include the size of the irradiation field, which is not illustrated. The operator can finely adjust the irradiation conditions 156 by hand. Further, instead of the tube current and the irradiation time, a tube current-irradiation time product, that is, a so-called mAs value may be set as the irradiation condition 156.

A scout imaging position and a main imaging start position are also registered in the irradiation condition table 141 for each imaging procedure, which is not illustrated. The scout imaging position is a set of the height position and the rotation position of the frame 18 in scout imaging. The height position indicates the height of the frame 18 in a case in which the surface of the stage 13 is 0 cm. The rotation position is, for example, a position where the radiation source 20 faces the subject S, that is, a position of 0°. Alternatively, the rotation position may be a position of 90° where the radiation source 20 faces the right side surface of the subject S or a position of 270° where the radiation source 20 faces the left side surface of the subject S.

Here, the scout imaging is preliminary radiography that is performed to confirm the positioning of the subject S before the main imaging that captures a plurality of projection images PI at a predetermined angle to generate the tomographic image TI. In the scout imaging, the frame 18 is located at the height position and the rotation position registered in the irradiation condition table 141, and the radiation R is emitted with a lower dose than that in the main imaging to obtain one projection image PI. Hereinafter, the projection image PI obtained by the scout imaging is referred to as a scout image SI (see FIG. 16). The scout image SI is an example of a "confirmation image" according to the technology of the present disclosure.

The main imaging start position is the rotation start position of the frame 18 in the main imaging. The main imaging start position is, for example, a position of 0°. Alternatively, the main imaging start position may be a position of 90°.

The irradiation conditions 156, the scout imaging position, and the main imaging start position are registered for each imaging order ID in the irradiation condition information 142 for each order, which is not illustrated. The imaging control unit 147 reads out the irradiation conditions 156, the scout imaging position, and the main imaging start position corresponding to the imaging order ID of the next imaging from the irradiation condition information 142 for each order and controls the operation of each unit on the basis of the read-out irradiation condition 156, scout imaging position, and main imaging start position.

In a case in which the subject S is guided into the apparatus main body 11, the frame 18 is moved to a retracted height position by the elevating mechanism 110 and is rotated to a position of 60° by the rotation mechanism 120 under the control of the imaging control unit 147. The retracted height position is set on the upper end side of the column 14. Specifically, the retracted height position is the position of the highest point in the elevation range of the frame 18. In this example, the position of the highest point in the elevation range of the frame 18 is the position of substantially the upper end of the column 14 and is the position where the second connection portion 114 of the connection member 17 comes into contact with the rear surface of the top plate 15. The position of 60° is a position where the entire radiation source 20 overlaps the column 14A. The operator guides the subject S into the apparatus main body 11 in this state through a space between the columns 14A and 14C as an entrance and positions the subject S.

After positioning the subject S in the apparatus main body 11, the operator stays at the installation position of the apparatus main body 11 and operates the touch panel display 25 to move the frame 18 to the height position registered in the irradiation condition table 141 and to rotate the frame 18 to the position of 0°. Then, the operator operates the touch panel display 25 to turn on the irradiation field lamp 36 and to irradiate the irradiation field with visible light, in order to confirm the irradiation field of the radiation R.

The operator visually recognizes the visible light from the irradiation field lamp 36 and determines whether the height position of the frame 18 and the positioning of the subject S are appropriate for imaging. In a case in which it is determined that the height position of the frame 18 and the positioning of the subject S are not appropriate for imaging, the operator operates the touch panel display 25 to adjust the height position of the frame 18 or to reposition the subject S. In a case in which it is determined that the height position of the frame 18 and the positioning of the subject S are appropriate for imaging, the operator operates the touch panel display 25 to turn off the irradiation field lamp 36.

Figure 16:
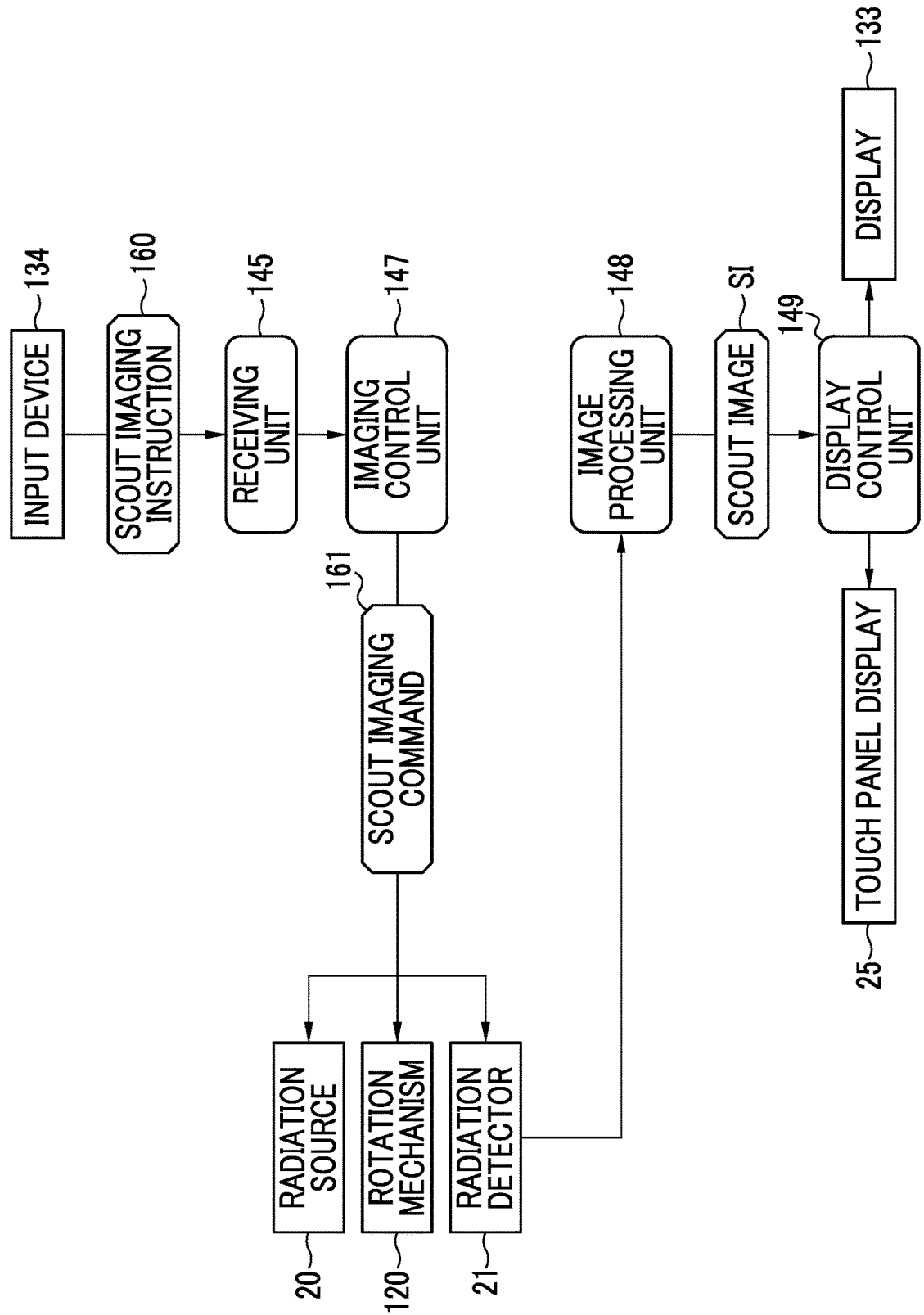
FIG. 16 is a diagram illustrating an outline of a process in a case in which a scout imaging instruction for performing scout imaging is input.

For example, as illustrated in FIG. 16, after confirming the irradiation field of the radiation R, the operator moves to the installation position of the control device 12 and operates the input device 134 to input a scout imaging instruction 160 for performing the scout imaging. The receiving unit 145 receives the scout imaging instruction 160 and outputs the instruction to the imaging control unit 147. The imaging control unit 147 outputs a scout imaging command 161 corresponding to the scout imaging instruction 160 to the radiation source 20, the radiation detector 21, and the rotation mechanism 120.

The content of the scout imaging command 161 is that the height position at the time of confirming the irradiation field of the radiation R is maintained and the frame 18 is rotated to the rotation position which is the scout imaging position registered in the irradiation condition table 141. Further, the content of the scout imaging command 161 is that the scout imaging is performed at the height position at the time of confirming the irradiation field of the radiation R and the rotation position which is the scout imaging position registered in the irradiation condition table 141. The rotation mechanism 120 drives the rotary motor 122 to rotate the rotation belt 121, thereby rotating the frame 18 to the rotation position which is the scout imaging position registered in the irradiation condition table 141.

The radiation source 20 drives the radiation tube 35 to irradiate the subject S with the radiation R for scout imaging. The radiation detector 21 detects the radiation R transmitted through the subject S to obtain the projection image PI. The radiation detector 21 outputs the projection image PI to the image processing unit 148.

The image processing unit 148 performs various types of image processing on the projection image PI from the radiation detector 21 to obtain the scout image SI. The image processing unit 148 outputs the scout image SI to the display control unit 149. The display control unit 149 displays the scout image SI on the touch panel display 25 and the display 133.

The operator browses the scout image SI on the display 133 and determines whether the height position of the frame 18 and the positioning of the subject S are appropriate for imaging. In a case in which it is determined that the height position of the frame 18 and the positioning of the subject S are not appropriate for imaging from the scout image SI, the operator returns to the installation position of the apparatus main body 11 and turns on the irradiation field lamp 36 again to adjust the height position of the frame 18 or to reposition the subject S.

Figure 17:
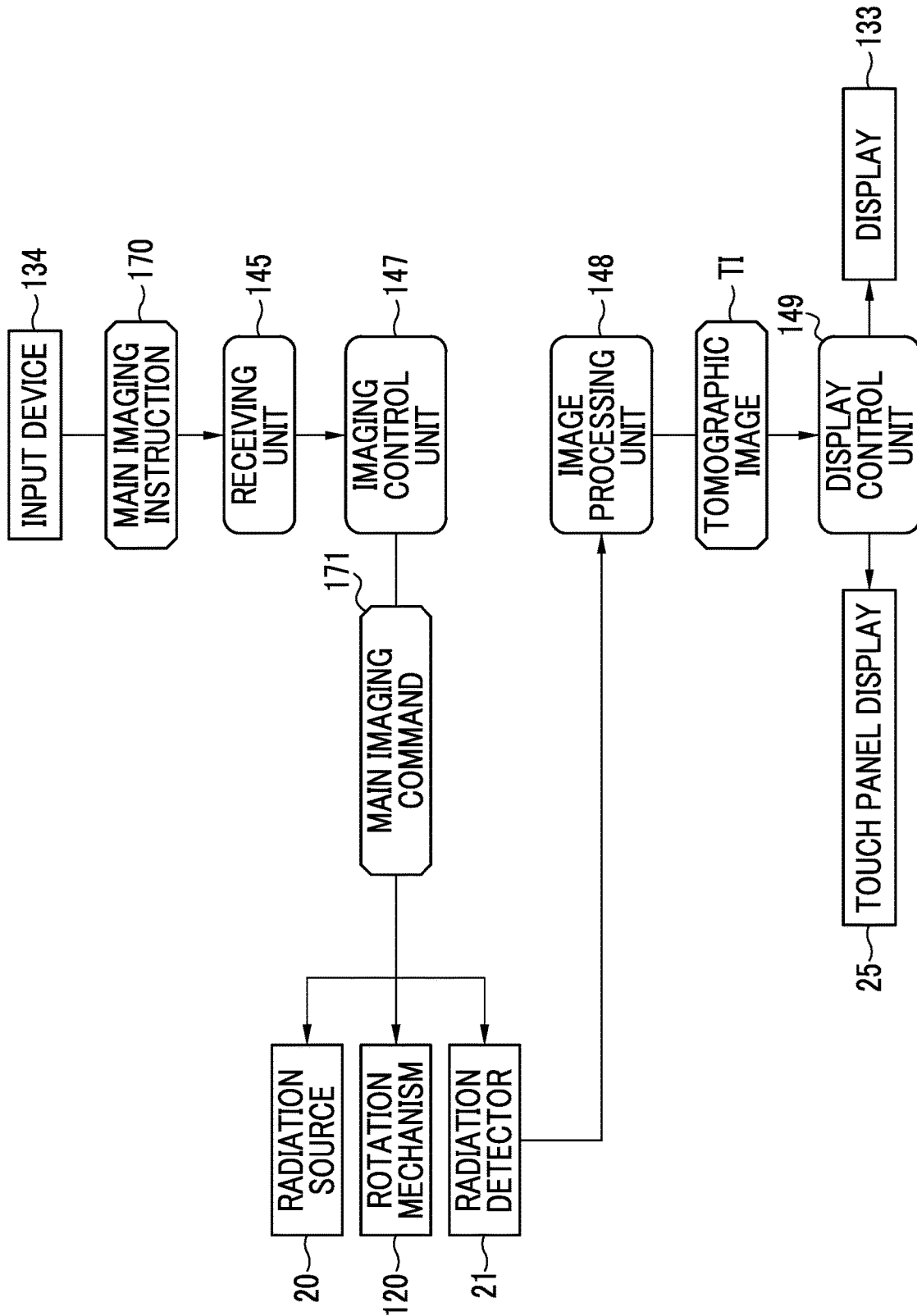
FIG. 17 is a diagram illustrating an outline of a process in a case in which a main imaging instruction for performing main imaging is input.

For example, as illustrated in FIG. 17, in a case in which it is determined that the height position of the frame 18 and the positioning of the subject S are appropriate for imaging from the scout image SI, the operator operates the input device 134 to input a main imaging instruction 170 for performing the main imaging. The receiving unit 145 receives the main imaging instruction 170 and outputs the instruction to the imaging control unit 147. The imaging control unit 147 outputs a main imaging command 171 corresponding to the main imaging instruction 170 to the radiation source 20, the radiation detector 21, and the rotation mechanism 120.

The content of the main imaging command 171 is that the height position at the time of the end of the scout imaging is maintained and the frame 18 is rotated to the main imaging start position and is then rotated to a main imaging end position in the counterclockwise direction CCW. Further, the content of the main imaging command 171 is that the main imaging is performed while the frame 18 is rotated from the main imaging start position to the main imaging end position. The rotation mechanism 120 drives the rotary motor 122 to rotate the rotation belt 121 such that the frame 18 is first rotated to the main imaging start position. Then, the rotation mechanism 120 rotates the frame 18 to the main imaging end position in the counterclockwise direction CCW. In this example, the main imaging end position is a position that is rotated by 225° in the counterclockwise direction CCW from the main imaging start position. In a case in which the main imaging start position is a position of 0°, the main imaging end position is a position of 135° that is rotated by 225° in the counterclockwise direction CCW from the position of 0°. Further, in a case in which the main imaging start position is 90°, the main imaging end position is a position of 225°. In a case in which the main imaging start position is 180°, the main imaging end position is a position of 315°.

The radiation source 20 drives the radiation tube 35 at a predetermined angle to irradiate the subject S with the radiation R for main imaging according to the irradiation conditions 156 at a predetermined angle. The radiation detector 21 detects the radiation R transmitted through the subject S at a predetermined angle to obtain a plurality of projection images PI. The radiation detector 21 sequentially outputs the plurality of projection images PI to the image processing unit 148.

The image processing unit 148 performs a reconstruction process on the plurality of projection images PI from the radiation detector 21 to obtain the tomographic image TI. The image processing unit 148 outputs the tomographic image TI to the display control unit 149. The display control unit 149 displays the tomographic image TI on the touch panel display 25 and the display 133.

The operator browses the tomographic image TI on the display 133 and determines whether or not the tomographic image TI needs to be re-captured. In a case in which it is determined that the tomographic image TI needs to be re-captured, the operator operates the input device 134 to re-input the main imaging instruction 170.

In a case in which it is determined that the tomographic image TI does not need to be re-captured, the operator operates the input device 134 to return the frame 18 to the retracted height position. Further, the frame 18 is rotated in the clockwise direction CW from the imaging end position and is returned to the position of 60°. Then, the operator retracts the subject S from the inside of the apparatus main body 11.

Figure 18:
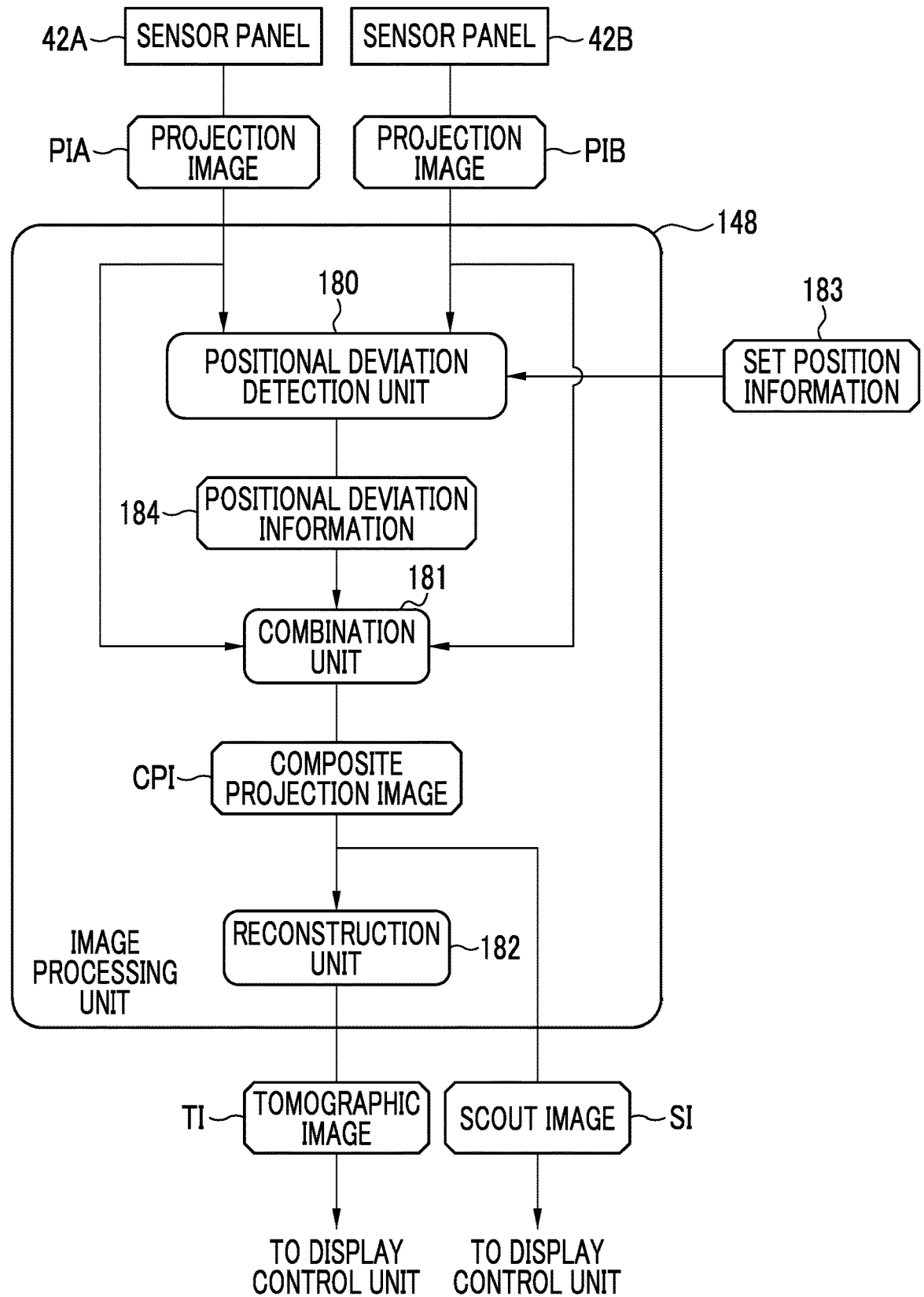
FIG. 18 is a block diagram illustrating a detailed configuration of an image processing unit.

For example, as illustrated in FIG. 18, the image processing unit 148 has a positional deviation detection unit 180, a combination unit 181, and a reconstruction unit 182. The positional deviation detection unit 180 does not operate in a case in which the scout image SI is generated and operates only in a case in which the tomographic image TI is generated. A projection image PIA from the sensor panel 42A and a projection image PIB from the sensor panel 42B are input to the positional deviation detection unit 180 and the combination unit 181. Set position information 183 indicating the set position of the marker 84 is also input to the positional deviation detection unit 180. Specifically, the set position information 183 is the coordinates of the position of the center of an image 190A (see FIG. 19) of the marker 84 in the projection image PIA in a case in which the sensor panel 42A is disposed without any positional deviation. In addition, the set position information 183 is the coordinates of the position of the center of the image of the marker 84 in the projection image PIB in a case in which the sensor panel 42B is disposed without any positional deviation.

Figure 19:
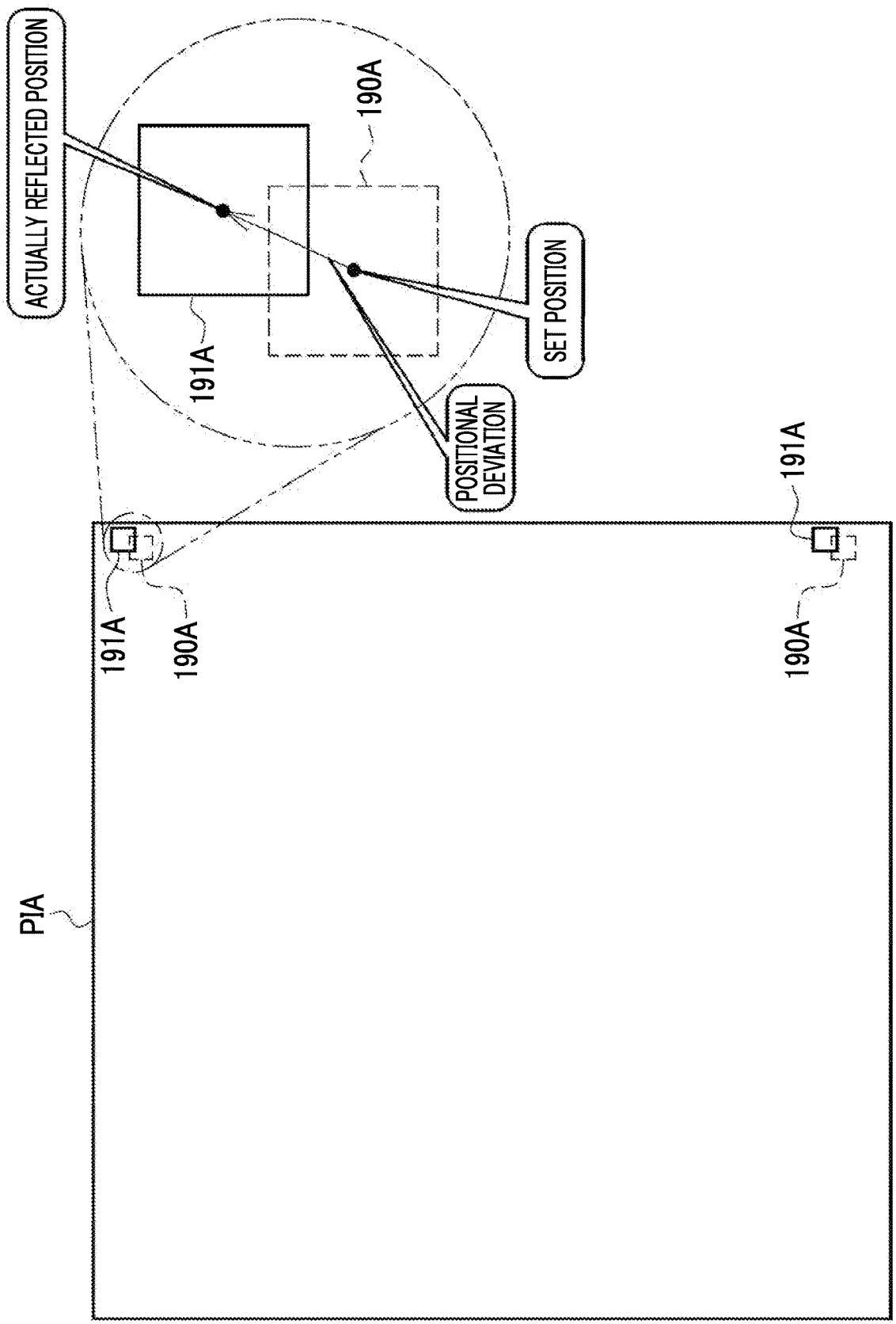
FIG. 19 is a diagram illustrating the positional deviation of the sensor panels.

For example, as illustrated in FIG. 19, the positional deviation detection unit 180 detects a position (hereinafter, referred to as a reflected position) where the marker 84 is actually reflected in the projection image PIA. Specifically, the reflected position is the coordinates of the position of the center of an image 191A of the marker 84 reflected in the projection image PIA. The positional deviation detection unit 180 detects the positional deviation of the sensor panel 42A for each of the two markers 84 on the basis of the detected reflected position and the set position of the marker 84 indicated by the set position information 183. The positional deviation of the sensor panel 42A is represented by the difference between the coordinates of the position of the center of the image 190A of the marker 84 in the projection image PIA in a case in which the sensor panel 42A is disposed without any positional deviation and the coordinates of the position of the center of the image 191A of the marker 84 reflected in the projection image PIA. In addition, the positional deviation detection unit 180 performs the same process on the projection image PIB to detect the positional deviation of the sensor panel 42B, which is not illustrated. The detection of the positional deviation of the sensor panels 42A and 42B by the positional deviation detection unit 180 is an example of a "process related to image quality" according to the technology of the present disclosure.

In FIG. 18, the positional deviation detection unit 180 outputs positional deviation information 184 indicating the positional deviation of the sensor panels 42A and 42B to the combination unit 181. In a case in which the tomographic image TI is generated, the combination unit 181 corrects the positional deviation indicated by the positional deviation information 184 and combines the projection images PIA and PIB to obtain a composite projection image CPI. The combination unit 181 outputs the composite projection image CPI to the reconstruction unit 182. The reconstruction unit 182 generates the tomographic image TI on the basis of the composite projection image CPI and outputs the generated tomographic image TI to the display control unit 149. In addition, the process of correcting the positional deviation indicated by the positional deviation information 184 is an example of the "process related to image quality" according to the technology of the present disclosure.

On the other hand, in a case in which the scout image SI is generated, the positional deviation detection unit 180 does not operate as described above. Therefore, the positional deviation information 184 is not input from the positional deviation detection unit 180 to the combination unit 181. Therefore, the combination unit 181 combines the projection images PIA and PIB, without correcting the positional deviation, to obtain the composite projection image CPI. The combination unit 181 outputs the composite projection image CPI as the scout image SI to the display control unit 149.

Figure 20:
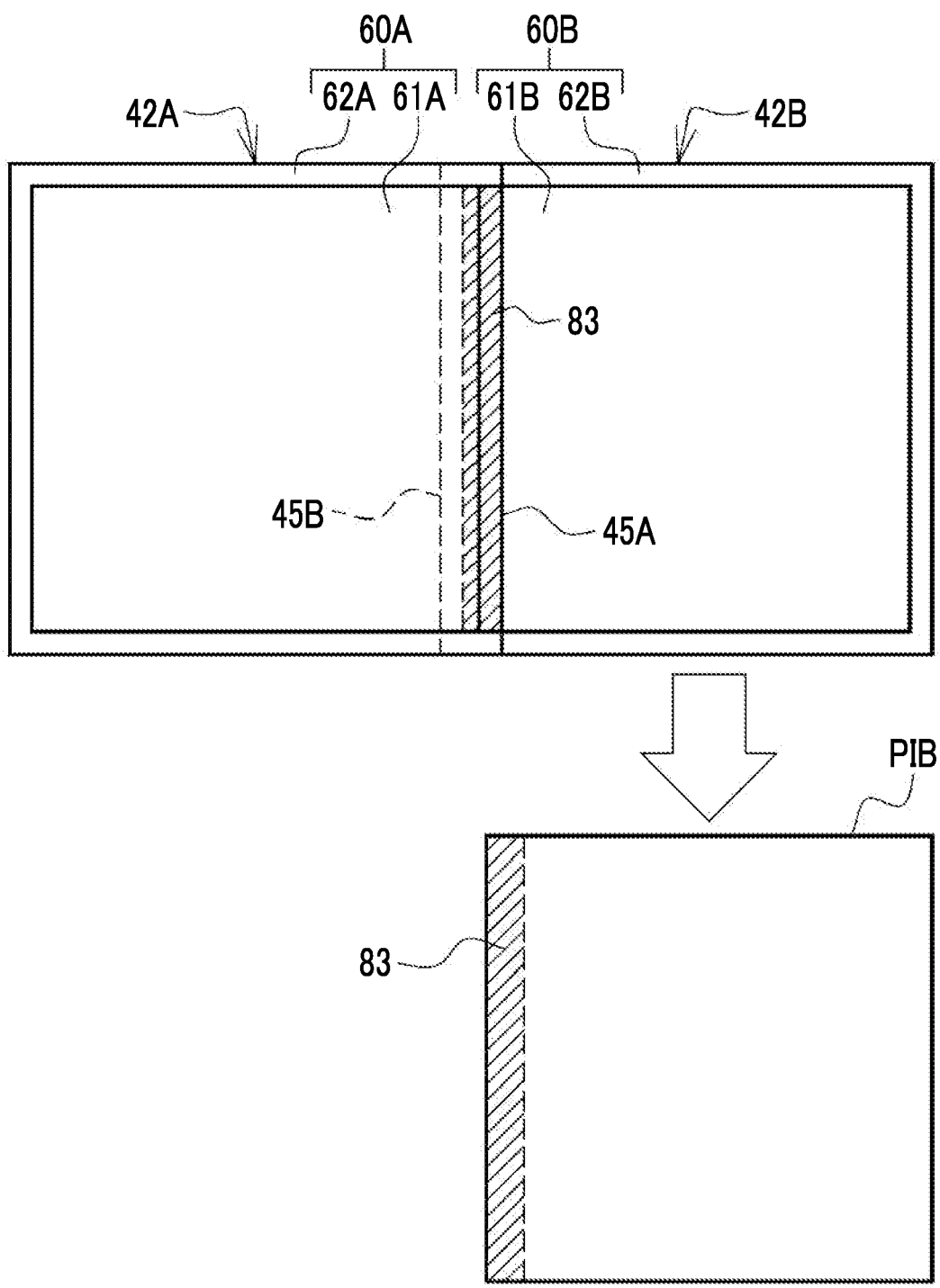
FIG. 20 is a diagram illustrating a reflected region in a case in which the sensor panels are disposed without any positional deviation.
Figure 21:
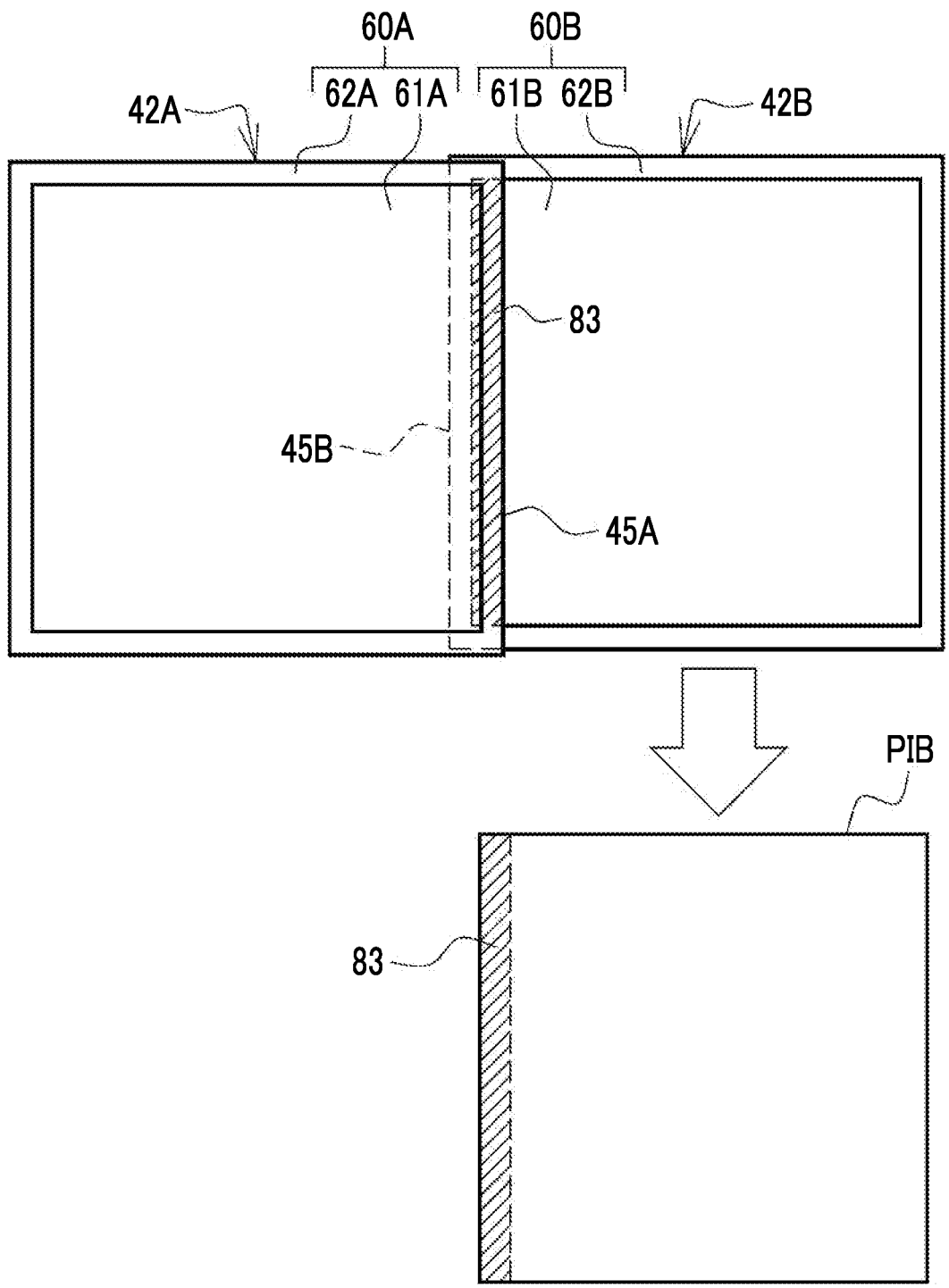
FIG. 21 is a diagram illustrating the reflected region in a case in which the positions of the sensor panels deviate from each other.

FIG. 20 illustrates the reflected region 83 in a case in which the sensor panels 42A and 42B are disposed without any positional deviation. On the other hand, FIG. 21 illustrates the reflected region 83 in a case in which the position of the sensor panel 42B deviates from the position of the sensor panel 42A. As described above, the reflected region 83 changes depending on a relative positional relationship between the sensor panels 42A and 42B. In a case in which the tomographic image TI is generated, the combination unit 181 checks the relative positional relationship between the sensor panels 42A and 42B from the positional deviation information 184 and specifies the reflected region 83. In addition, a process of specifying the reflected region 83 is an example of the "process related to image quality" according to the technology of the present disclosure.

Figure 22:
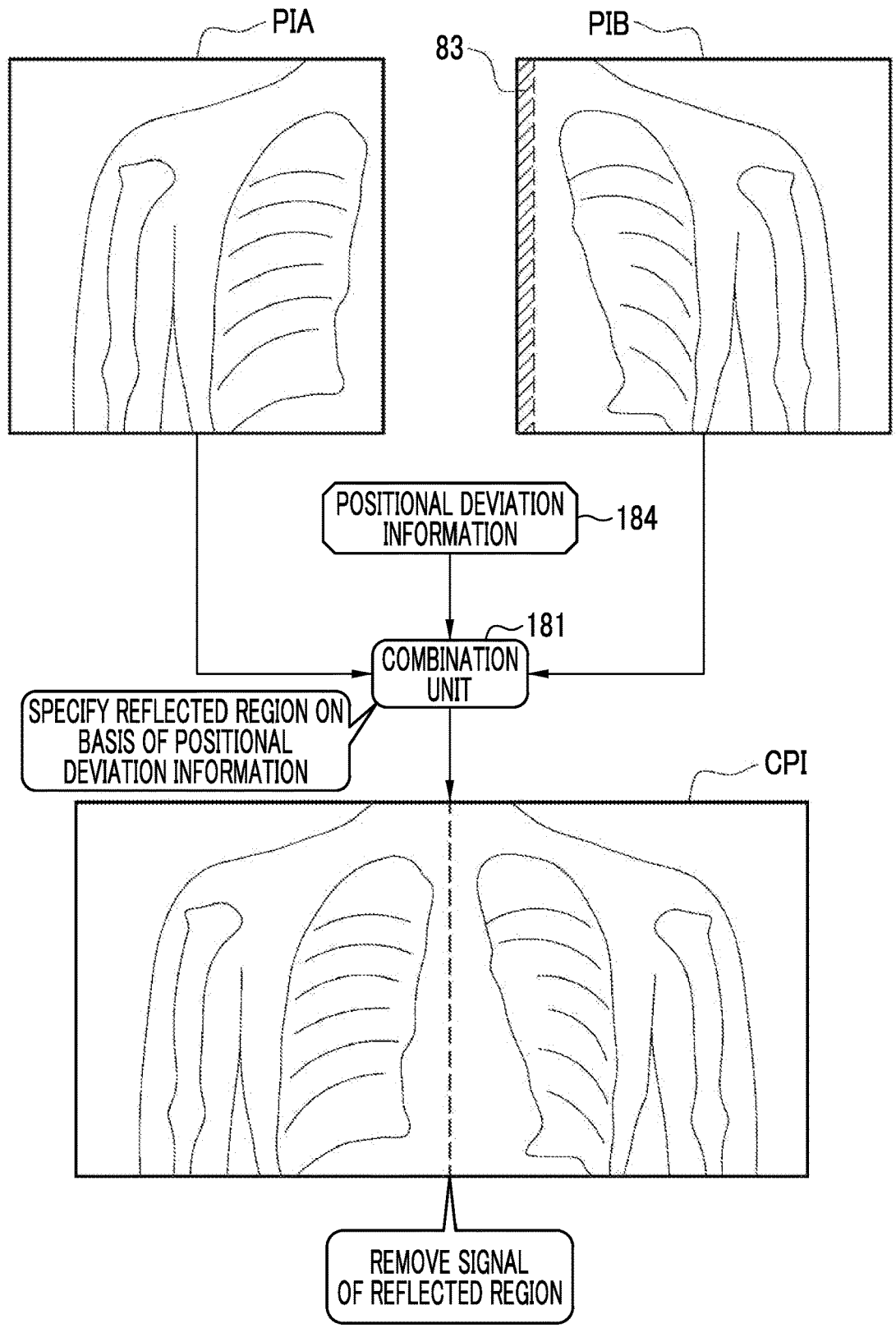
FIG. 22 is a diagram illustrating a process of a combination unit in a case in which a tomographic image is generated.
Figure 23:
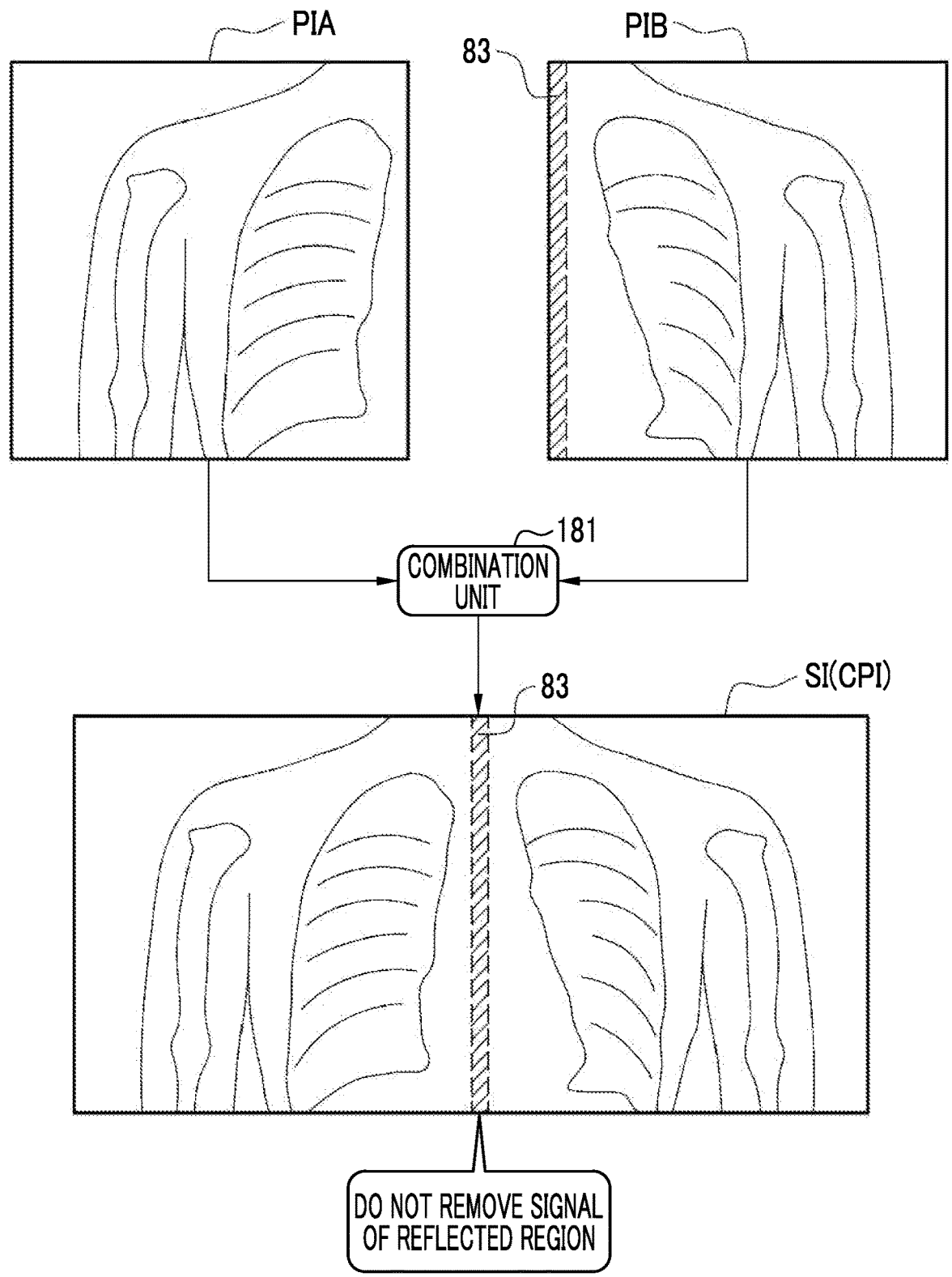
FIG. 23 is a diagram illustrating a process of the combination unit in a case in which a scout image is generated.

For example, as illustrated in FIG. 22, in a case in which the tomographic image TI is generated, the combination unit 181 specifies the reflected region 83 on the basis of the positional deviation information 184, removes a signal of the specified reflected region 83 from the projection image PIB, and combines the projection image PIB with the projection image PIA. A process of removing the signal of the reflected region 83 is an example of the "process related to image quality" according to the technology of the present disclosure. On the other hand, for example, as illustrated in FIG. 23, in a case in which the scout image SI is generated, the combination unit 181 combines the projection image PIB with the projection image PIA, without removing the signal of the reflected region 83 from the projection image PIB.

The above is summarized as illustrated in Table 195 of FIG. 24. That is, in a case in which the scout image SI is generated, none of the detection of the positional deviation of the sensor panels 42A and 42B by the positional deviation detection unit 180, the correction of the positional deviation by the combination unit 181, the specification of the reflected region 83 by the combination unit 181, and the removal of the signal of the reflected region 83 by the combination unit 181 are performed. On the other hand, in a case in which the tomographic image TI is generated, all of the detection of the positional deviation of the sensor panels 42A and 42B by the positional deviation detection unit 180, the correction of the positional deviation by the combination unit 181, the specification of the reflected region 83 by the combination unit 181, and the removal of the signal of the reflected region 83 by the combination unit 181 are performed.

Figure 25:
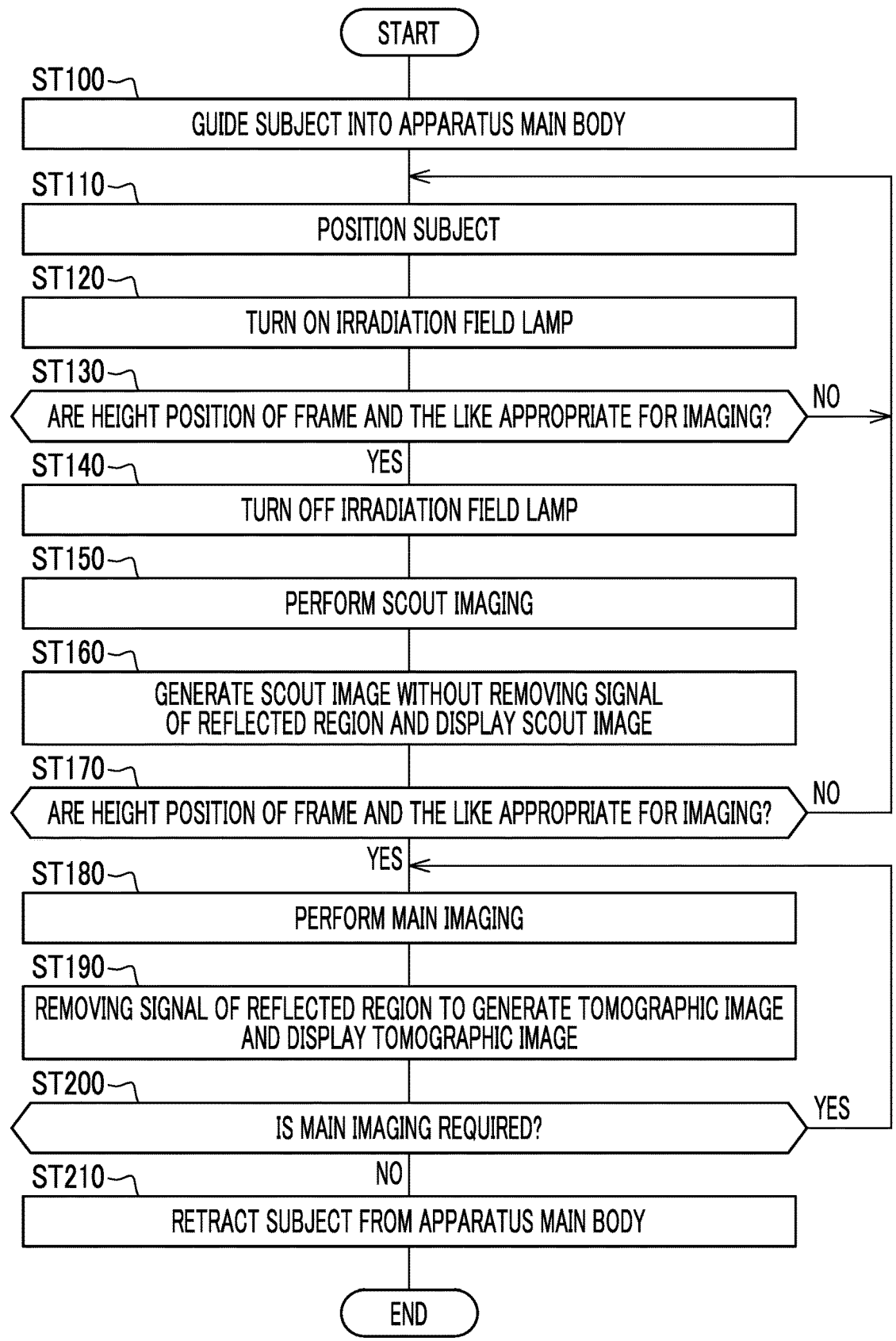
FIG. 25 is a flowchart illustrating a procedure of capturing the tomographic image by the CT apparatus.

Next, the operation of the above-mentioned configuration will be described with reference to a flowchart illustrated in FIG. 25. In a case in which the operation program 140 is started, the CPU 132 of the control device 12 functions as the receiving unit 145, the RW control unit 146, the imaging control unit 147, the image processing unit 148, and the display control unit 149 as illustrated in FIG. 14.

First, in a state in which the frame 18 is moved to the retracted height position and is rotated to the position of 60°, the operator guides the subject S into the apparatus main body 11 (Step ST100). Then, the operator positions the subject S (Step ST110).

After positioning the subject S, the operator inputs an instruction to turn on the irradiation field lamp 36 through the touch panel display 25. Then, the elevating mechanism 110 is operated to move the frame 18 to the height position registered in the irradiation condition table 141. Further, the rotation mechanism 120 is operated to rotate the frame 18 to the position of 0°. Further, after the irradiation field limiter 37 is driven and adjusted to the irradiation field corresponding to the irradiation conditions 156, the irradiation field lamp 36 is turned on, and the irradiation field is irradiated with visible light (Step ST120).

The operator determines whether or not the height position of the frame 18 and the positioning of the subject S are appropriate for imaging with reference to the visible light from the irradiation field lamp 36 (Step ST130). In a case in which the height position of the frame 18 and the positioning of the subject S are not appropriate for imaging (NO in Step ST130), the operator adjusts the height position of the frame 18 or repositions the subject S. In a case in which the height position of the frame 18 and the positioning of the subject S are appropriate for imaging (YES in Step ST130), the operator inputs an instruction to turn off the irradiation field lamp 36 through the touch panel display 25, and the irradiation field lamp 36 is turned off (Step ST140).

As illustrated in FIG. 16, after confirming the irradiation field of the radiation R, the operator inputs the scout imaging instruction 160 through the input device 134. The receiving unit 145 receives the scout imaging instruction 160. Then, the scout imaging command 161 is output from the imaging control unit 147 to, for example, the radiation source 20.

The rotation mechanism 120 is operated by the scout imaging command 161 to rotate the frame 18 to the rotation position registered in the irradiation condition table 141. Further, the radiation tube 35 irradiates the subject S with the radiation R for scout imaging, and the radiation detector 21 detects the radiation R transmitted through the subject S to obtain the projection image PI (Step ST150).

The image processing unit 148 performs various types of image processing on the projection image PI obtained by the radiation detector 21 to obtain the scout image SI. In this case, as illustrated in FIG. 23, the combination unit 181 of the image processing unit 148 combines the projection image PIA with the projection image PIB without removing the signal of the reflected region 83 from the projection image PIB. The scout image SI generated in this way is displayed on the touch panel display 25 and the display 133 under the control of the display control unit 149 (Step ST160).

The operator determines whether or not the height position of the frame 18 and the positioning of the subject S are appropriate for imaging again with reference to the scout image SI (Step ST170). In a case in which the height position of the frame 18 and the positioning of the subject S are not appropriate for imaging (NO in Step ST170), the operator adjusts the height position of the frame 18 or repositions the subject S.

In a case in which the height position of the frame 18 and the positioning of the subject S are appropriate for imaging (YES in Step ST170), the operator inputs the main imaging instruction 170 through the input device 134 as illustrated in FIG. 17. The receiving unit 145 receives the main imaging instruction 170. Then, the main imaging command 171 is output from the imaging control unit 147 to, for example, the radiation source 20.

The rotation mechanism 120 is operated in response to the main imaging command 171 to first rotate the frame 18 to the main imaging start position. Then, the frame 18 is rotated to the main imaging end position in the counterclockwise direction CCW. During that time, the radiation tube 35 irradiates the subject S with the radiation R for main imaging at a predetermined angle, and the radiation detector 21 detects the radiation R transmitted through the subject S whenever the subject S is irradiated to obtain a plurality of projection images PI (Step ST180).

The image processing unit 148 performs the reconstruction process on the plurality of projection images PI obtained by the radiation detector 21 to obtain the tomographic image TI. In this case, as illustrated in FIG. 22, the combination unit 181 of the image processing unit 148 removes the signal of the reflected region 83 from the projection image PIB and combines the projection image PIB with the projection image PIA. The tomographic image TI generated in this way is displayed on the touch panel display 25 and the display 133 under the control of the display control unit 149 (Step ST190).

The operator determines whether or not the tomographic image TI needs to be re-captured (Step ST200). In a case in which the operator determines that the tomographic image TI needs to be re-captured (YES in Step ST200), the operator inputs the main imaging instruction 170 through the input device 134, and the process returns to Step ST180.

In a case in which the operator determines that the tomographic image TI does not need to be re-captured (NO in Step ST200), the elevating mechanism 110 is operated in response to an instruction from the operator through the input device 134 to return the frame 18 to the retracted height position. Further, the rotation mechanism 120 is operated to return the frame 18 from the imaging end position to the position of 60° in the clockwise direction CW. After the frame 18 is returned to the retracted height position and the position of 60°, the operator retracts the subject S from the apparatus main body 11 (Step ST210). The series of Steps ST100 to ST210 is repeated in a case in which there is the next imaging order.

As described above, the radiation detector 21 of the CT apparatus 10 has the sensor panel unit 41 which includes the sensor panels 42A and 42B and in which the end portions 50A of the sensor panel 42A and the end portions 50B of the sensor panel 42B are arranged to overlap each other in the thickness direction. The image processing unit 148 of the CPU 132 of the control device 12 acquires the projection images PIA and PIB of the subject S from the sensor panels 42A and 42B. In a case in which the tomographic image TI which is a diagnosis image to be used for the doctor's diagnosis is generated, the combination unit 181 of the image processing unit 148 performs the process related to image quality on the projection image PI. In a case in which the scout image SI which is a confirmation image for confirming a reflected state of the subject is generated, the combination unit 181 does not perform the process related to image quality on the projection image PI. Since the process related to the image quality is not performed, the time required to generate the scout image SI is shortened. Therefore, it is possible to generate the scout image SI in a short time while ensuring the quality of the tomographic image TI.

In a case in which the scout image SI is generated, the positional deviation detection unit 180 does not operate, and the combination unit 181 does not specify the reflected region 83 on the basis of the positional deviation information 184. Further, in a case in which the scout image SI is generated, the signal of the reflected region 83 of the projection image PIB is not removed. Therefore, it is possible to further shorten the time required to generate the scout image SI.

The imaging region 61A of the sensor panel 42A and the imaging region 61B of the sensor panel 42B overlap each other in the overlap region 80 in a plan view of the sensor panel unit 41 in the thickness direction. Therefore, the marker 84 can be reflected in both the sensor panels 42A and 42B.

In the radiation detector 21, the marker 84 that is reflected in both the sensor panels 42A and 42B is attached at the preset position. The combination unit 181 detects the positional deviation of the sensor panels 42A and 42B on the basis of the set position and the reflected position where the marker 84 is actually reflected and specifies the reflected region 83 on the basis of the detected positional deviation. Therefore, it is possible to more accurately specify the reflected region 83 in consideration of the positional deviation of the sensor panels 42A and 42B from the set position. As a result, it is possible to suppress the deterioration of the quality of the tomographic image TI.

As illustrated in FIG. 10, the width W of the reflected region 83 is equal to or less than 10 mm. In a case in which the width W of the reflected region 83 is greater than 10 mm, there is a concern that a sense of incongruity caused by the removal of the signal of the reflected region 83 will occur in the tomographic image TI. However, it is possible to reduce the concern.

As illustrated in FIG. 8, the length LP of one side of the sensor panel 42 is equal to or greater than 300 mm. In a case in which the width W of the reflected region 83 is equal to or less than 10 mm and the length LP of one side of the sensor panel 42 is equal to or greater than 300 mm, the percentage of the reflected region 83 in the projection image PI is a relatively small value of about 3%. Therefore, it is possible to further reduce the concern that the sense of incongruity caused by the removal of the signal of the reflected region 83 will occur in the tomographic image TI.

The radiation detector 21 includes the support table 52 having the attachment surface 53 which has an arc surface shape toward the opposite side of the radiation source 20 and to which the sensor panel unit 41 is attached following the arc surface shape. For example, in a plan view of the sensor panel unit 41, as represented by a broken line in FIG. 26, the irradiation dose of the radiation R in an end portion is lower than that in a central portion of the sensor panel unit 41. As a result, a scan field of view (sFOV) 1, which is an imaging range that can be reconstructed as the tomographic image TI, is reduced. On the other hand, in a case in which the sensor panel unit 41 has an arc surface shape, the entire sensor panel unit 41 is irradiated with substantially the same amount of radiation R. Therefore, a scan field of view sFOV2 can be larger than the scan field of view sFOV1 (sFOV2>SFOV1). For example, while sFOV1 is 384 mm, sFOV2 is 406 mm. Therefore, the sensor panel unit 41 having an arc surface shape makes it possible to image a wider range of the subject S at once.

In addition, in some CT apparatuses according to the related art, a flat sensor panel unit 41 is moved in a plane direction to obtain sFOV1. However, this CT apparatus has disadvantages that a moving mechanism for moving the sensor panel unit 41 in the plane direction is required, which results in an increase in the size of the apparatus, and it takes a long time to perform imaging. In contrast, the CT apparatus 10 according to this example does not require the moving mechanism and does not take a long time for imaging.

As illustrated in FIG. 10, the tangent line TGA between the sensor panel 42A and the sensor panel 42B in the overlap region 80 is parallel to the tangent line TGB between the sensor panel 42B and the support table 52 in the overlap region 80. Therefore, the reflected region 83 can be more easily specified than that in a case in which the tangent lines TGA and TGB are not parallel to each other.

As illustrated in FIG. 11, the centers of curvature of the sensor panels 42A and 42B are located at the same position. Therefore, the reflected state of the subject S in the projection image PIA and the projection image PIB can be the same, and it is possible to reduce the sense of incongruity in the composite projection image CPI and thus the scout image SI and the tomographic image TI.

The sensor panel unit 41 includes two sensor panels 42A and 42B. Therefore, it is possible to provide the overlap region 80, which causes the deterioration of the quality of the tomographic image TI, at a minimum of one position, and thus to suppress the deterioration of the quality of the tomographic image TI. In addition, the reflected region 83 is specified at one position, and the combination is performed only once. Therefore, it is possible to shorten the time required to generate the tomographic image TI. In addition, the number of sensor panels 42 is not limited to two and may be three or more. In a case in which the number of sensor panels is increased, it is possible to image a wider range of the subject S at one time.

As illustrated in FIG. 9, in the sensor panel 42, the pixels 74 including TFTs are two-dimensionally arranged. The sensor panel 42 using the TFTs can have a larger area and a higher resolution than other imaging sensors such as complementary metal oxide semiconductor (CMOS) solid-state imaging elements. Therefore, it is possible to image a wider range of the subject S at one time and to obtain a high-quality tomographic image TI. In addition, the imaging sensor is not limited to the sensor panel 42 and may be a CMOS solid-state imaging element.

As illustrated in FIG. 9, the substrate 70 of the sensor panel 42 is made of a resin. Therefore, it is possible to increase the flexibility of the sensor panel 42, and the sensor panel 42 can be easily attached to the attachment surface 53 having an arc surface shape.

Figure 26:
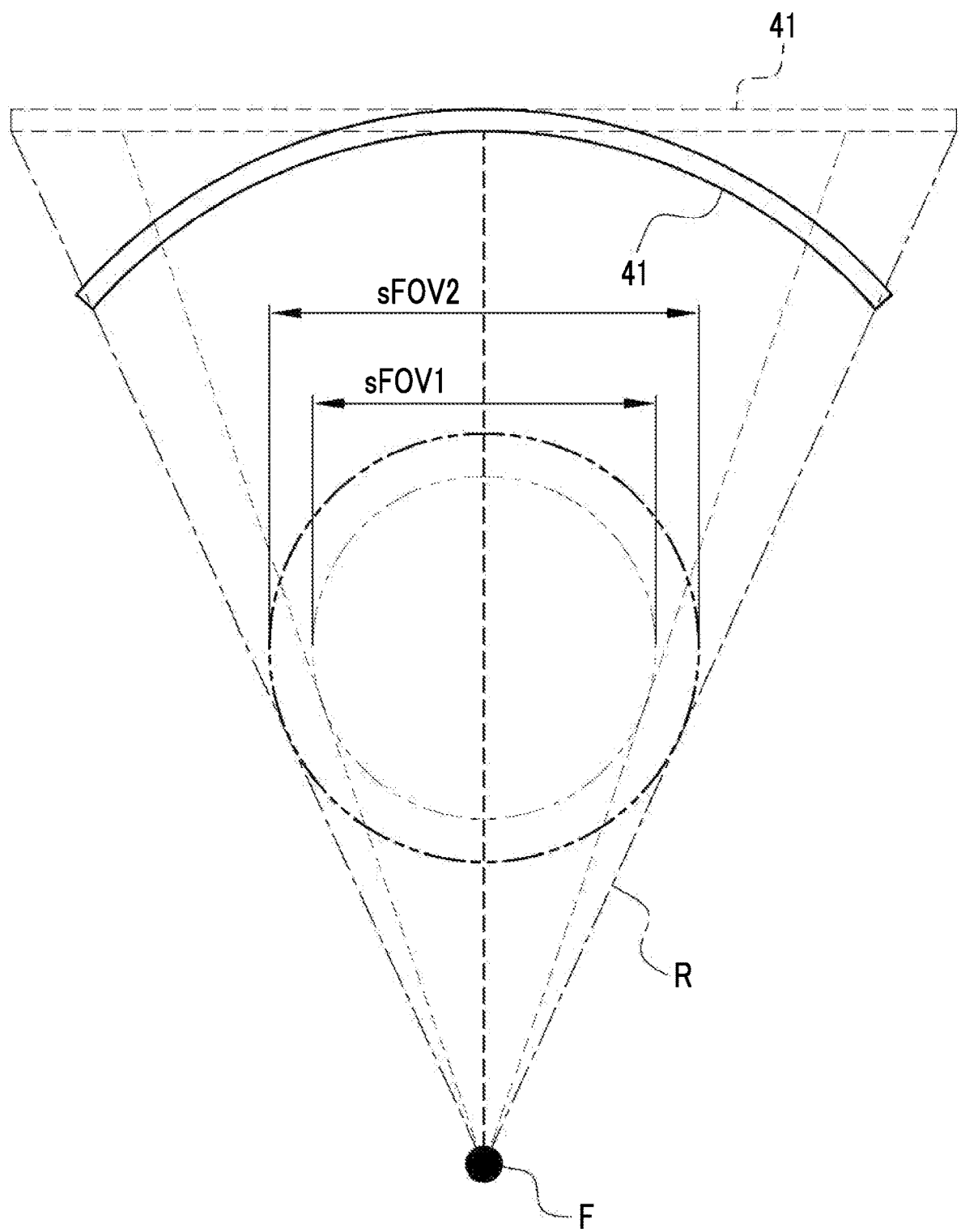
FIG. 26 is a diagram illustrating a scan field of view in a case in which the sensor panel has an arc surface shape and in a case in which the sensor panel has a planar shape.

The CT apparatus 10 comprises the annular frame 18 to which the radiation source 20 and the radiation detector 21 are attached and the rotation mechanism 120. The subject S is positioned in the cavity 19 of the frame 18. The rotation mechanism 120 rotates the frame 18 around the subject S in order to capture the projection images of the subject S at different angles. The radiation detector 21 includes the support table 52 having the attachment surface 53 which has an arc surface shape toward the opposite side of the radiation source 20 and to which the sensor panel unit 41 is attached following the arc surface shape. As illustrated in FIG. 26, the sensor panel unit 41 having an arc surface shape makes it possible to image a wider range of the subject S at one time.

In this example, the radiography apparatus is the CT apparatus 10 that generates the tomographic image TI as a diagnosis image on the basis of the projection images PI captured at different angles. In a case in which the tomographic image TI is generated, the CT apparatus 10 rotates the frame 18 and drives the radiation tube 35 at a predetermined angle to irradiate the subject S with the radiation R at a predetermined angle. Therefore, the imaging time is relatively long. Therefore, there is a demand for more quickly generating the scout image SI and quickly confirming the reflected state of the subject S with the scout image SI. Therefore, it is possible to further exert the effect of the technology of the present disclosure that can generate the scout image SI in a short time.

As illustrated in FIG. 6, the radiation source 20 emits the radiation R with a quadrangular pyramid shape. Therefore, it is possible to complete imaging in a short time as compared to a case in which the radiation source emits the radiation R with a fan shape to perform scanning in the height direction. In addition, the radiation R having a conical shape instead of the quadrangular pyramid shape may be emitted.

As illustrated in FIGS. 1 and 5, the subject S is positioned in the cavity 19 in either the standing posture or the sitting posture. Therefore, it is possible to meet the doctor's desire to observe soft tissues, such as the lungs, in a natural state in which gravity is applied or to observe joints, such as hip joints, in a state in which gravity is applied and a load is applied.

Figure 27:
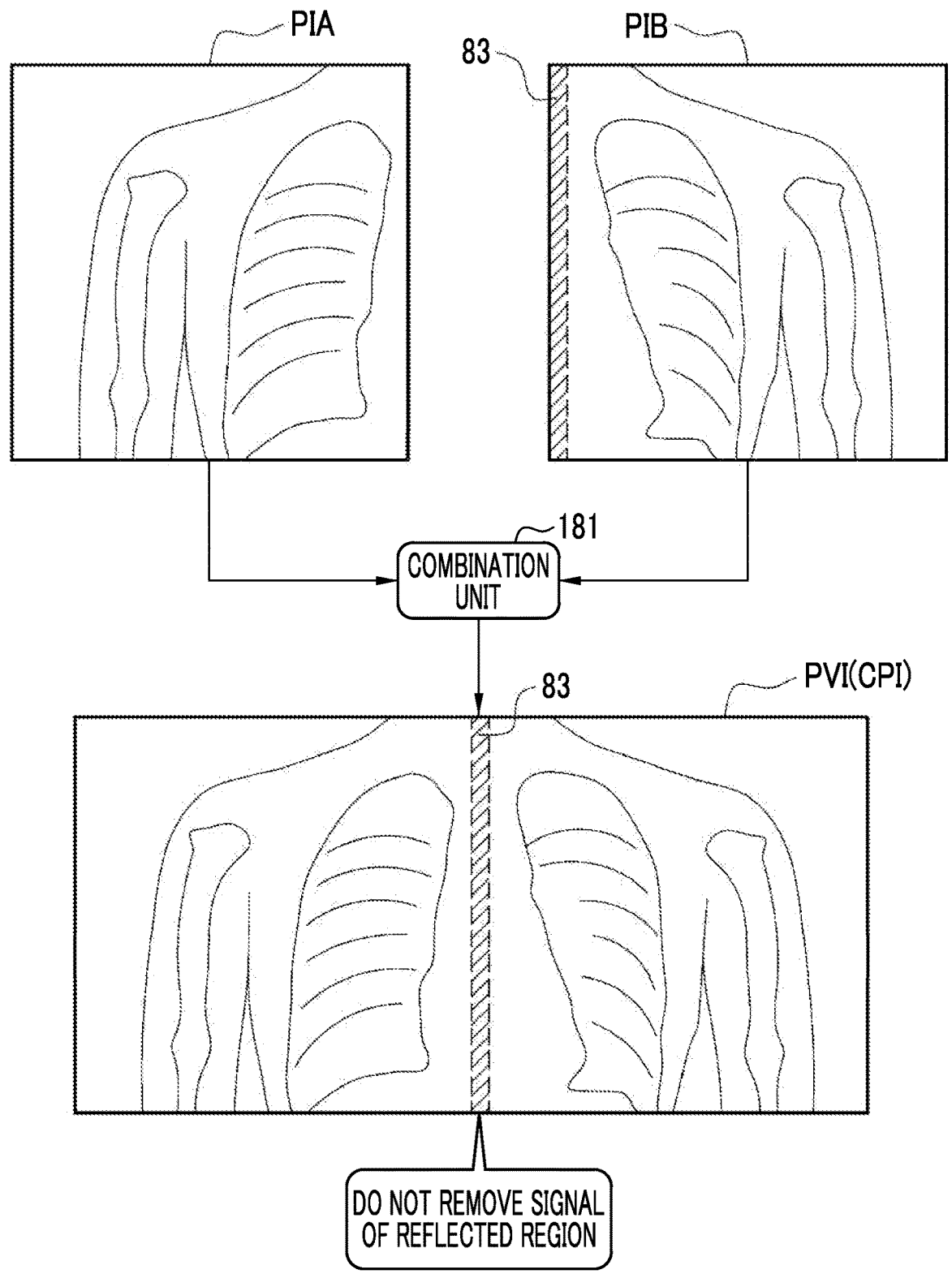
FIG. 27 is a diagram illustrating a process of the combination unit in a case in which a preview image is generated.

The scout image SI is given as an example of the confirmation image. However, the present disclosure is not limited thereto. For example, as illustrated in FIG. 27, in a case in which a preview image PVI is generated instead of or in addition to the scout image SI, the projection image PIB may be combined with the projection image PIA without removing the signal of the reflected region 83 of the projection image PIB. The preview image PVI is displayed on the touch panel display 25 and the display 133 under the control of the display control unit 149 before the tomographic image TI is displayed. The preview image PVI is generated on the basis of one of a plurality of projection images PI (strictly speaking, there are two projection images PIA and PIB, but the projection images PIA and PIB are collectively counted as one image) captured at different angles such as the projection images PIA and PIB obtained at the main imaging start position.

Figure 28:
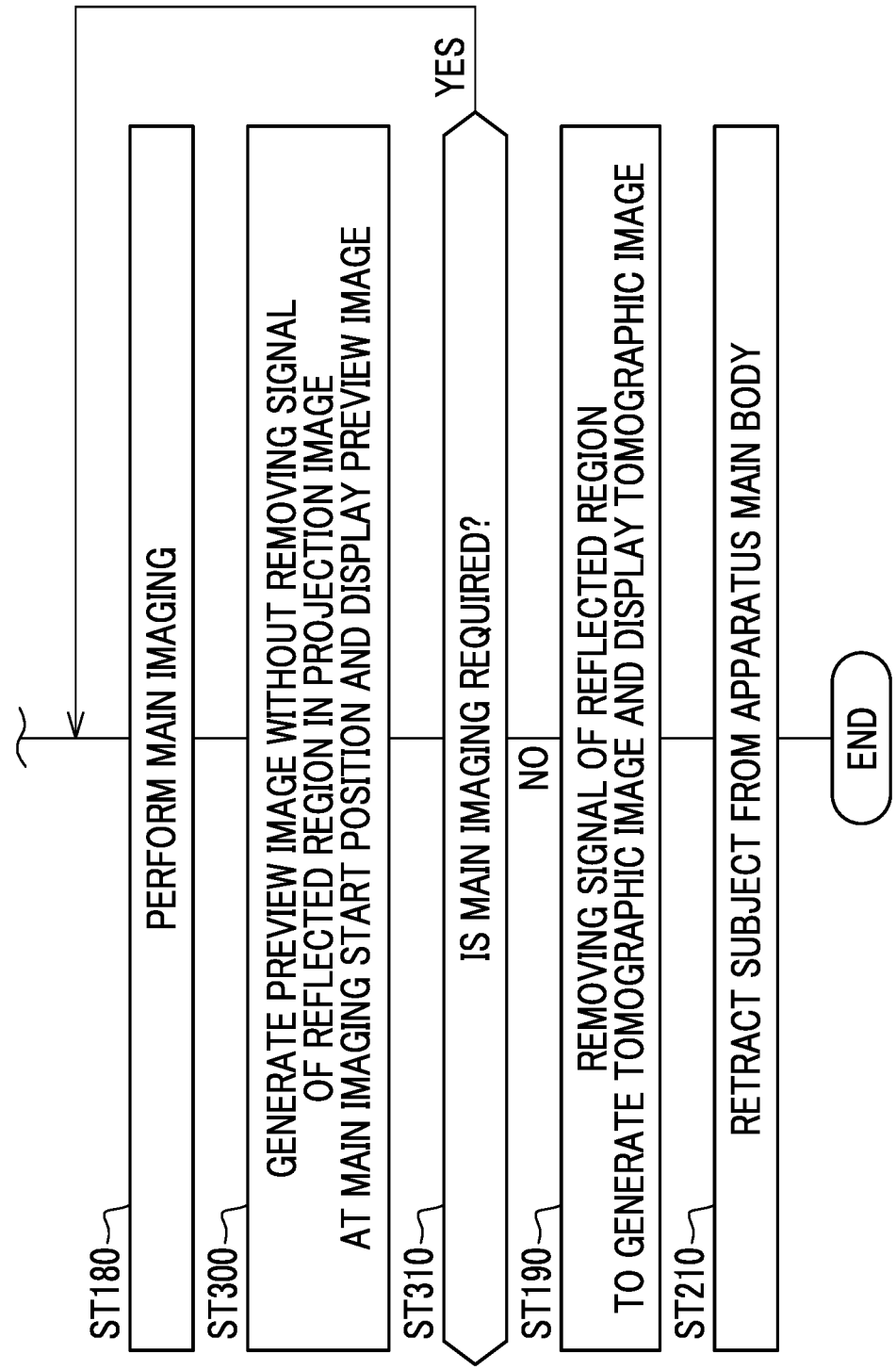
FIG. 28 is a flowchart illustrating a procedure of capturing a tomographic image by the CT apparatus in a case in which the preview image is generated.

In this case, for example, as illustrated in FIG. 28, after the main imaging in Step ST180 ends, first, the preview image PVI is generated on the basis of the projection images PIA and PIB obtained at the main imaging start position. In this case, as illustrated in FIG. 27, the combination unit 181 of the image processing unit 148 combines the projection image PIB with the projection image PIA, without removing the signal of the reflected region 83 from the projection image PIB. The preview image PVI generated in this way is displayed on the touch panel display 25 and the display 133 under the control of the display control unit 149 (Step ST300).

The operator determines whether or not the tomographic image TI needs to be re-captured with reference to the preview image PVI (Step ST310). In a case in which the operator determines that the tomographic image TI needs to be re-captured (YES in Step ST310), the operator inputs the main imaging instruction 170 through the input device 134 again, and the process returns to Step ST180.

In a case in which the operator determines that the tomographic image TI does not need to be re-captured (NO in Step ST310), the image processing unit 148 performs the reconstruction process on the plurality of projection images PI obtained by the radiation detector 21 to obtain the tomographic image TI. In this case, as illustrated in FIG. 22, the combination unit 181 of the image processing unit 148 removes the signal of the reflected region 83 from the projection image PIB and combines the projection image PIB with the projection image PIA. The tomographic image TI generated in this way is displayed on the touch panel display 25 and the display 133 under the control of the display control unit 149 (Step ST190).

Similarly to the scout image SI, the preview image PVI may be used to confirm the reflected state of the subject S. Therefore, even in a case in which the preview image PVI is generated, it is preferable to shorten the time required for generation without performing the process related to image quality.

Second Embodiment

Figure 29:
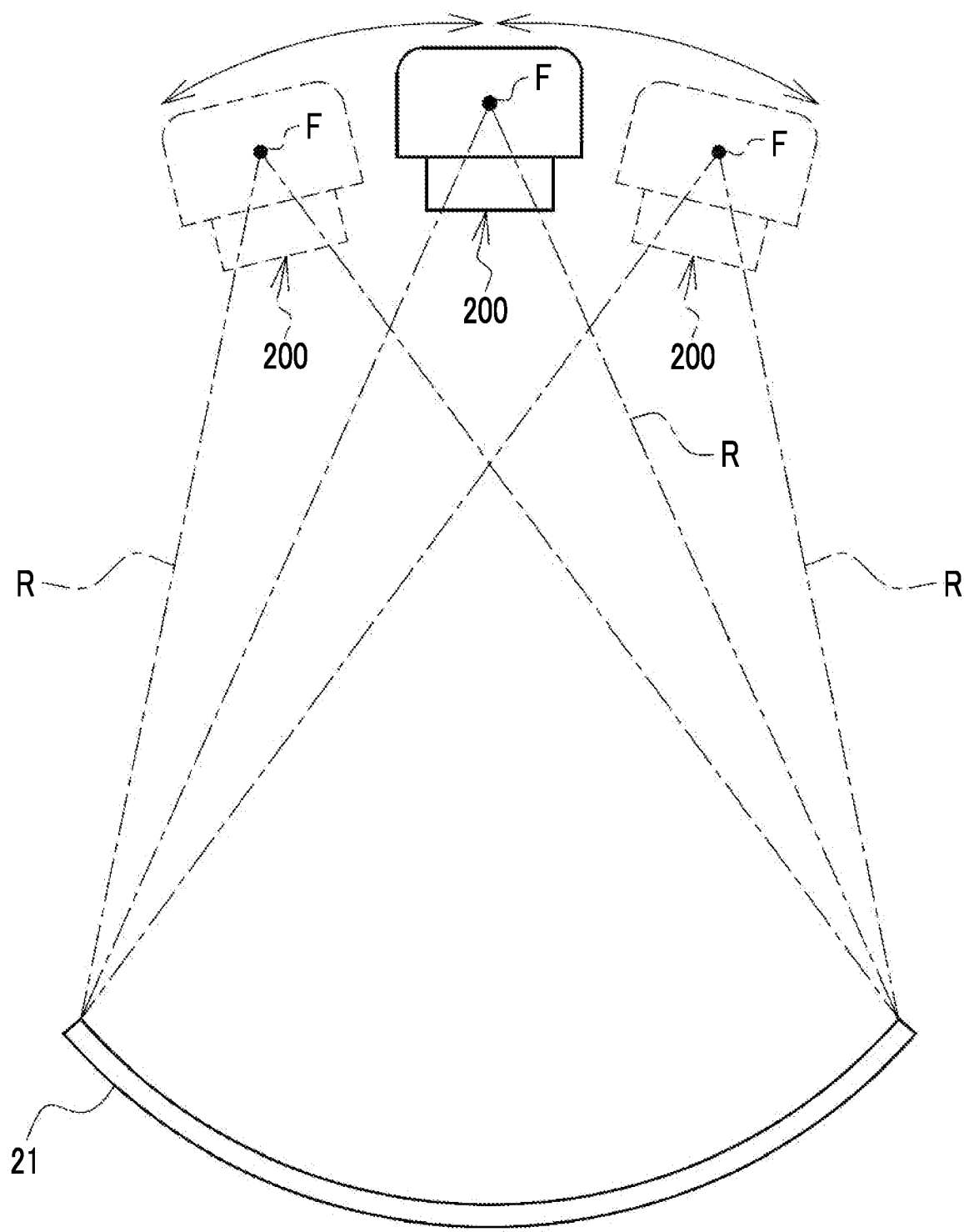
FIG. 29 is a diagram illustrating an example of a configuration in which an irradiation angle of radiation with respect to the radiation detector can be changed.
Figure 30:
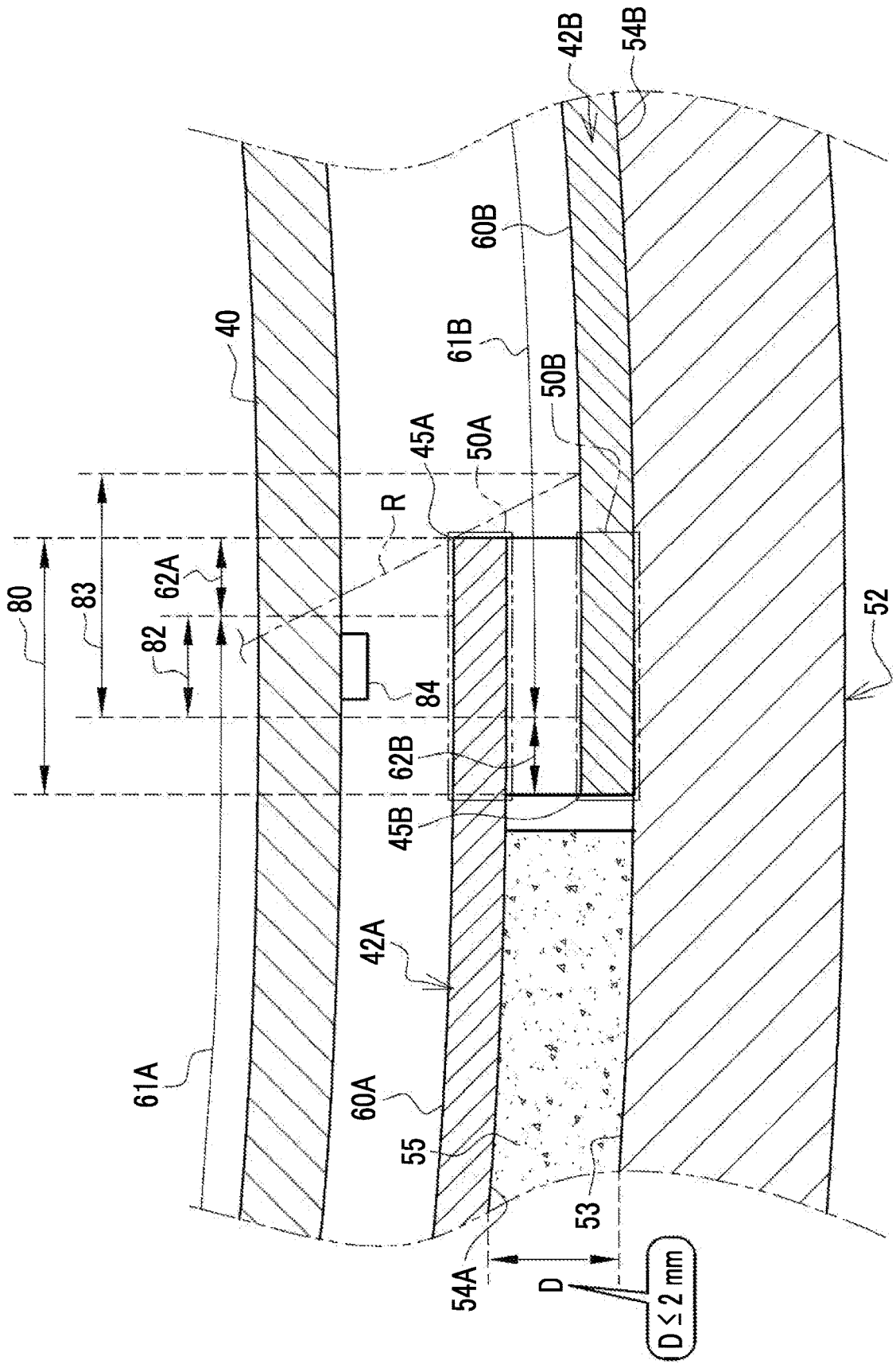
FIG. 30 is a diagram illustrating a reflected region in a case in which the radiation is obliquely incident on the overlap region.

For example, as illustrated in FIG. 29, a radiation source 200 according to a second embodiment has a configuration in which the irradiation angle of the radiation R with respect to the radiation detector 21 can be changed. For example, the radiation source 200 is rotated from a position facing the radiation detector 21 by a predetermined angle along the annular frame 18. In a case in which the radiation source 200 is moved to a position that is rotated from the position facing the radiation detector 21 by a predetermined angle, the radiation R is obliquely incident on the overlap region 80 as illustrated in FIG. 30 as an example. In this case, the width W of the reflected region 83 is larger than that of the reflected region 83 in a case in which the radiation R is incident at an irradiation angle of 90° as in the first embodiment by a value corresponding to the extension of the image of the end portion 50A reflected in the imaging region 61B.

That is, the reflected region 83 changes depending on the irradiation angle of the radiation R.

Figure 31:
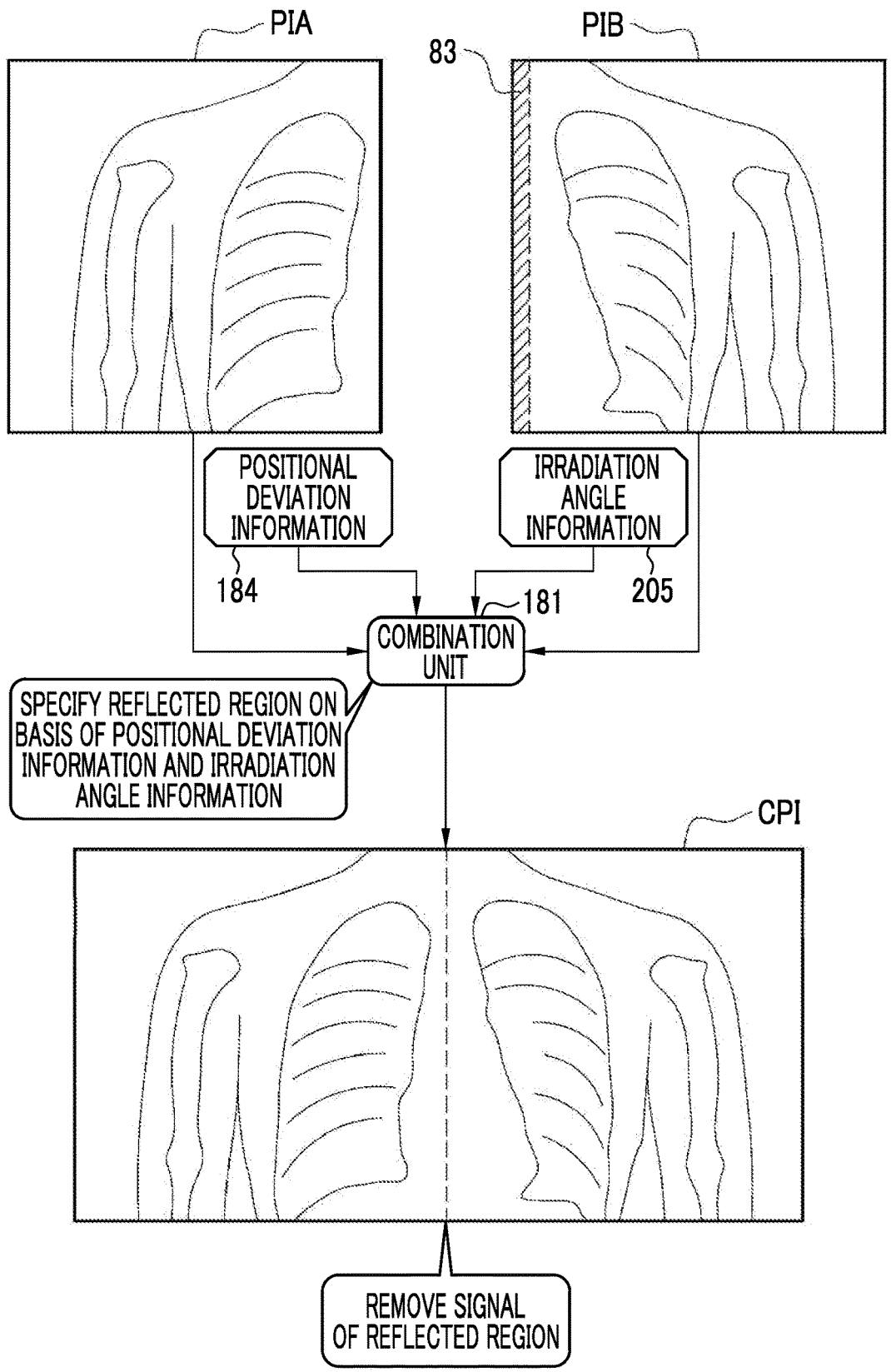
FIG. 31 is a diagram illustrating a process of a combination unit in a case in which a tomographic image is generated in a second embodiment.

For example, as illustrated in FIG. 31, in the second embodiment, in a case in which the tomographic image TI is generated, in addition to the positional deviation information 184, irradiation angle information 205 indicating the irradiation angle of the radiation R is input to the combination unit 181. The combination unit 181 specifies the reflected region 83 on the basis of the positional deviation information 184 and the irradiation angle information 205. Then, after the signal of the specified reflected region 83 is removed from the projection image PIB, the projection image PIB is combined with the projection image PIA.

As described above, in the second embodiment, the irradiation angle of the radiation R with respect to the radiation detector 21 can be changed. The combination unit 181 specifies the reflected region 83 that changes depending on the irradiation angle. Therefore, it is possible to more accurately specify the reflected region 83 in consideration of the irradiation angle of the radiation R. As a result, it is possible to suppress the deterioration of the quality of the tomographic image TI.

In addition, the radiation source 20 may be translated in the left-right direction. Further, the radiation detector 21 may be moved in addition to or instead of the radiation source 20.

Third Embodiment

Figure 32:
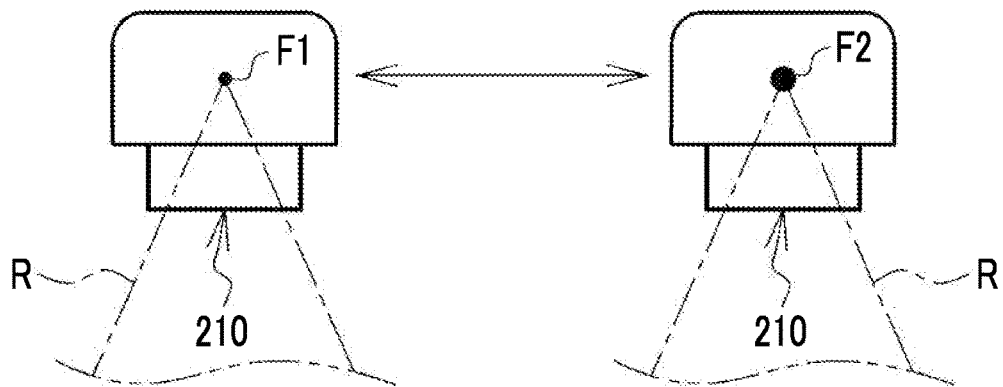
FIG. 32 is a diagram illustrating an example of a configuration in which a size of a focus of the radiation can be changed.

For example, as illustrated in FIG. 32, a radiation source 210 according to the third embodiment has a configuration in which the irradiation angle of the radiation R with respect to the radiation detector 21 can be changed, similarly to the radiation source 200 according to the second embodiment, and the focus F of the radiation R can be changed to a relatively small focus F1 and a relatively large focus F2. As a method for changing the size of the focus F, for example, a method can be adopted in which radiation tubes 35 having different sizes of the focus F and the diameter of an electron beam given from a cathode to an anode of the radiation tube 35 is changed.

Figure 33:
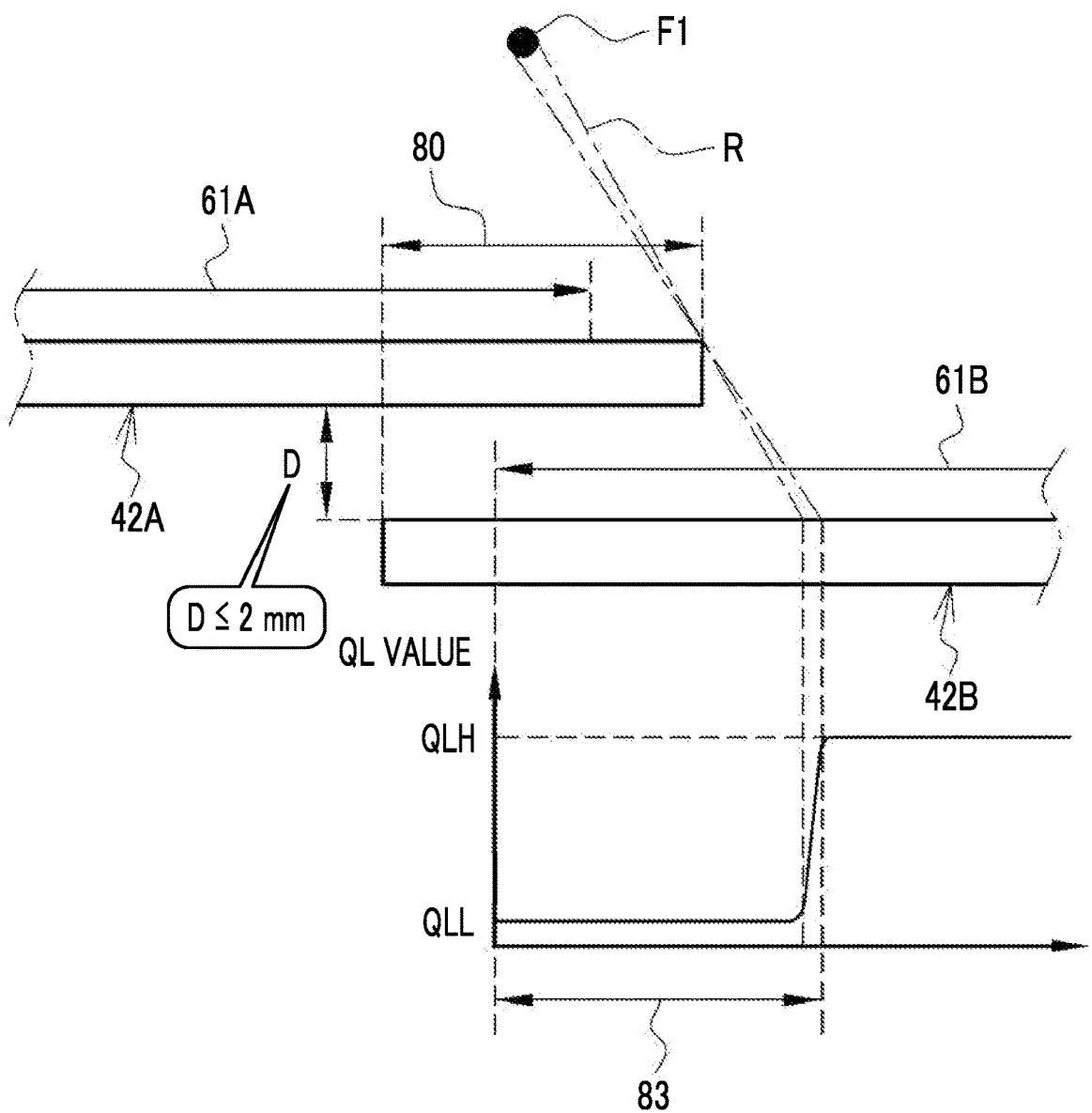
FIG. 33 is a diagram illustrating a reflected region in a case in which the focus is relatively small.
Figure 34:
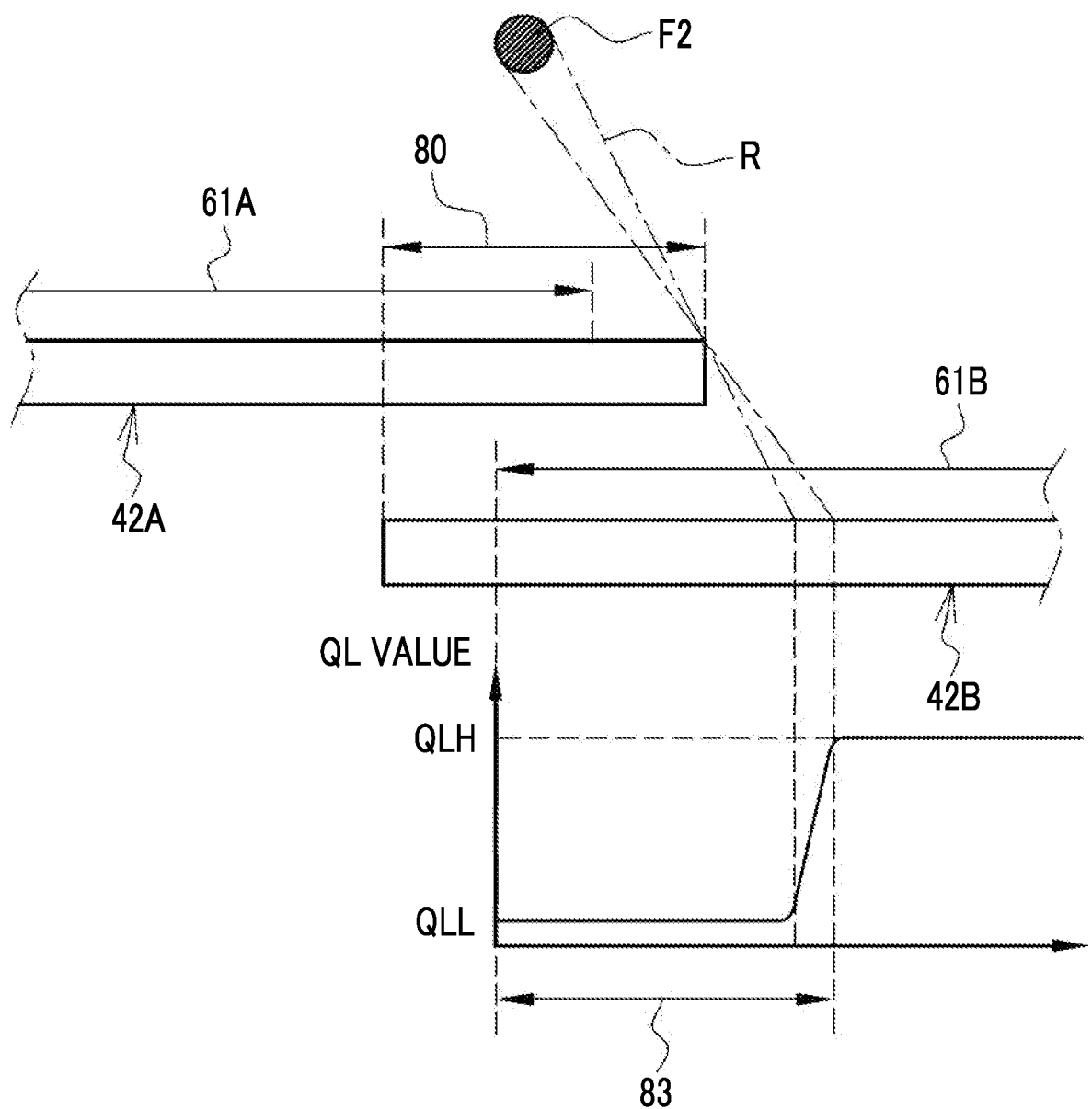
FIG. 34 is a diagram illustrating a reflected region in a case in which the focus is relatively large.

In this case, for example, as illustrated in FIGS. 33 and 34, the radiation R is obliquely incident on the overlap region 80. The irradiation angle of the radiation R emitted from one end of the focus F is slightly different from the irradiation angle of the radiation R emitted from the other end of the focus F. A quantum level (QL) value of the projection image PIB does not decrease all at once from QLH to QLL in the vicinity of the end portion 50B, but gradually decreases due to the slight difference between the irradiation angles of the radiation R. In the third embodiment, the position where the QL value starts to decrease from QLH to QLL is specified as one end of the reflected region 83.

FIG. 33 illustrates the case of the relatively small focus F1, and FIG. 34 illustrates the case of the relatively large focus F2. In the case of the focus F2, the width W of the reflected region 83 is larger than that of the reflected region 83 in the case of the focus F1. That is, the reflected region 83 changes depending on the size of the focus F of the radiation R.

Figure 35:
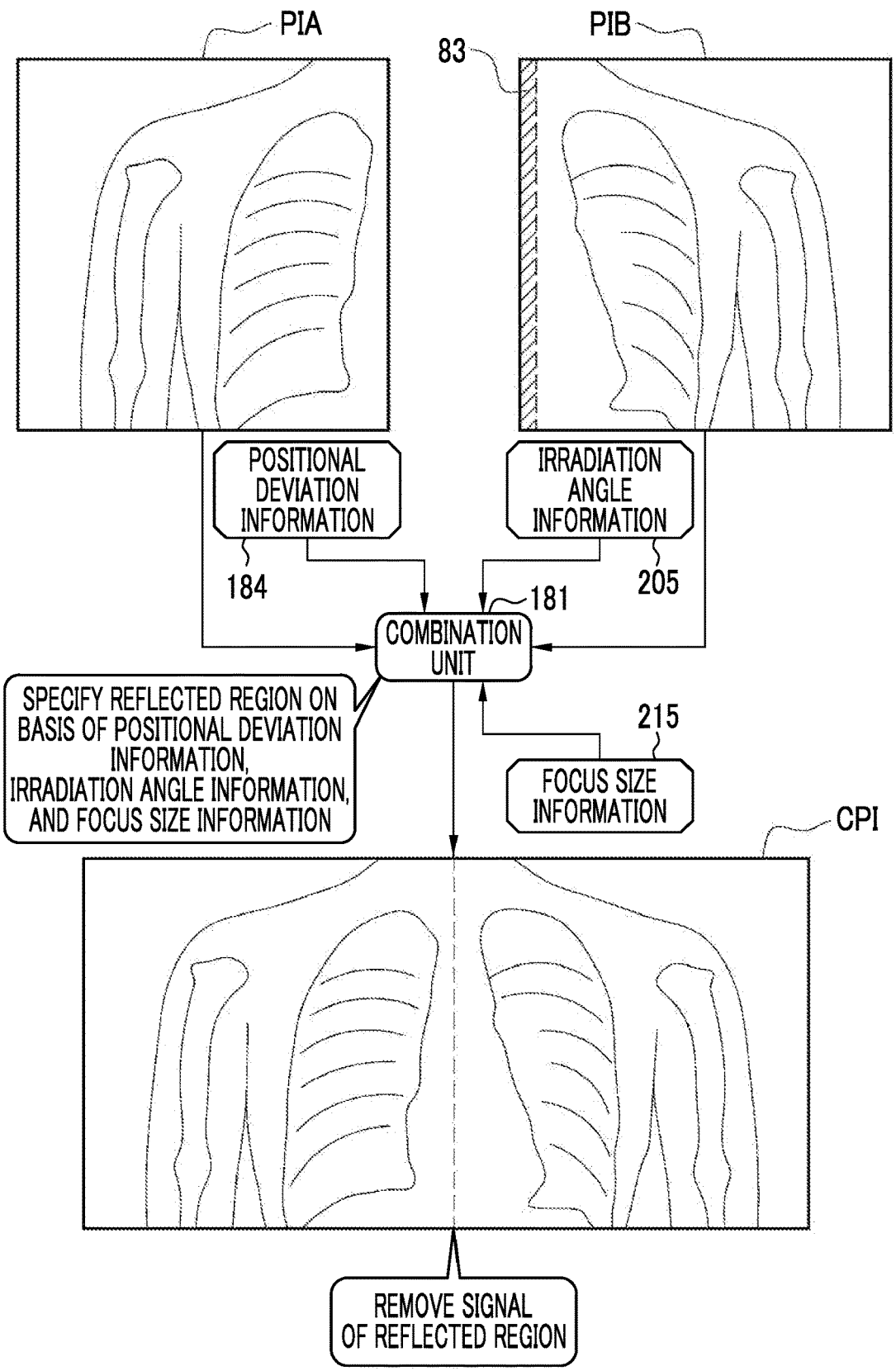
FIG. 35 is a diagram illustrating a process of a combination unit in a case in which a tomographic image is generated in a third embodiment.

For example, as illustrated in FIG. 35, in the third embodiment, in a case in which the tomographic image TI is generated, in addition to the positional deviation information 184 and the irradiation angle information 205, focus size Information 215 indicating the size of the focus F of the radiation R is input to the combination unit 181. The combination unit 181 specifies the reflected region 83 on the basis of the positional deviation information 184, the irradiation angle information 205, and the focus size information 215. Then, after the signal of the reflected region 83 is removed from the projection image PIB, the projection image PIB is combined with the projection image PIA.

As described above, the third embodiment has the configuration in which the radiation R can be obliquely incident on the overlap region 80, and the size of the focus F of the radiation R can be changed. The combination unit 181 specifies the reflected region 83 that changes depending on the size of the focus F. Therefore, it is possible to more accurately specify the reflected region 83 in consideration of the size of the focus F of the radiation R. As a result, it is possible to suppress the deterioration of the quality of the tomographic image TI. In addition, the focus F to be changed is not limited to two focuses F1 and F2, and three or more focuses may be provided.

In the second embodiment and the third embodiment, as illustrated in FIGS. 30 and 33, it is preferable that the distance D between the sensor panel 42A and the sensor panel 42B in the thickness direction is equal to or less than 2 mm. In a case in which the distance D is greater than 2 mm, the image of the end portion 50A reflected in the imaging region 61B is extended, and the width W of the reflected region 83 is increased. As a result, there is a concern that the sense of incongruity caused by removing the signal of the reflected region 83 will occur in the tomographic image TI.

Fourth Embodiment

In the first embodiment and the like, the support table 52 having the attachment surface 53 with an arc surface shape (U-shape) is given as an example. However, the present disclosure is not limited thereto.

Figure 36:
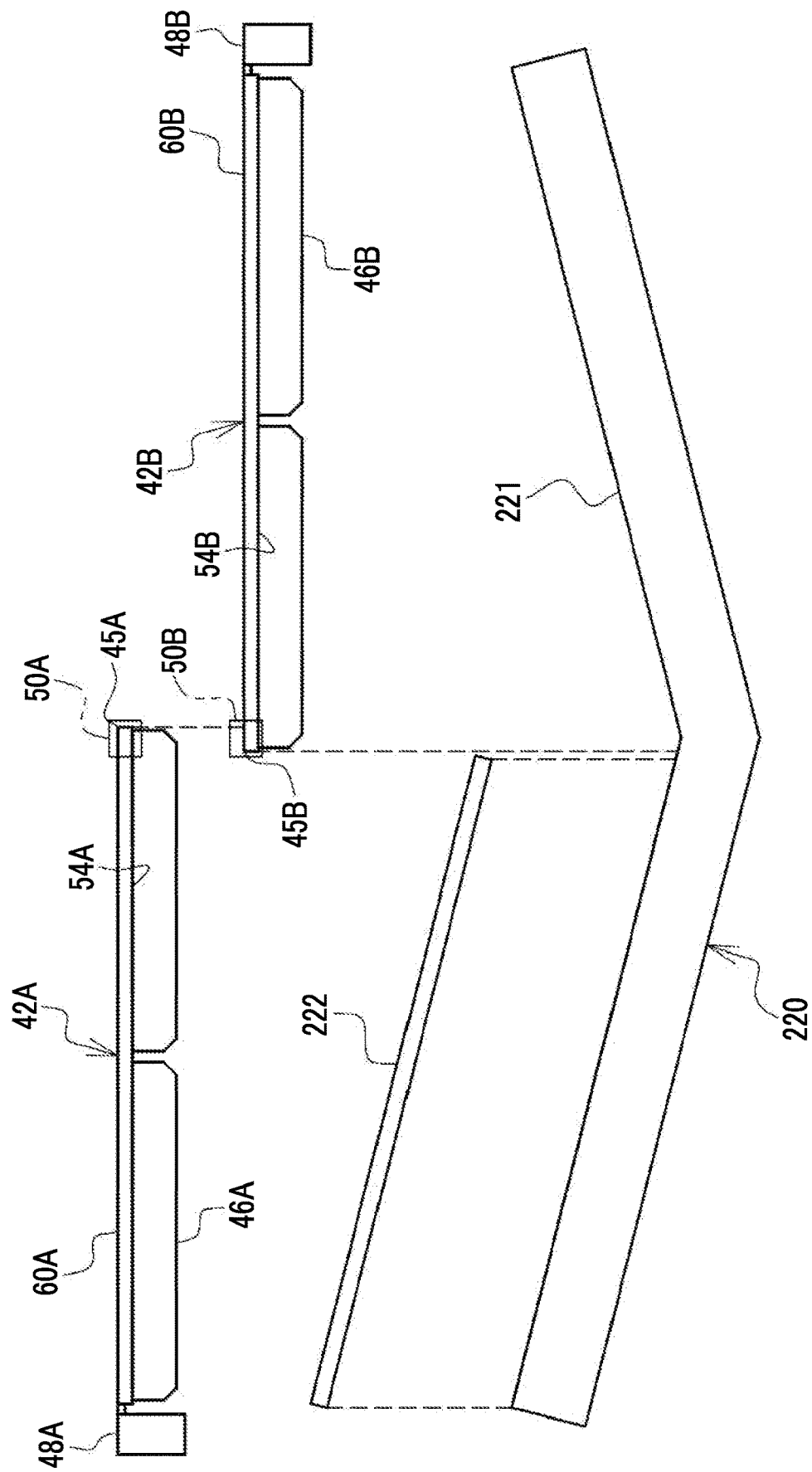
FIG. 36 is an exploded plan view illustrating two sensor panels, a spacer, and a support table in a fourth embodiment.

For example, as illustrated in FIG. 36, a support table 220 according to a fourth embodiment has an attachment surface 221 with a V-shape. Here, the "V-shape" is a shape in which most parts including the imaging regions 61A and 61B of the sensor panels 42A and 42B are planar and the end portions 50A and 50B overlapping each other intersect at an angle of less than 180°. Specifically, the "V-shape" means a shape in which both end portions protrude toward one side and both end portions and a central portion are connected by a plane. A spacer 222 is attached to an attachment surface 221. The spacer 222 is a thin plate that has substantially the same size as the sensor panel 42A and has a straight shape following the shape of the attachment surface 221. The spacer 222 has a thickness corresponding to the distance between the sensor panel 42A and the support table 220.

The sensor panels 42A and 42B are fixed in the end portions 50A and 50B. Further, the first surface 54B of the sensor panel 42B is fixed to the attachment surface 221 in the end portion 50B. Therefore, the sensor panel unit 41 has a V-shape following the shape of the attachment surface 221.

Figure 37:
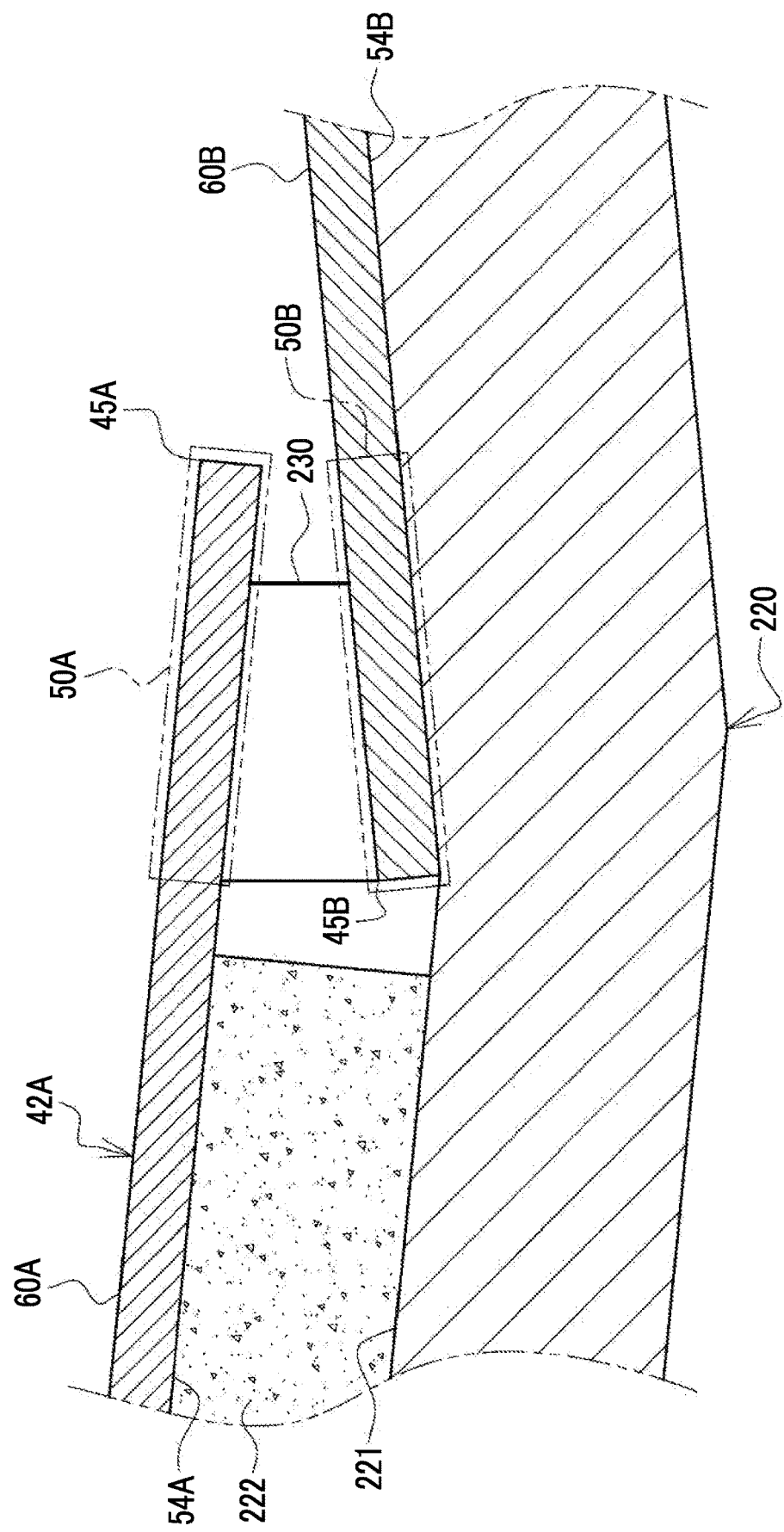
FIG. 37 is a cross-sectional view illustrating the vicinity of an overlap region of end portions of the two sensor panels in the fourth embodiment.

For example, as illustrated in FIG. 37, a fixing member 230 for fixing the end portion 50A of the sensor panel 42A and the end portion 50B of the sensor panel 42B has a distorted shape as compared to the simple shape of the fixing member 81 according to the first embodiment since the end portions 50A and the end portions 50B intersect in the V-shape. Therefore, the fixing member 230 is made of a material having a higher flexibility in shape than the fixing member 81.

Figure 38:
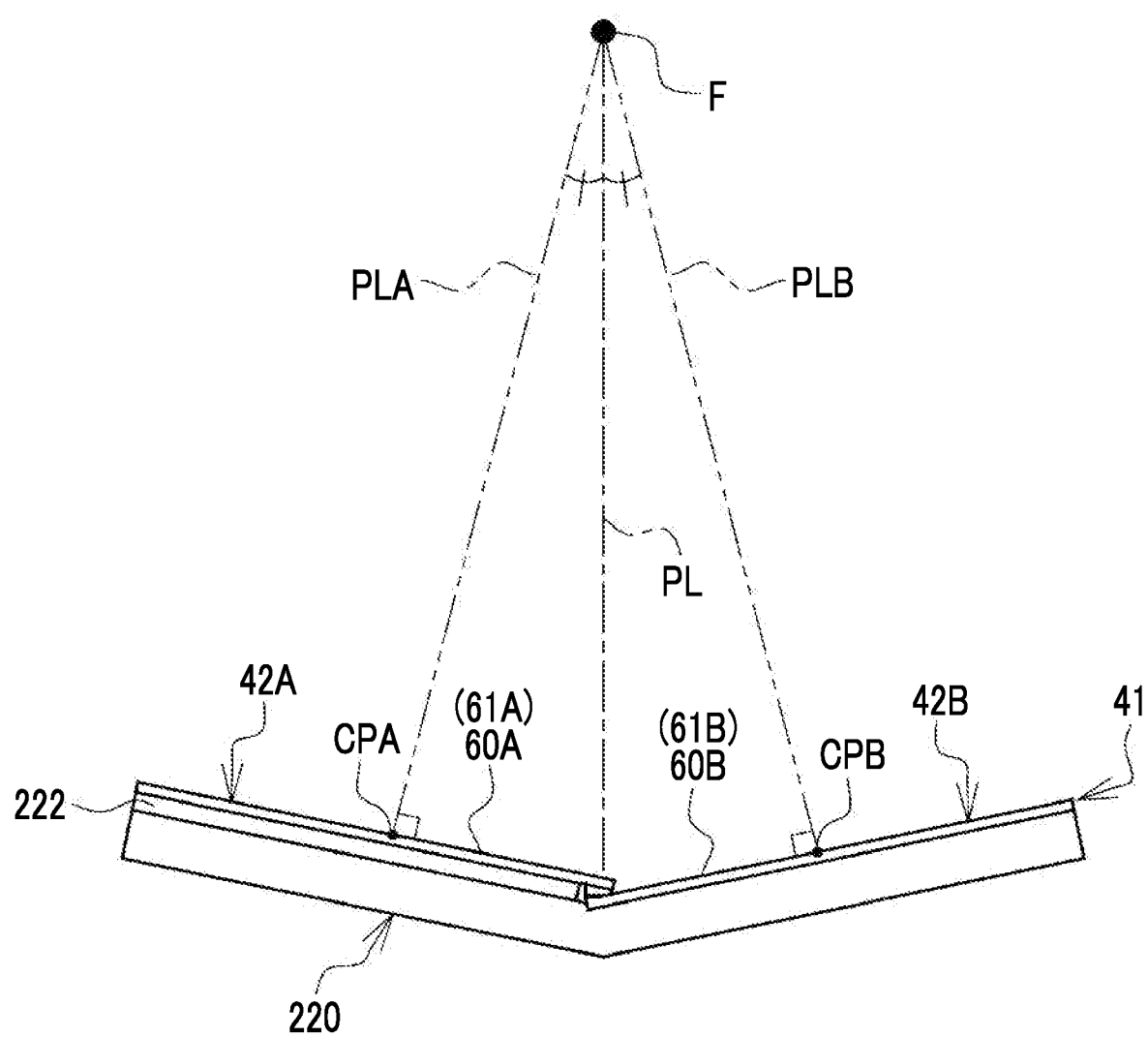
FIG. 38 is a diagram illustrating a positional relationship between a focus of radiation and the sensor panels in the fourth embodiment.

For example, as illustrated in FIG. 38, in the fourth embodiment, the perpendicular line PLA drawn from the focus F of the radiation R to the second surface 60A of the sensor panel 42A intersects the center point CPA of the imaging region 61A. Similarly, a perpendicular line PLB drawn from the focus F to the second surface 60B of the sensor panel 42B intersects a center point CPB of the imaging region 61B. The perpendicular lines PLA and PLB have the same length and have the same angle with respect to a perpendicular line PL drawn from the focus F to a center point of the sensor panel unit 41. Therefore, the sensor panels 42A and 42B are substantially mirror-symmetric with respect to the perpendicular line PL.

Even in a case in which the attachment surface 221 has a V-shape and the sensor panel unit 41 has a shape following the shape, the scan field of view sFOV2 can be larger than the scan field of view sFOV1 in a case in which the sensor panel unit 41 is planar. In this case, the substrate 70 of the sensor panel 42 may be made of glass instead of the resin as in the above-mentioned example.

The U-shape is not limited to the exemplified arc surface shape. The shape may be an elliptical arc surface shape or a bowl shape such as a parabolic antenna shape. Further, the frame 18 is not limited to the circular ring and may be a polygonal ring.

The example in which the rear surface of the substrate 70 is the first surface 54 has been described. However, conversely, the sensor panel 42 may be attached to the support table 52 such that the rear surface of the substrate 70 is the second surface 60.

The "process related to image quality" is not limited to the above-mentioned process of removing the signal of the reflected region 83. For example, the process may be a process in Table 235 illustrated in FIG. 39.

In the example illustrated in FIG. 39, offset correction, defective pixel correction, shading correction, residual image correction, scattered ray correction, and reference correction are given as an example of the process in a case in which the scout image SI and the tomographic image TI are generated. The offset correction is a process that subtracts an offset correction image detected in a state in which the radiation R is not emitted from the projection image PI in units of the pixels 74. The defective pixel correction is a process that linearly interpolates the pixel value of a pixel 74 having an abnormal pixel value in the projection image PI with the pixel values of the surrounding normal pixels 74 on the basis of information of the pixel (defective pixel) 74 having the abnormal pixel value generated at the time of shipment or periodic inspection. The shading correction is a process that corrects, for example, a variation in the sensitivity of the light receiving unit of each pixel 74 and a variation in the output characteristics of a reading circuit on the basis of shading correction data. The residual image correction is a process that removes a residual image caused by the previous imaging from the projection image PI.

The scattered ray correction is a process that removing scattered ray components from the projection image PI using scattered ray correction data prepared in advance according to various body types of the subject S such as thin, normal, and thick body types. The reference correction is a process that uses, as a reference, the pixel value of a blank region in which the subject S is not reflected in the projection image PI. A fluctuation of the output of the radiation source 20 over time can be seen from the pixel value of the blank region. For example, in a case in which the tube current applied to the radiation source 20 is greater than the set value due to a fluctuation over time, the pixel value of the blank region is greater than the assumed value. The reference correction is a process that multiplies the projection image PI by a correction coefficient corresponding to the difference between the actual pixel value of the blank region and the assumed value. For example, in a case in which the pixel value of the blank region is greater than the assumed value, the projection image PI is multiplied by a correction coefficient smaller than 1.

In the example illustrated in FIG. 39, the offset correction and the defective pixel correction are performed in both a case in which the scout image SI is generated and a case in which the tomographic image TI is generated. On the other hand, the shading correction, the residual image correction, the scattered ray correction, and the reference correction are not performed in a case in which the scout image SI is generated and are performed in a case in which the tomographic image TI is generated. In this case, the shading correction, the residual image correction, the scattered ray correction, and the reference correction are examples of the "process related to image quality" according to the technology of the present disclosure. Further, in a case in which the scout image SI is generated, not only the shading correction, the residual image correction, the scattered ray correction, and the reference correction but also the offset correction and the defective pixel correction may not be performed.

4×4 or 3×3 binning may be performed on the projection image PI in a case in which the scout image SI is generated, and 2×2 binning may be performed on the projection image PI or the binning may not be performed thereon in a case in which the tomographic image TI is generated such that the number of pixels handled in a case in which the scout image SI is generated smaller than the number of pixels handled in a case in which the tomographic image TI is generated. This makes it possible to shorten the time required to generate the scout image SI.

In addition, the imaging region 61A of the sensor panel 42A and the imaging region 61B of the sensor panel 42B may not overlap each other in the overlap region 80 in a plan view of the sensor panel unit 41 in the thickness direction. In short, it is sufficient that the reflected region 83 in which the end portion 50A is reflected is present in the imaging region 61B.

The CT apparatus 10 is given as an example of the radiography apparatus. However, the present disclosure is not limited thereto. The radiography apparatus may be a simple radiography apparatus that captures the projection images one by one while changing the angle. Further, a radiography apparatus may be used which includes a frame to which two sets of the radiation source 20 and the radiation detector 21 are attached, simultaneously irradiates the front surface and the side surface of the subject S with the radiation R to obtain two projection images, and investigates the anatomical shape of the hip joint and spine of subject S and the connection between the spine and the lower limbs.

The hardware configuration of the computer constituting the control device 12 can be modified in various ways. For example, the control device 12 may be configured by a plurality of computers separated as hardware in order to improve processing capacity and reliability. For example, the functions of the receiving unit 145 and the RW control unit 146 and the functions of the imaging control unit 147, the image processing unit 148, and the display control unit 149 are distributed to two computers. In this case, the two computers constitute the control device 12.

As described above, the hardware configuration of the computer of the control device 12 can be appropriately changed according to required performances, such as processing capacity, safety, and reliability. Further, not only the hardware but also an application program, such as the operation program 140, may be duplicated or may be dispersively stored in a plurality of storages in order to ensure safety and reliability.

In each of the above-described embodiments, for example, the following various processors can be used as the hardware structure of processing units performing various processes, such as the receiving unit 145, the RW control unit 146, the imaging control unit 147, the image processing unit 148 (the positional deviation detection unit 180, the combination unit 181, and the reconstruction unit 182), and the display control unit 149. The various processors include, for example, the CPU 132 which is a general-purpose processor executing software (operation program 140) to function as various processing units, a programmable logic device (PLD), such as a field programmable gate array (FPGA), which is a processor whose circuit configuration can be changed after manufacture, and/or a dedicated electric circuit, such as an application specific integrated circuit (ASIC), which is a processor having a dedicated circuit configuration designed to perform a specific process.

One processing unit may be configured by one of the various processors or a combination of two or more processors of the same type or different types (for example, a combination of a plurality of FPGAs and/or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured using one or more of the various processors as the hardware structure.

In addition, specifically, an electric circuit (circuitry) obtained by combining circuit elements, such as semiconductor elements, can be used as the hardware structure of the various processors.

The inventions described in the following Supplementary Notes 1 to 3 related to an image processing device can be understood from the above description. In addition, in each of the above-described embodiments, the control device 12 is an example of the "image processing device".

Supplementary Note 1

There is provided an image processing device that is used in a radiography apparatus comprising a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction. The information processing device comprises a processor and a memory that is connected to or provided in the processor. The processor acquires a radiographic image of the subject from the imaging sensor, performs a process related to image quality on the radiographic image in a case in which a diagnosis image to be used for a doctor's diagnosis is generated from the radiographic image, and does not perform the process related to image quality on the radiographic image in a case in which a confirmation image for confirming a reflected state of the subject is generated from the radiographic image.

Supplementary Note 2

There is provided a method for operating an image processing device that is used in a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction. The method comprises: acquiring a radiographic image of the subject from the imaging sensor; performing a process related to image quality on the radiographic image in a case in which a diagnosis image to be used for a doctor's diagnosis is generated from the radiographic image; and not performing the process related to image quality on the radiographic image in a case in which a confirmation image for confirming a reflected state of the subject is generated from the radiographic image.

Supplementary Note 3

There is provided a program for operating an image processing device that is used in a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction. The program causes a computer to execute a process comprising: acquiring a radiographic image of the subject from the imaging sensor; performing a process related to image quality on the radiographic image in a case in which a diagnosis image to be used for a doctor's diagnosis is generated from the radiographic image; and not performing the process related to image quality on the radiographic image in a case in which a confirmation image for confirming a reflected state of the subject is generated from the radiographic image.

In the technology of the present disclosure, the above-described various embodiments and/or various modification examples may be combined with each other. In addition, the present disclosure is not limited to each of the above-described embodiments, and various configurations can be used without departing from the gist of the present disclosure. Furthermore, the technology of the present disclosure extends to a storage medium that non-temporarily stores a program, in addition to the program.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, in the content of the above description and illustration, the description of, for example, common technical knowledge that does not need to be particularly described to enable the implementation of the technology of the present disclosure is omitted in order to avoid confusion and facilitate the understanding of portions related to the technology of the present disclosure.

In the specification, "A and/or B" is synonymous with "at least one of A or B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A radiography apparatus comprising:
   a radiation source that irradiates a subject with radiation;
   a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction;
   a processor; and
   a memory that is connected to or provided in the processor,
   wherein the first imaging sensor has a first imaging region in which the pixels are arranged,
   the second imaging sensor has a second imaging region in which the pixels are arranged,
   the first imaging sensor is disposed closer to an incident side of the radiation than the second imaging sensor in the thickness direction,
   in the second imaging region, a reflected region in which the first end portion is reflected is present in at least an overlap region in which the first end portion and the second end portion overlap each other,
   the first imaging region and the second imaging region overlap each other in the overlap region in a plan view of the imaging sensor unit in the thickness direction, and
   a marker that is reflected in both the first imaging sensor and the second imaging sensor is attached to the radiation detector at a preset position, and
   wherein the processor
      detects a positional deviation of the first imaging sensor and the second imaging sensor on the basis of the set position and a position where the marker is actually reflected,
      specifies the reflected region on the basis of the detected positional deviation,
      acquires a radiographic image of the subject from the imaging sensor,
      removes a signal of the reflected region from the radiographic image in a case in which a diagnosis image to be used for a doctor's diagnosis is generated from the radiographic image, and
      does not remove the signal of the reflected region from the radiographic image in a case in which a confirmation image for confirming a reflected state of the subject is generated from the radiographic image.

2. A radiography apparatus comprising:
   a radiation source that irradiates a subject with radiation;
   a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction;
   a processor; and
   a memory that is connected to or provided in the processor,
   wherein the first imaging sensor has a first imaging region in which the pixels are arranged,
   the second imaging sensor has a second imaging region in which the pixels are arranged,
   the first imaging sensor is disposed closer to an incident side of the radiation than the second imaging sensor in the thickness direction,
   in the second imaging region, a reflected region in which the first end portion is reflected is present in at least an overlap region in which the first end portion and the second end portion overlap each other, and
   an irradiation angle of the radiation with respect to the radiation detector is changeable, and
   wherein the processor
      specifies the reflected region that changes depending on the irradiation angle,
      acquires a radiographic image of the subject from the imaging sensor,
      removes a signal of the reflected region from the radiographic image in a case in which a diagnosis image to be used for a doctor's diagnosis is generated from the radiographic image, and
      does not remove the signal of the reflected region from the radiographic image in a case in which a confirmation image for confirming a reflected state of the subject is generated from the radiographic image.

3. A radiography apparatus comprising:
   a radiation source that irradiates a subject with radiation;
   a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction;
   a processor; and
   a memory that is connected to or provided in the processor,
   wherein the first imaging sensor has a first imaging region in which the pixels are arranged,
   the second imaging sensor has a second imaging region in which the pixels are arranged,
   the first imaging sensor is disposed closer to an incident side of the radiation than the second imaging sensor in the thickness direction,
   in the second imaging region, a reflected region in which the first end portion is reflected is present in at least an overlap region in which the first end portion and the second end portion overlap each other, and the radiation is capable of being obliquely incident on the overlap region, and a size of a focus of the radiation is changeable, and wherein the processor specifies the reflected region that changes depending on the size of the focus, acquires a radiographic image of the subject from the imaging sensor, removes a signal of the reflected region from the radiographic image in a case in which a diagnosis image to be used for a doctor's diagnosis is generated from the radiographic image, and does not remove the signal of the reflected region from the radiographic image in a case in which a confirmation image for confirming a reflected state of the subject is generated from the radiographic image.

4. The radiography apparatus according to claim 2, wherein a distance between the first imaging sensor and the second imaging sensor in the thickness direction is equal to or less than 2 mm.

5. The radiography apparatus according to claim 1, wherein a width of the reflected region is equal to or less than 10 mm.

6. The radiography apparatus according to claim 5, wherein a length of one side of the imaging sensor is equal to or greater than 300 mm.

7. The radiography apparatus according to claim 1, wherein the radiation detector includes a support table having an attachment surface which is convex toward an opposite side of the radiation source and to which the imaging sensor unit is attached following the convex shape.

8. The radiography apparatus according to claim 7, wherein the convex shape is a U-shape or a V-shape.

9. The radiography apparatus according to claim 8, wherein, in a case in which the convex shape is the U-shape, a tangent line between the first imaging sensor and the second imaging sensor in the overlap region is parallel to a tangent line between the second imaging sensor and the support table in the overlap region.

10. The radiography apparatus according to claim 8, wherein, in a case in which the convex shape is the U-shape, centers of curvature of at least two imaging sensors are located at the same position.

11. The radiography apparatus according to claim 1, wherein the imaging sensor unit includes two imaging sensors of the first imaging sensor and the second imaging sensor.

12. The radiography apparatus according to claim 1, wherein the imaging sensor is a sensor panel in which the pixels including thin film transistors are two-dimensionally arranged.

13. The radiography apparatus according to claim 12, wherein a substrate of the sensor panel is made of a resin.

14. The radiography apparatus according to claim 1, further comprising:

an annular frame to which the radiation source and the radiation detector are attached and in which the subject is positioned in a cavity; and a rotation mechanism that rotates the frame around the subject to capture the radiographic images at different angles, wherein the radiation detector includes a support table having an attachment surface which has an arc surface shape toward an opposite side of the radiation source and to which the imaging sensor unit is attached following the arc surface shape.

15. The radiography apparatus according to claim 14, wherein the radiography apparatus is a computed tomography apparatus that generates a tomographic image of the subject as the diagnosis image on the basis of a plurality of the radiographic images captured at different angles.

16. The radiography apparatus according to claim 15, wherein the confirmation image is a scout image that is obtained by scout imaging performed before the tomographic image is captured.

17. The radiography apparatus according to claim 15, wherein the confirmation image is a preview image that is generated on the basis of one of the plurality of radiographic images captured at different angles and is displayed before the tomographic image is displayed.

18. The radiography apparatus according to claim 14, wherein the radiation source emits the radiation having a conical shape.

19. The radiography apparatus according to claim 14, wherein the subject is positioned in the cavity in either a standing posture or a sitting posture.

20. A method for operating a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction, wherein the first imaging sensor has a first imaging region in which the pixels are arranged, the second imaging sensor has a second imaging region in which the pixels are arranged, the first imaging sensor is disposed closer to an incident side of the radiation than the second imaging sensor in the thickness direction, in the second imaging region, a reflected region in which the first end portion is reflected is present in at least an overlap region in which the first end portion and the second end portion overlap each other, the first imaging region and the second imaging region overlap each other in the overlap region in a plan view of the imaging sensor unit in the thickness direction, and a marker that is reflected in both the first imaging sensor and the second imaging sensor is attached to the radiation detector at a preset position, the method comprising:

detecting a positional deviation of the first imaging sensor and the second imaging sensor on the basis of the set position and a position where the marker is actually reflected;

specifying the reflected region on the basis of the detected positional deviation;

acquiring a radiographic image of the subject from the imaging sensor;

removing a signal of the reflected region from the radiographic image in a case in which a diagnosis image to be used for a doctor's diagnosis is generated from the radiographic image; and not removing the signal of the reflected region from the radiographic image in a case in which a confirmation image for confirming a reflected state of the subject is generated from the radiographic image.

21. A non-transitory computer-readable storage medium storing a program for operating a radiography apparatus including a radiation source that irradiates a subject with radiation and a radiation detector having an imaging sensor unit which includes at least two imaging sensors of a first imaging sensor and a second imaging sensor that have a rectangular plate shape and include pixels that sense the radiation or visible light converted from the radiation and generate charge and in which a first end portion of the first imaging sensor and a second end portion of the second imaging sensor are arranged to overlap each other in a thickness direction, wherein the first imaging sensor has a first imaging region in which the pixels are arranged, the second imaging sensor has a second imaging region in which the pixels are arranged, the first imaging sensor is disposed closer to an incident side of the radiation than the second imaging sensor in the thickness direction, in the second imaging region, a reflected region in which the first end portion is reflected is present in at least an overlap region in which the first end portion and the second end portion overlap each other, the first imaging region and the second imaging region overlap each other in the overlap region in a plan view of the imaging sensor unit in the thickness direction, and a marker that is reflected in both the first imaging sensor and the second imaging sensor is attached to the radiation detector at a preset position, the program causing a computer to execute a process comprising:

detecting a positional deviation of the first imaging sensor and the second imaging sensor on the basis of the set position and a position where the marker is actually reflected;

specifying the reflected region on the basis of the detected positional deviation;

acquiring a radiographic image of the subject from the imaging sensor;

removing a signal of the reflected region from the radiographic image in a case in which a diagnosis image to be used for a doctor's diagnosis is generated from the radiographic image; and not removing the signal of the reflected region from the radiographic image in a case in which a confirmation image for confirming a reflected state of the subject is generated from the radiographic image.

* * * * *